(12) United States Patent
Alig et al.

(10) Patent No.: US 8,101,550 B2
(45) Date of Patent: *Jan. 24, 2012

(54) ANTHRANILIC ACID DIAMIDE DERIVATIVE WITH HETERO-AROMATIC AND HETERO-CYCLIC SUBSTITUENTS

(75) Inventors: Bernd Alig, Königswinter (DE); Rüdiger Fischer, Pulheim (DE); Christian Funke, Leichlingen (DE); Ernst Rudolf F. Gesing, Erkrath (DE); Achim Hense, Leverkusen (DE); Olga Malsam, Rösrath (DE); Mark Wilhelm Drewes, Langenfeld (DE); Ulrich Görgens, Ratingen (DE); Tetsuya Murata, Tochigi (JP); Katsuaki Wada, Tochigi (JP); Christian Arnold, Langenfeld (DE); Erich Sanwald, Kiel (DE)

(73) Assignee: Bayer Cropscience AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/304,630

(22) PCT Filed: Jun. 6, 2007

(86) PCT No.: PCT/EP2007/005016
§ 371 (c)(1),
(2), (4) Date: May 20, 2009

(87) PCT Pub. No.: WO2007/144100
PCT Pub. Date: Dec. 21, 2007

(65) Prior Publication Data
US 2010/0029478 A1 Feb. 4, 2010

(30) Foreign Application Priority Data

Jun. 13, 2006 (DE) .......................... 10 2006 027 336
Jul. 12, 2006 (DE) .......................... 10 2006 032 168

(51) Int. Cl.
*A01C 1/06* (2006.01)
*C07D 231/10* (2006.01)
*C07D 401/02* (2006.01)
*A01N 43/56* (2006.01)

(52) U.S. Cl. ..... 504/100; 514/341; 514/406; 546/275.4; 548/374.1

(58) Field of Classification Search .......................... None
See application file for complete search history.

(56) References Cited

FOREIGN PATENT DOCUMENTS

| WO | 0170671 | 9/2001 |
|---|---|---|
| WO | 03015518 | 2/2003 |
| WO | 03015519 | 2/2003 |
| WO | 03016282 | 2/2003 |
| WO | 03016283 | 2/2003 |
| WO | 03016284 | 2/2003 |
| WO | 03024222 | 3/2003 |
| WO | 03027099 | 4/2003 |
| WO | 03062226 | 7/2003 |
| WO | 2004027042 | 4/2004 |
| WO | 2004033468 | 4/2004 |
| WO | 2004046129 | 6/2004 |
| WO | 2004067528 | 8/2004 |
| WO | 2005018557 | 3/2005 |
| WO | 2005077934 | 8/2005 |
| WO | 2005085234 | 9/2005 |
| WO | 2005118552 | 12/2005 |
| WO | 2006000336 | 1/2006 |
| WO | 2006023783 | 3/2006 |
| WO | 2006040113 | 4/2006 |
| WO | 2006111341 | 10/2006 |
| WO | 2007006670 | 1/2007 |
| WO | 2007020877 | 2/2007 |
| WO | 2007024833 | 3/2007 |

OTHER PUBLICATIONS

Mengak, Snakes and Their Control, 2002, Cooperative Extension Service/The University of Georgia.*
Miura et al., caplus an 2007:510466.*
International Search Report from PCT/EP2007/005016, dated Sep. 19, 2007, (4 pages).

* cited by examiner

*Primary Examiner* — Sun Jae Loewe
(74) *Attorney, Agent, or Firm* — Baker Donelson Bearman, Caldwell & Berkowitz, PC

(57) ABSTRACT

The present invention relates to new insecticides of the formula (I)

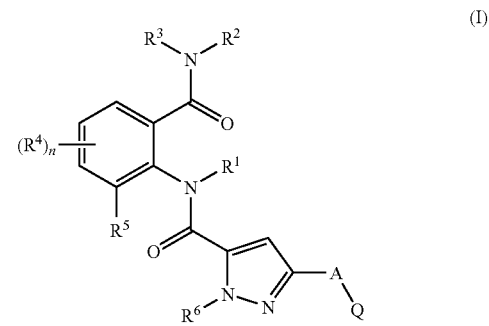

in which $R^1$, $R^2$, $R^3$, $R^4$, $R^5$, $R^6$, A, Q and n can have the definitions stated in the description, to a number of processes for preparing them and to their use as active compounds, more particularly to their use as pest control compositions.

13 Claims, No Drawings

ANTHRANILIC ACID DIAMIDE DERIVATIVE WITH HETERO-AROMATIC AND HETERO-CYCLIC SUBSTITUENTS

CROSS REFERENCE TO RELATED APPLICATIONS

This application is a §371 National Stage Application of PCT/EP2007/005016 filed Jun. 13, 2007 which claims priority from German Application 10 2006 027 336.2 filed Jun. 13, 2006 and German Application 10 2006 032 168.5 filed Jul. 12, 2006.

BACKGROUND OF THE INVENTION

1. Field of the Invention

The present invention relates to new insecticides, to a number of processes for their preparation and to their use as active compounds, more particularly to their use as pest control agents.

2. Description of Related Art

It is already known that certain anthranilamides (e.g. WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO 2007/020877) possess insecticidal properties.

The activity of these compounds, though good, is nevertheless found wanting in certain cases.

SUMMARY OF THE INVENTION

New anthranilamides have now been found, of the formula (I)

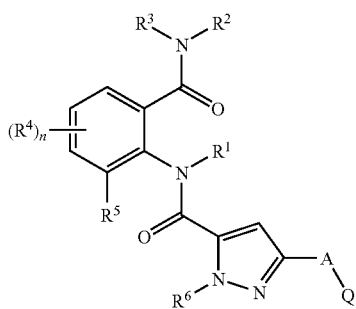

in which $R^1$ represents hydrogen, amino or hydroxyl or represents $C_1$-$C_6$-alkyl, $C_2$-$C_6$-alkenyl, $C_2$-$C_6$-alkynyl or $C_3$-$C_6$-cycloalkyl each of which is unsubstituted or substituted one or more times by identical or different substituents selectable independently of one another from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino or ($C_1$-$C_4$-alkyl)$C_3$-$C_6$-cycloalkylamino, $R^2$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di($C_1$-$C_4$-alkyl)amino, $C_3$-$C_6$-cycloalkylamino, $C_2$-$C_6$alkoxy-carbonyl or $C_2$-$C_6$-alkylcarbonyl, $R^3$ represents hydrogen or represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from amino, $C_3$-$C_6$-cycloalkylamino or a 5- or 6-membered heteroaromatic ring, $R^3$ likewise further represents $C_3$-$C_{12}$-cycloalkyl, $C_3$-$C_{12}$-cycloalkyl-$C_1$-$C_6$-alkyl and $C_4$-$C_{12}$-bicycloalkyl, the substituents being selectable independently of one another from halogen, cyano, nitro, hydroxyl, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-tri-alkylsilyl or a 5- or 6-membered heteroaromatic ring, $R^2$ and $R^3$ can be joined to one another via two to six carbon atoms and form a ring which where appropriate additionally contains a further nitrogen, sulphur or oxygen atom and where appropriate may be substituted one to four times by $C_1$-$C_2$-alkyl, halogen, cyano, amino or $C_1$-$C_2$-alkoxy, $R^2$ and $R^3$ further together represent =S($C_1$-$C_4$-alkyl)$_2$ or =S(O)($C_1$-$C_4$-alkyl)$_2$, $R^4$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two $R^4$s, via adjacent carbon atoms, form a ring which represents —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—, two $R^4$s further, via adjacent carbon atoms, form the following fused rings, which where appropriate are substituted one or more times by identical or different substituents selectable independently of one another from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio ($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino or $C_3$-$C_6$-cycloalkylamino,

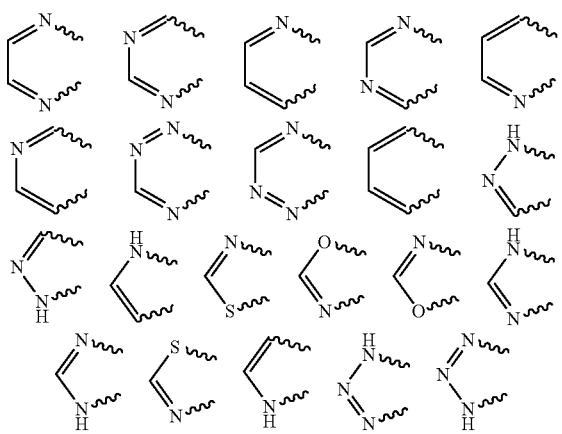

n represents 0 to 3, $R^5$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkyl-sulphinyl, $C_1$-$C_4$-haloalkylsulphonyl, halogen, cyano, nitro or $C_3$-$C_6$-trialkylsilyl, $R^6$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-halo-alkyl, $C_2$-$C_6$-haloalkenyl or

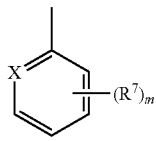

$R^6$ further represents $C_3$-$C_6$-cycloalkoxy, $R^7$ represents independently at each occurrence hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m represents 0 to 4, X represents N, CH, CF, CCl, CBr or CI, A represents —$CH_2$—, —$CH_2O$—, —$CH_2OCH_2$—, —$CH_2S$—, —$CH_2SCH_2$—, —$CH_2N(C_1$-$C_6$-alkyl)-, —$CH_2N(C_1$-$C_6$-alkyl)$CH_2$—, —$CH[CO_2(C_1$-$C_6$-alkyl)]-, —CH(CN)—, —$CH(C_1$-$C_6$-alkyl)-, —C(di-$C_1$-$C_6$-alkyl)-, —$CH_2CH_2$— or —C=$NO(C_1$-$C_6$-alkyl)-, Q represents a 5- or 6-membered heteroatomatic ring or an aromatic 8-, 9- or 10-membered fused heterobicyclic ring system, the ring system being unsubstituted or substituted one or more times by identical or different substituents selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$-alkyl)silyl and ($C_1$-$C_4$-alkyl)($C_1$-$C_4$-alkoxy)imino, Q further represents a 5- or 6-membered heteroaromatic or heterocyclic ring or an aromatic 8-, 9- or 10-membered fused heterobicyclic ring system, the ring or the ring system being unsubstituted or substituted one or more times by identical or different substituents selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$-alkyl)silyl and ($C_1$-$C_4$-alkyl)($C_1$-$C_4$-alkoxy)imino, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy substituents, and the compounds of the general formula (I) also encompass N-oxides and salts.

Finally it has been found that the compounds of the formula (I) according to the invention possess very good insecticidal properties and can be used, not only in crop protection but also in materials protection, for controlling unwanted pests, such as insects.

The compounds of the invention may where appropriate take the form of mixtures of different possible isomeric forms, more particularly of stereoisomers, such as, for example, E and Z isomers, threo and erythro isomers, and optical isomers, and also, where appropriate, of tautomers. The E and the Z isomers, the threo and erythro isomers, and the optical isomers, any desired mixtures of these isomers, and also the possible tautomeric forms are all claimed.

DETAILED DESCRIPTION OF A PREFERRED EMBODIMENT

A general definition of the anthranilamides of the invention is given by the formula (I). Preferred radical definitions for the formulae given above and below are specified below. These definitions apply equally to the end products of the formula (I) as to all intermediates.

$R^1$ preferably represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkyl-sulphonyl-$C_1$-$C_4$-alkyl.

$R^1$ more preferably represents hydrogen, methyl, cyclopropyl, cyanomethyl, methoxymethyl, methylthiomethyl, methylsulphinylmethyl or methylsulphonylmethyl.

$R^1$ very preferably represents hydrogen.

$R^2$ preferably represents hydrogen or $C_1$-$C_6$-alkyl.

$R^2$ more preferably represents hydrogen or methyl.

$R^2$ very preferably represents hydrogen.

$R^3$ preferably represents hydrogen or represents $C_1$-$C_6$-alkyl, $C_1$-$C_6$-alkoxy, $C_2$-$C_6$-alkenyl or $C_2$-$C_6$-alkynyl each of which is unsubstituted or substituted one or more times by identical or different substituents selectable from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further preferably represents $C_3$-$C_{12}$-cycloalkyl and $C_4$-$C_{10}$-bicycloalkyl, the substituents being selectable independently of one another from halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ more preferably represents hydrogen or represents $C_1$-$C_6$-alkyl, $C_1$-$C_6$-alkoxy each of which is unsubstituted or substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkyl-sulphoximino-$C_1$-$C_4$-alkyl, $C_1$-$C_4$-alkylsulphoximino-$C_2$-$C_5$-alkylcarbonyl, $C_2$-$C_6$-alkoxy-carbonyl, $C_2$-$C_6$-alkylcarbonyl or $C_3$-$C_6$-trialkylsilyl, $R^3$ further more preferably represents $C_3$-$C_6$-cycloalkyl which is unsubstituted or substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-halo-alkoxy, $C_1$-$C_4$-alkylthio, $C_1$-$C_4$-alkylsulphinyl, $C_1$-$C_4$-alkylsulphonyl, $C_{1-4}$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ very preferably represents $C_1$-$C_4$-alkyl (methyl, ethyl, n-propyl, isopropyl, n-butyl, isobutyl, sec-butyl or tert-butyl) or cyano-$C_1$-$C_3$-alkyl (cyanomethyl, 1-cyanoethyl, 2-cyanoethyl, 1-cyano-n-propyl, 2-cyano-n-propyl, 3-cyano-n-propyl, 1-cyanoisopropyl, 2-cyanoisopropyl).

$R^3$ with particular preference represents methyl, isopropyl or cyanomethyl.

$R^4$ preferably represents hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio.

Preferably, moreover, two adjacent radicals $R^4$ represent —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—.

$R^4$ more preferably represents hydrogen, $C_1$-$C_4$-alkyl, $C_1$-$C_2$-haloalkyl, halogen, cyano or $C_1$-$C_2$-haloalkoxy.

More preferably, moreover, two adjacent radicals $R^4$ represent —(CH$_2$)$_4$—, —(CH=CH—)$_2$—, —O(CH$_2$)$_2$O—, —O(CF$_2$)$_2$O—, —(CH=CH—CH=N)— or —(CH=CH—N=CH)—.

$R^4$ very preferably represents hydrogen, methyl, trifluoromethyl, cyano, fluorine, chlorine, bromine, iodine or trifluoromethoxy. Very preferably, moreover, two adjacent radicals $R^4$ represent —(CH$_2$)$_4$—, or —(CH=CH—)$_2$—.

$R^4$ with particular preference represents chlorine or bromine, $R^4$ further with particular preference represents iodine or cyano. With particular preference, moreover, two adjacent radicals $R^4$ represent —(CH=CH—)$_2$—.

$R^5$ preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-halo-alkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl.

$R^5$ more preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl.

$R^5$ very preferably represents methyl, fluorine, chlorine, bromine or iodine.

$R^5$ with particular preference represents methyl or chlorine.

$R^6$ preferably represents $C_1$-$C_6$-alkyl or

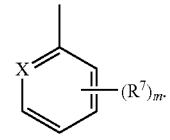

$R^6$ further preferably represents $C_3$-$C_6$-cycloalkoxy.

$R^6$ more preferably represents methyl or

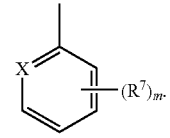

$R^7$ independently at each occurrence preferably represents hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalkylsulphonyl or ($C_1$-$C_4$-alkyl)$C_1$-$C_4$-alkoxyimino, $R^7$ independently at each occurrence more preferably represents hydrogen, halogen or $C_1$-$C_4$-haloalkyl, $R^7$ very preferably represents fluorine, chlorine or bromine, $R^7$ with particular preference represents chlorine.

m preferably represents 1, 2 or 3, m more preferably represents 1 or 2, m very preferably represents 1, X preferably represents N, CH, CF, CCl, CBr or CI, X more preferably represents N, CH, CF, CCl or CBr, X very preferably represents N, CCl or CH.

A preferably represents —CH$_2$—, —CH$_2$O—, —CH$_2$OCH$_2$—, —CH$_2$S—, —CH$_2$SCH$_2$—, —CH$_2$N($C_1$-$C_6$-alkyl)-, —CH$_2$N($C_1$-$C_6$-alkyl)CH$_2$—, —CH(CN)—, —CH($C_1$-$C_6$-alkyl)-, —C(di-$C_1$-$C_6$-alkyl)-, —CH$_2$CH$_2$— or —C=NO($C_1$-$C_6$-alkyl)-, A more preferably represents —CH$_2$—, —CH(CH$_3$), C(CH$_3$)$_2$ or CH$_2$CH$_2$, A further more preferably represents —CH(CN)—, A very preferably represents CH$_2$ or CH(CH$_3$), A with particular preference represents CH$_2$.

Q preferably represents an optionally mono- or polysubstituted 5- or 6-membered aromatic heterocyclic ring of series Q-1 to Q-53 or an aromatic 9-membered fused heterobicyclic ring system Q-54 to Q-56, the substituents being selectable independently of one another from C$_1$-C$_3$-alkyl, C$_1$-C$_3$-haloalkyl, C$_1$-C$_2$-alkoxy, halogen, cyano, hydroxyl, nitro or C$_1$-C$_2$-haloalkoxy.

Q further preferably represents an optionally mono- or polysubstituted 5- or 6-membered aromatic heterocyclic ring of series Q-1 to Q-53 and Q-58 to Q-59, an aromatic 9-membered fused heterobicyclic ring system Q-54 to Q-56 and also represents a 5-membered heterocyclic ring Q-60 to Q-61, the substituents being selectable independently of one another from C$_1$-C$_3$-alkyl, C$_1$-C$_3$-haloalkyl, C$_1$-C$_2$-alkoxy, halogen, cyano, hydroxyl, nitro or C$_1$-C$_2$-haloalkoxy, or the substituents being selectable independently of one another from phenyl or a 5- or 6-membered heteroaromatic ring, it being possible for phenyl or the ring to be substituted where appropriate one or more times by identical or different C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, NO$_2$, OH, C$_1$-C$_4$-alkoxy or C$_1$-C$_4$-haloalkoxy substituents, Q more preferably represents an optionally mono- or polysubstituted 5- or 6-membered aromatic heterocyclic ring of series Q-36 to Q-40 or an aromatic 9-membered fused heterobicyclic ring system Q-54 to Q-56, the substituents being selectable independently of one another from C$_1$-C$_3$-alkyl, C$_1$-C$_3$-haloalkyl, C$_1$-C$_2$-alkoxy, halogen, cyano, hydroxyl, nitro or C$_1$-C$_2$-haloalkoxy.

Q further more preferably represents an optionally mono- or polysubstituted 5- or 6-membered aromatic heterocyclic ring of series Q-36 to Q-40 and Q-58 to Q-59, an aromatic 9-membered fused heterobicyclic ring system Q-54 to Q-56 and also represents a 5-membered heterocyclic ring Q-60 to Q-61, the substituents being selectable independently of one another from C$_1$-C$_3$-alkyl, C$_1$-C$_3$-haloalkyl, C$_1$-C$_2$-alkoxy, halogen, cyano, hydroxyl, nitro or C$_1$-C$_2$-haloalkoxy, or the substituents being selectable independently of one another from phenyl or a 5- or 6-membered heteroaromatic ring, it being possible for phenyl or the ring to be unsubstituted or substituted one or more times by identical or different C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, NO$_2$, C$_1$-C$_4$-alkoxy or C$_1$-C$_4$-haloalkoxy substituents, Q very preferably represents an optionally mono- or polysubstituted aromatic heterocyclic ring of series Q-37, Q-38, Q-39, Q-40, Q-58 and Q-59, and also represents a 5-membered heterocyclic ring Q-60, the substituents being selectable independently of one another from C$_1$-C$_3$-alkyl, C$_1$-C$_3$-haloalkyl, C$_1$-C$_2$-alkoxy, halogen, cyano, hydroxyl, nitro or C$_1$-C$_2$-haloalkoxy, or the substituents being selectable independently of one another from phenyl or a 5- or 6-membered heteroaromatic ring, it being possible for phenyl or the ring to be unsubstituted or substituted one or more times by identical or different C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, NO$_2$, C$_1$-C$_4$-alkoxy or C$_1$-C$_4$-haloalkoxy substituents, Q further very preferably represents an optionally mono- or polysubstituted aromatic heterocyclic ring of series Q-37, Q-38, Q-39, Q-40, Q-58 and Q-59, and also represents a 5-membered heterocyclic ring Q-60, the substituents being selectable independently of one another from C$_1$-C$_3$-alkyl, C$_1$-C$_3$-haloalkyl, halogen, cyano, nitro or C$_1$-C$_2$-haloalkoxy, or the substituents being selectable independently of one another from phenyl or a 5- or 6-membered heteroaromatic ring, it being possible for phenyl or the ring to be unsubstituted or substituted one or more times by identical or different C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, NO$_2$, C$_1$-C$_4$-alkoxy or C$_1$-C$_4$-haloalkoxy substituents, Q with particular preference represents an aromatic heterocyclic ring Q-37, Q-40, Q-58 and Q-59 which is unsubstituted or substituted once, twice or three times on carbon atoms, and also represents a 5-membered heterocyclic ring Q-60, the substituents being selectable independently of one another from chlorine, fluorine, iodine, bromine, cyano, trifluoromethyl and pentafluoroethyl, or the substituents being selectable independently of one another from phenyl, it being possible for the phenyl ring to be unsubstituted or substituted one or more times by identical or different C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, NO$_2$ or C$_1$-C$_4$-haloalkoxy substituents, Q further with particular preference represents an optionally mono- or polysubstituted aromatic heterocyclic ring of series Q-37, Q-40, Q-58 and Q-59, and also represents a 5-membered heterocyclic ring Q-60, the substituents being selectable independently of one another from chlorine, fluorine, iodine, cyano, trifluoromethyl and pentafluoroethyl, or the substituents being selectable independently of one another from phenyl, it being possible for the phenyl ring to be unsubstituted or substituted one or more times by identical or different chlorine, fluorine, iodine, bromine, cyano, trifluoromethyl and pentafluoroethyl substituents,

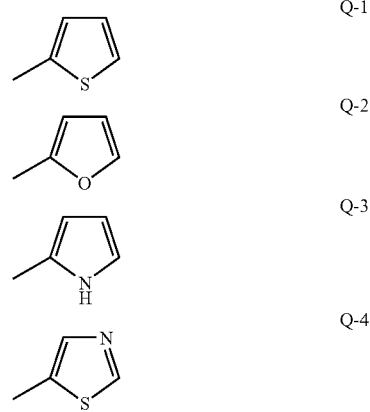

-continued
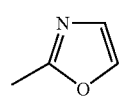 Q-5
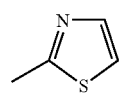 Q-6
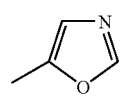 Q-7
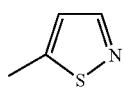 Q-8
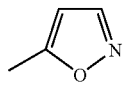 Q-9
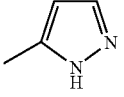 Q-10
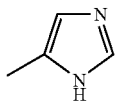 Q-11
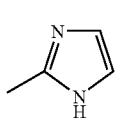 Q-12
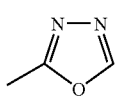 Q-13
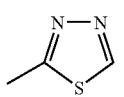 Q-14
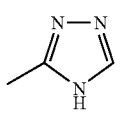 Q-15
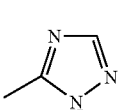 Q-16
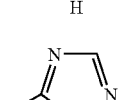 Q-17
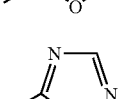 Q-18
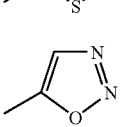 Q-19
-continued
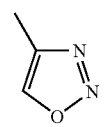 Q-20
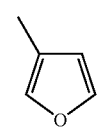 Q-21
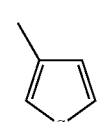 Q-22
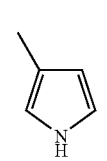 Q-23
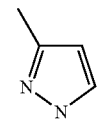 Q-24
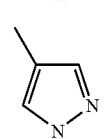 Q-25
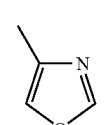 Q-26
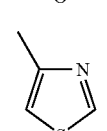 Q-27
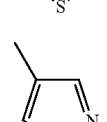 Q-28
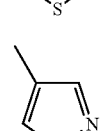 Q-29
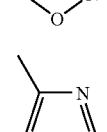 Q-30
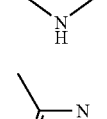 Q-31
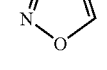

| | |
|---|---|
| 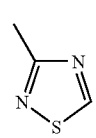 | Q-32 |
| 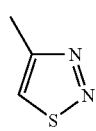 | Q-33 |
| 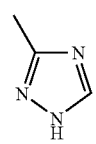 | Q-34 |
| 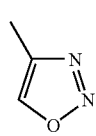 | Q-35 |
| 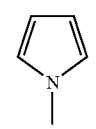 | Q-36 |
| 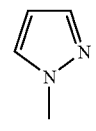 | Q-37 |
| 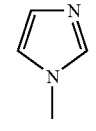 | Q-38 |
| 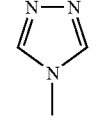 | Q-39 |
| 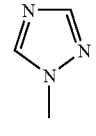 | Q-40 |
|  | Q-41 |
| 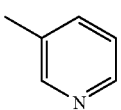 | Q-42 |
| 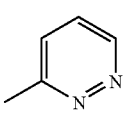 | Q-43 |
| | |
|---|---|
| 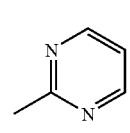 | Q-44 |
| 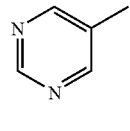 | Q-45 |
| 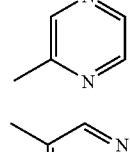 | Q-46 |
| 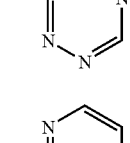 | Q-47 |
| 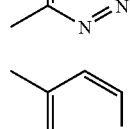 | Q-48 |
| 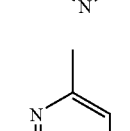 | Q-49 |
| 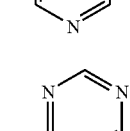 | Q-50 |
| 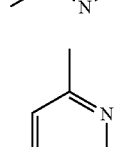 | Q-51 |
| 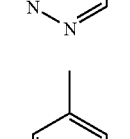 | Q-52 |
| 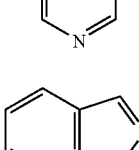 | Q-53 |
| 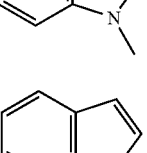 | Q-54 |
| | Q-55 |

13

-continued

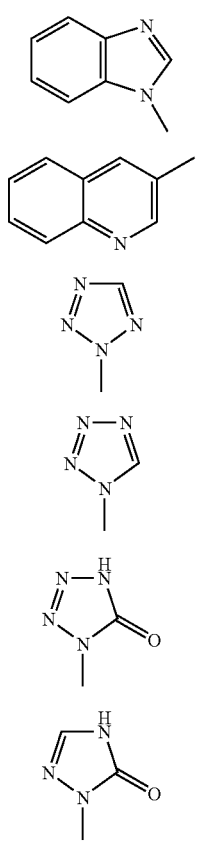

Q-56

Q-57

Q-58

Q-59

Q-60

Q-61

Emphasis is given to compounds of the formula (I-1)

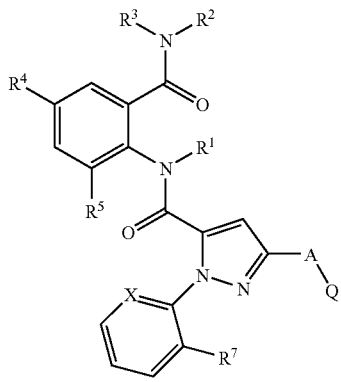

(I-1)

in which $R^1$, $R^2$, $R^3$, $R^4$, $R^5$, $R^7$, A, Q and X have the above-indicated general, preferred, more preferred, very preferred and particularly preferred definitions.

Radicals substituted by halogen, haloalkyl for example, are halogenated one or more times up to the maximum possible number of substituents. In the case of multiple halogenation, the halogen atoms can be alike or different. Halogen here stands for fluorine, chlorine, bromine or iodine, in particular for fluorine, chlorine or bromine.

Preference, more preference, great preference and particular preference is given to compounds which carry in each case the substituents stated as being preferred, more preferred, very preferred and particularly preferred.

14

Saturated or unsaturated hydrocarbon radicals such as alkyl or alkenyl, both alone and in conjunction with heteroatoms, as in alkoxy, for example, may where possible be in each case linear or branched.

Unsubstituted or substituted radicals may be substituted one or more times, and in the case of multiple substitutions the substituents can be alike or different.

The definitions of radicals and elucidations given generally or in ranges of preference above may, however, also be combined arbitrarily with one another, in other words combined between the respective ranges and the ranges of preference. They apply to the end products and also to the precursors and intermediates accordingly.

It has additionally been found that anthranilamides of the formula (I) are obtained by one of the following processes.

Anthranilamides of the Formula (I)

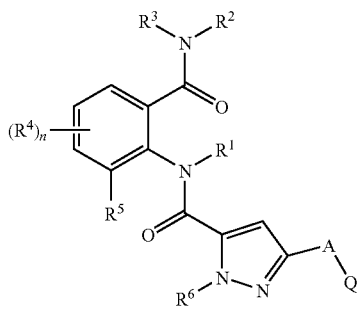

(I)

in which A, $R^1$, $R^2$, $R^3$, $R^4$, $R^5$, $R^6$, Q and n have the definitions stated above are obtained by (A) reacting anilines of the formula (II)

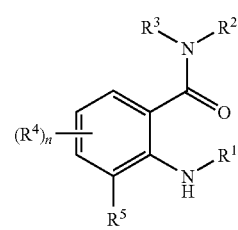

(II)

in which A, $R^1$, $R^2$, $R^3$, $R^4$, $R^5$ and n have the definitions stated above with carbonyl chlorides of the formula (III)

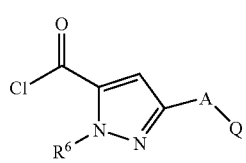

(III)

in which $R^6$, A and Q have the definitions stated above, in the presence of an acid-binding agent, (B) reacting anilines of the formula (II)

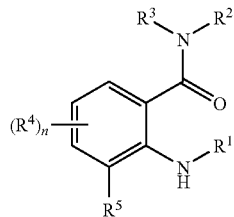

in which A, $R^1$, $R^2$, $R^3$, $R^4$, $R^5$ and n have the definitions stated above with a carboxylic acid of the formula (IV)

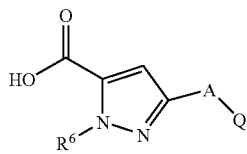

in which $R^6$, A and Q have the definitions stated above in the presence of a condensing agent, or by (C) synthesizing anthranilamides of the formula (I) in which $R^1$ represents hydrogen by reacting benzoxazinones of the formula (V)

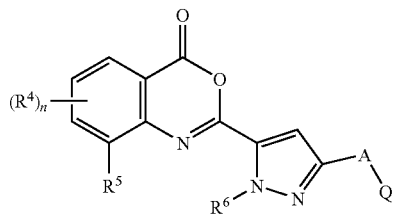

in which $R^4$, $R^5$, $R^6$, A, Q and n have the definitions stated above with an amine of the formula (XV)

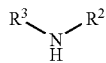

in which $R^2$ and $R^3$ have the definitions stated above, in the presence of a diluent.

Elucidation of the Processes and Intermediates

Process (A)

Using, for example, 2-amino-5-chloro-3,N-dimethylbenzamide and 5-(3,5-bistrifluoromethylpyrazol-1-ylmethyl)-2-(3-chloropyridin-2-yl)-2H-pyrazole-3-carbonyl chloride as starting materials, the course of process (A) of the invention can be illustrated by the following formula scheme.

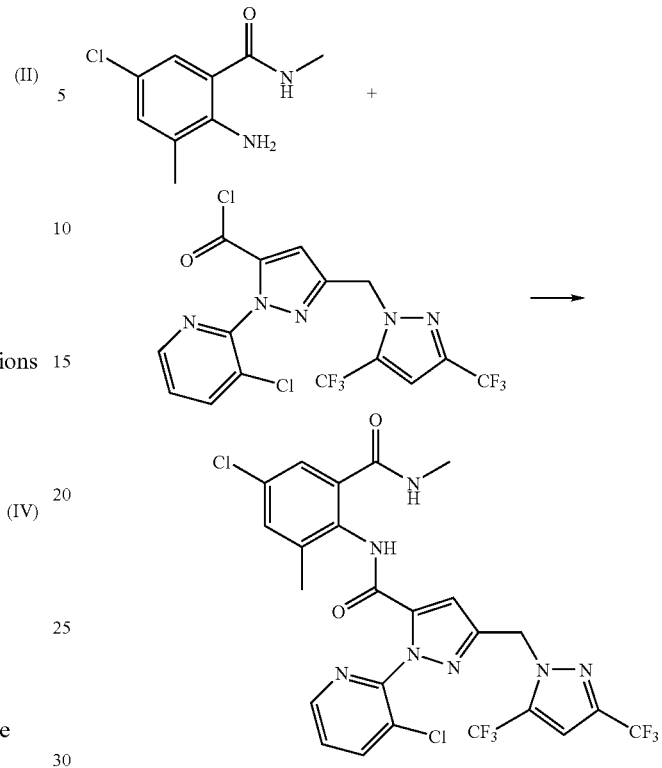

A general definition of the aminobenzamides required as starting materials when carrying out process (A) of the invention is given by the formula (II). In this formula (II) A, $R^1$, $R^2$, $R^3$, $R^4$, $R^5$ and n preferably, more preferably, very preferably and with particular preference represent those definitions which have already been given for these radicals in connection with the description of the compounds of the formula (I) according to the invention as being preferred, more preferred, etc.

Process (A) of the invention is carried out in the presence of an acid-binding agent. Suitable for this purpose are all organic or inorganic bases that are customary for such coupling reactions. With preference it is possible to use alkali metal or alkaline earth metal hydrides, hydroxides, amides, alkoxides, acetates, carbonates or hydrogen carbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium hydrogen carbonate, sodium hydrogen carbonate or ammonium carbonate, and also tertiary amines, such as trimethylamine, triethylamine, tributylamine, diisopropylethylamine, N,N-dimethylaniline, N,N-dimethylbenzylamine, pyridine, N-methylpiperidine, N-methylmorpholine, N,N-dimethylamino-pyridine, diazabicyclooctane (DABCO), diazabicyclononene (DBN) or diazabicycloundecene (DBU). It is also possible where appropriate to use polymer-supported acid-binding agents, such as polymer-bound diisopropylamine and polymer-bound dimethylaminopyridine, for example.

Process (A) of the invention where may appropriate be carried out in the presence of an inert organic diluent that is customary for such reactions. These diluents include preferably aliphatic, alcyclic or aromatic hydrocarbons, such as, for example, petroleum ether, hexane, heptane, cyclohexane, methyl-cyclohexane, benzene, toluene, xylene, or decalin;

halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoramide; mixtures thereof with water, or pure water. With particular preference it is possible to use toluene, tetrahydrofuran and N,N-dimethylformamide.

The reaction temperatures when carrying out process (A) of the invention can be varied within a relatively wide range. It is usual to operate at temperatures of 0° C. to 150° C., preferably at temperatures of 20° C. to 100° C.

The process of the invention is carried out in general under atmospheric pressure. It is, however, also possible to carry out the process of the invention under elevated or reduced pressure—in general of between 0.1 bar and 10 bar.

Aminobenzamides of the formula (II) are known (cf. e.g. M. J. Kornet, *J. Heterocyl. Chem.* 1992, 29, 103-105; G. P. Lahm et al., *Bioorg. Med. Chem. Letters* 2005, 15, 4898-4906; WO 2003/016284, WO 2006/062978).

Pyrazolecarbonyl chlorides of the formula (III) are new. They can be prepared, for example, by
(D) reacting pyrazolecarboxylic acid derivatives of the formula (IV)

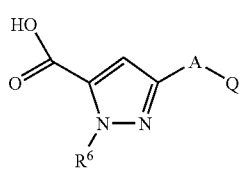

in which A, Q and $R^6$ have the definitions stated above
with a chlorinating agent (e.g. thionyl chloride and oxalyl chloride) in the presence of an inert diluent (e.g. toluene and dichloromethane) in the presence of a catalytic amount of N,N-dimethylformamide.

Pyrazolecarboxylic acid derivatives of the formula (IV) are new. They can be prepared, for example, by
(E) reacting pyrazolecarboxylic esters of the formula (VI)

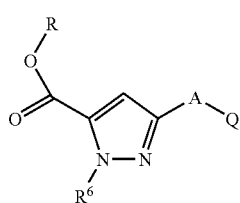

in which A, Q and $R^6$ have the definitions stated above and R represents $C_1$-$C_6$-alkyl
with an alkali metal hydroxide (e.g. sodium hydroxide or potassium hydroxide) in the presence of an inert diluent (e.g. dioxane/water or ethanol/water).

Pyrazolecarboxylic esters of the formula (VI) are new. They can be prepared, for example, by (F) reacting pyrazolecarboxylic ester derivatives of the formula (VII)

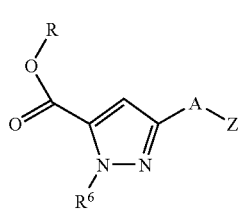

in which A, $R^6$ and R have the definitions stated above and Z represents chlorine, bromine, iodine, methylsulphonyl or toluenesulphonyl with a heteroaromatic of the formula (VIII) or with a boronic acid and/or boronic ester of the formula (IX), in which R' represents H, $CH_3$, $C_2H_5$ or R'-R' represents $C(CH_3)_2C(CH_3)_2$ and Q has the definitions stated above, in the presence of a transition metal (e.g. tetrakis(triphenylphosphine)palladium(0)) and a base (e.g. potassium carbonate or sodium carbonate) in the presence of a solvent (e.g. tetrahydrofuran, acetonitrile, or dioxane).

Heteroaromatics and heterocycles of the formula (VIII) are known, in some cases indeed being available commercially, or can be obtained by known processes (cf. e.g. H. V. Dias et al., Organometallics 1996, 15, 5374-5379; M. D. Threadgill et al., *J. Fluorine Chem.* 1993, 65, 21-23; M. Abdul-Ghani et al., *J. Fluorine Chem.* 1990, 48, 149-152; T. Kitazaki, *Chem. Pharm. Bull.* 1996, 44, 314-327; DE 1995-19504627; WO 2004080984, WO 2005095351).

Heterocyclic boronic acids or boronates of the formula (IX) are known, in some cases indeed being available commercially, or can be obtained by known processes (c.f. e.g. W. Li, D. P. Nelson, M. S. Jensen, R. S. Hoerrner, D. Cai, R. D. Larsen, P. J. Reider, *J. Org. Chem.* 2002, 67, 5394-5397).

Pyrazolecarboxylic ester derivatives of the formula (VII) can be prepared, for example, by
(G) reacting alcohols of the formula (X)

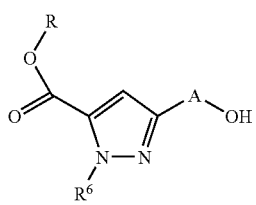

in which R, $R^6$ and A have the definitions stated above with a sulphonyl chloride (e.g. methylsulphonyl chloride or toluenesulphonyl chloride) or a halogenating agent (e.g. thionyl chloride) in the presence where appropriate of a solvent (e.g. dichloromethane) and in the presence where appropriate of a base (e.g. triethylamine or pyridine).

The reaction temperatures when carrying out process (G) of the invention can be varied within a relatively wide range. It is usual to operate at temperatures of 0° C. to 150° C., preferably at temperatures of 0° C. to 60° C.

Alcohols of the formula (X) can be prepared, for example, by (H) reacting pyrazoldicarboxylic esters of the formula (XI)

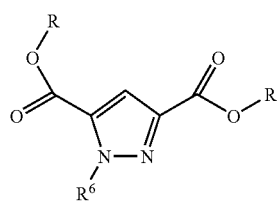
(XI)

in which R and R⁶ have the definitions stated above with a reducing agent (e.g. lithium aluminium hydride or diisobutylaluminium hydride) in the presence of a solvent (e.g. tetrahydrofuran or diethyl ether).

The reaction temperatures when carrying out process (H) of the invention can be varied within a relatively wide range. It is usual to operate at temperatures of −100° C. to 20° C., preferably at temperatures of −78° C. to 0° C.

Pyrazoldicarboxylic esters of the formula (XI) can be prepared, for example, by (I) reacting hydrazines or their corresponding salts of the formula (XII)

(XII)

in which R⁶ has the definition stated above with a triketone (XIII) of the formula (XIII)

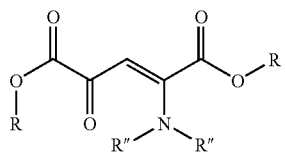
(XIII)

in which R has the definition stated above, R″ represents methyl or ethyl or R″-R″ represents (CH₂)₄ or (CH₂)₂—O—(CH₂)₂, in the presence of a solvent (e.g. methanol or ethanol).

Hydrazines or their corresponding salts of the formula (XII) are known, being in some cases commercially available, or can be prepared by general methods of synthesis (cf e.g. *Advanced Organic Chemistry*, Fourth Edition, Jerry March, John Wiley & Sons, Inc. New York, 1992, page 1288).

Triketones of the formula (XIII) are known and can be prepared by general synthesis methods (cf. e.g. Cvetovich, Raymond J.; Pipik, Brenda; Hartner, Frederick W.; Grabowski, Edward J. J.; *Tetrahedron Lett.* 2003, 44, 5867-5870).

The reaction temperatures when carrying out process (I) of the invention can be varied within a relatively wide range. It is usual to operate at temperatures of 0 to 80° C., preferably at temperatures of 40° C. to 60° C.

Process (B)

Using, for example, 2-amino-5-chloro-3,N-dimethylbenzamide and 5-(3,5-bistrifluoromethyl-pyrazol-1-ylmethyl)-2-(3-chloropyridin-2-yl)-2H-pyrazole-3-carboxylic acid as starting materials, the course of process (B) of the invention can be illustrated with the following formula scheme.

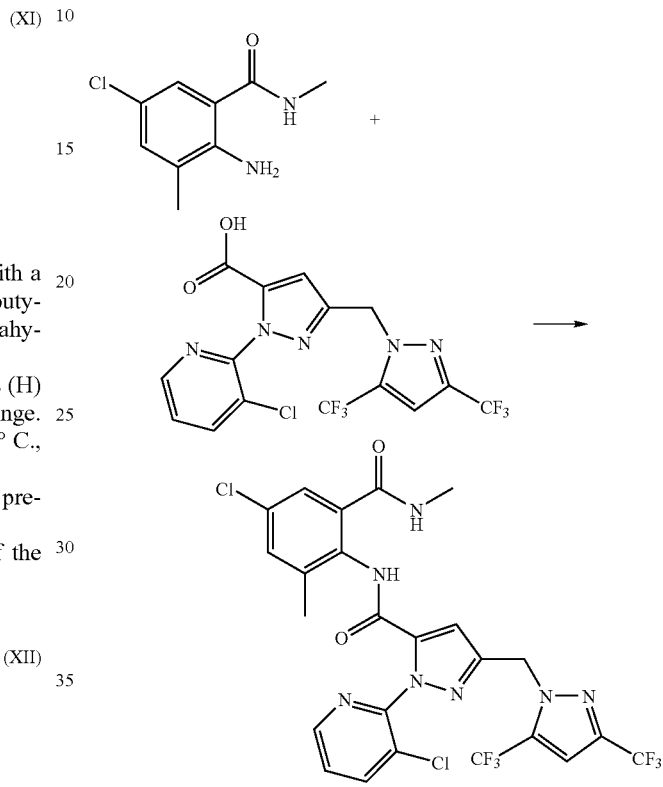

The anthranilamides of the formula (II) required as starting materials when carrying out process (B) of the invention have already been described in connection with process (A) of the invention.

A general definition of the heterocyclic carboxylic acids further required as starting materials when carrying out process (B) of the invention is given by the formula (IV). In this formula (IV) R⁶, A and Q represent preferably, more preferably, very preferably and with particular preference those definitions which have already been stated in connection with the description of the compounds of the formula (I) of the invention as being preferred, more preferred, etc. for these radicals.

Process (B) of the invention is carried out in the presence of a condensing agent. Suitability for this purpose is possessed by all agents customary for such coupling reactions. Mention may be made, by way of example, of acid halide formers such as phosgene, phosphorus tribromide, phosphorus trichloride, phosphorus pentachloride, phosphorus oxychloride or thionyl chloride; anhydride formers such as ethyl chloroformate, methyl chloroformate, isopropyl chloroformate, isobutyl chloroformate or methanesulphonyl chloride; carbodiimides, such as N,N′-dicyclohexylcarbodiimide (DCC) or other customary condensing agents, such as phosphorus pentoxide, polyphosphoric acid, 1,1′-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl) phosphine chloride or benzotriazol-1-yloxytris (dimethylamino)phosphonium hexafluorophosphate. Polymer-supported reactants, such as polymer-bound cyclohexylcarbodiimide, for example, may likewise be used.

Process (B) of the invention is carried out where appropriate in the presence of a catalyst. Mention may be made, by way of example, of 4-dimethylaminopyridine, 1-hydroxybenzotriazole or dimethylformamide.

Process (B) of the invention may where appropriate be carried out in the presence of an inert organic diluent typical for such reactions. Such diluents include preferably aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoramide; mixtures thereof with water, or pure water. With particular preference it is possible to use dichloromethane and N,N-dimethylformamide.

The reaction temperatures when carrying out process (B) of the invention can be varied within a relatively wide range. It is usual to operate at temperatures of 0° C. to 150° C., preferably at temperatures of 0° C. to 80° C.

The process of the invention is carried out in general under atmospheric pressure. It is, however, also possible to carry out the process of the invention under elevated or reduced pressure—in general of between 0.1 bar and 10 bar.

Process (C)

Using 2-[3-{[3,5-bis(trifluoromethyl)-1H-pyrazol-1-yl]methyl}-1-(3-chloropyridin-2-yl)-1H-pyrazol-5-yl]-6-chloro-8-methyl-4H-3,1-benzoxazin-4-one and methylamine, the course of process (C) of the invention can be illustrated with the following formula scheme.

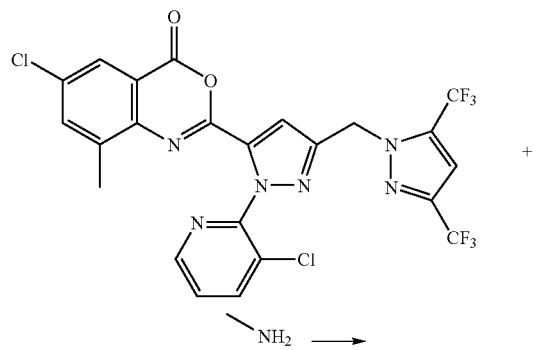

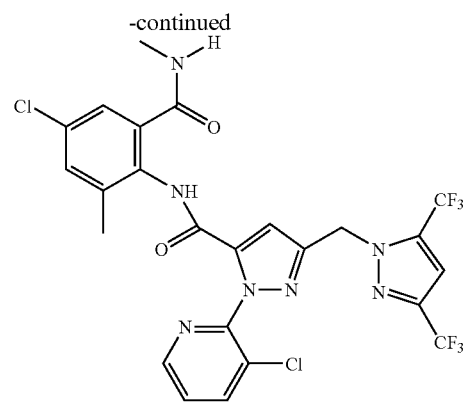

A general definition of the benzoxazinones required as starting materials when carrying out process (C) of the invention is given by the formula (V). In this formula (V) $R^4$, $R^5$, $R^6$, A, Q and n preferably, more preferably, very preferably and with particular preference represent those definitions which have already been given above in connection with the description of the compounds of the formula (I) of the invention as being preferred, more preferred, etc. for those radicals.

Benzoxazinones of the formula (V) are new. They are obtained, for example, by (J) reacting pyrazolecarboxylic acid derivatives of the formula (IV)

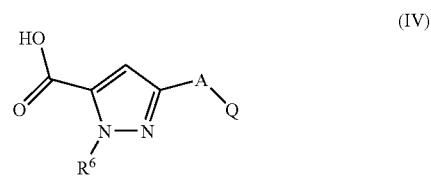

in which $R^6$, A and Q have the definitions stated above with anthranilic acids of the formula (XIV)

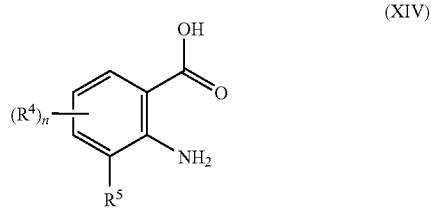

in which $R^4$, $R^5$ and n have the definitions stated above, in the presence of a base (e.g. triethylamine or pyridine) and in the presence of a sulphonyl chloride (e.g. methanesulphonyl chloride) and also, where appropriate, in the presence of a diluent (e.g. acetonitrile).

The pyrazolecarboxylic acid derivatives of the formula (IV) required as starting materials when carrying out process (J) of the invention have already been described above in connection with process (A) of the invention.

A general definition of the anthranilic acids additionally required as starting materials when carrying out process (J) of the invention is given by the formula (XIV). In this formula (XIV) $R^4$, $R^5$ and n preferably, more preferably, very preferably and with particular preference represent those definitions which have already been given above in connection with the description of the compounds of the formula (I) of the invention as being preferred, more preferred, etc. for those radicals.

Anthranilic acids of the formula (XIV) are known and can be prepared by general synthesis methods (cf. e.g. Baker et al., *J. Org. Chem.* 1952; 149-153; G. Reissenweber et al., *Angew. Chem.* 1981, 93, 914-915, P. J. Montoya-Pelaez, *J. Org. Chem.* 2006, 71, 5921-5929; F. E. Sheibley, *J. Org. Chem.* 1938, 3, 414-423, WO 2006023783).

The compounds of the formula (I) may where appropriate occur in different polymorphic forms or as a mixture of different polymorphic forms. Not only the pure polymorphs but also the polymorph mixtures are subject matter of the invention and can be used in accordance with the invention.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata,*

*Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis,* *Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat and/or POP-POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:
Inhibitors of Nucleic Acid Synthesis
  benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid
Inhibitors of Mitosis and Cell Division
  benomyl, carbendazim, diethofencarb, fuberidazole, pencycuron, thiabendazole, thiophanate-methyl, zoxamide
Inhibitors of Respiratory Chain Complex I
  diflumetorim
Inhibitors of Respiratory Chain Complex II
  boscalid, carboxin, fenfuram, flutolanil, furametpyr, mepronil, oxycarboxin, penthiopyrad, thifluzamide
Inhibitors of Respiratory Chain Complex III
  azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin
Decouplers
  dinocap, fluazinam
Inhibitors of ATP Production
  fentin acetate, fentin chloride, fentin hydroxide, silthiofam
Inhibitors of Amino Acid Biosynthesis and Protein Biosynthesis
  andoprim, blasticidin-S, cyprodinil, kasugamycin, kasugamycin hydrochloride hydrate, mepanipyrim, pyrimethanil
Inhibitors of Signal Transduction
  fenpiclonil, fludioxonil, quinoxyfen
Inhibitors of Lipid and Membrane Synthesis
  chlozolinate, iprodione, procymidone, vinclozolin
  ampropylfos, potassium-ampropylfos, edifenphos, iprobenfos (IBP), isoprothiolane, pyrazophos
  tolclofos-methyl, biphenyl
  iodocarb, propamocarb, propamocarb hydrochloride
Inhibitors of Ergosterol Biosynthesis
  fenhexamid,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole,
  aldimorph, dodemorph, dodemorph acetate, fenpropimorph, tridemorph, fenpropidin, spiroxamine,
  naftifine, pyributicarb, terbinafine
Inhibitors of Cell Wall Synthesis
  benthiavalicarb, bialaphos, dimethomorph, flumorph, iprovalicarb, polyoxins, polyoxorim, validamycin A
Inhibitors of Melanin Biosynthesis
  capropamid, diclocymet, fenoxanil, phthalid, pyroquilon, tricyclazole
Resistance Inductors
  acibenzolar-S-methyl, probenazole, tiadinil
Multisite
  captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram
Unknown Mechanism
  amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolenitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methyl-benzenesulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]-ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl) [1,2,4]triazolo[L 1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl) [1,2,4]triazolo[1,5-a]pyrimidin-7-amine, N-[L-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
  carbamates,
    for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
  organophosphates,
    for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
  pyrethroids,
    for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
  DDT
  oxadiazines,
    for example indoxacarb
  semicarbazone,
    for example metaflumizone (BAS3201)
Acetylcholine Receptor Agonists/Antagonists
  chloronicotinyls,
    for example acetamiprid, clothianidin, dinotefuran, imidacloprid, nitenpyram, nithiazine, thiacloprid, thiamethoxam
  nicotine, bensultap, cartap
Acetylcholine Receptor Modulators
  spinosyns,
    for example spinosad,
GABA-Controlled Chloride Channel Antagonists
  organochlorines,
    for example camphechlor, chlordane, endosulfan, gamma-HCH, HCH, heptachlor, lindane, methoxychlor
  fiproles,
    for example acetoprole, ethiprole, fipronil, pyrafluprole, pyriprole, vaniliprole Chloride Channel Activators
mectins,
for example abamectin, emamectin, emamectin-benzoate, ivermectin, lepimectin, milbemycin
Juvenile Hormone Mimetics,
for example diofenolan, epofenonane, fenoxycarb, hydroprene, kinoprene, methoprene, pyriproxifen, triprene
Ecdysone Agonists/Disruptors
diacylhydrazines,
for example chromafenozide, halofenozide, methoxyfenozide, tebufenozide
Chitin Biosynthesis Inhibitors
benzoylureas,
for example bistrifluron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine
Oxidative Phosphorylation Inhibitors, ATP Disruptors
diafenthiuron
organotin compounds,
for example azocyclotin, cyhexatin, fenbutatin-oxide
Oxidative Phosphorylation Decouplers Acting by Interrupting the H-Proton Gradient
pyrroles,
for example chlorfenapyr
dinitrophenols,
for example binapacyrl, dinobuton, dinocap, DNOC
Site-I Electron Transport Inhibitors
METIs,
for example fenazaquin, fenpyroximate, pyrimidifen, pyridaben, tebufenpyrad, tolfenpyrad
hydramethylnon
dicofol
Site-II Electron Transport Inhibitors
rotenone
Site-III Electron Transport Inhibitors
acequinocyl, fluacrypyrim
Microbial Disruptors of the Insect Gut Membrane
*Bacillus thuringiensis* strains
Lipid Synthesis Inhibitors
tetronic acids,
for example spirodiclofen, spiromesifen
tetramic acids,
for example spirotetramat, cis-3-(2,5-dimethylphenyl)-4-hydroxy-8-methoxy-1-azaspiro[4.5]dec-3-en-2-one
carboxamides,
for example flonicamid
octopaminergic agonists,
for example amitraz
Inhibitors of Magnesium-Stimulated ATPase,
propargite
nereistoxin analogues,
for example thiocyclam hydrogen oxalate, thiosultap-sodium
Ryanodin Receptor Agonists
benzoic acid dicarboxamides,
for example flubendiamid
anthranilamides,
for example rynaxypyr (3-bromo-N-{4-chloro-2-methyl-6-[(methylamino)carbonyl]phenyl}-1-(3-chloropyridin-2-yl)-1H-pyrazole-5-carboxamide)
Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.
Active Compounds with Unknown or Unspecific Mechanisms of Action
fumigants,
for example aluminium phosphide, methyl bromide, sulphuryl fluoride
antifeedants,
for example cryolite, flonicamid, pymetrozine
mite growth inhibitors,
for example clofentezine, etoxazole, hexythiazox
amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself. For increasing the activity, ammonium or phosphonium salts and/or penetration promoters can be added in particular.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injecting and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of from 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active compounds, such as phosphoric esters, carbamates, pyrethroids, neonicotinoids, growth regulators or active compounds from other known classes of insecticides.

They are used in aerosols, unpressurized spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, unenergized, or passive, evaporation systems, moth papers, moth bags and moth gels, as granules or dusts, in baits for scattering or in bait stations.

The preparation and use examples below provide an illustration of the invention, without restricting it.

PREPARATION EXAMPLES

Example 5-(3,5-Bis-trifluoromethylpyrazol-1-ylmethyl)-2-(3-chloropyridin-2-yl)-2H-pyrazole-3-carboxylic acid 4-chloro-2-methyl-6-methylcarbamoylphenyl amide (I-1-1)

First 300 mg (509 μmol) of 2-[5-(3,5-bistrifluoromethylpyrazol-1-ylmethyl)-2-(3-chloropyridin-2-yl)-2H-pyrazol-3-yl]-6-chloro-8-methyl-benzo[d][1,3]oxazin-4-one are introduced in 3.3 ml of tetrahydrofuran and this initial charge is admixed dropwise with 764 μl (1.53 mmol) of a 2 M solution of methylamine in tetrahydrofuran. The mixture is stirred at 50° C. for 1 h and then cooled, the solvent is removed in vacuo and the residue is purified on silica gel (cyclohexane/ethyl acetate=2:1→1:1).

Yield: 200 mg (log P: 3.67)

In analogy to the example given above (I-1-1) and also to the general description, the following compounds of the formula (I-1) are obtained.

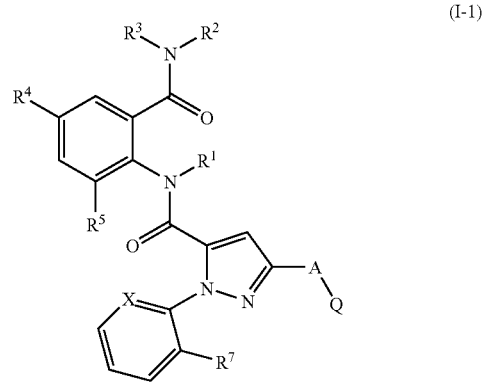

TABLE 1

| No. | R¹ | R² | R³ | R⁴ | R⁵ | A | Q | X | R⁷ | logP |
|---|---|---|---|---|---|---|---|---|---|---|
| I-1-2 | H | H | i-Pr | Cl | CH₃ | CH₂ | pyrazole with CF₃, CF₃ | N | Cl | 4.08 |
| I-1-3 | H | H | CH₃ | Cl | CH₃ | CH₂ | pyrazole with C₂F₅, C₂F₅ | N | Cl | 4.39 |

TABLE 1-continued

| No. | R¹ | R² | R³ | R⁴ | R⁵ | A | Q | X | R⁷ | logP |
|---|---|---|---|---|---|---|---|---|---|---|
| I-1-4 | H | H | CH₃ | Cl | CH₃ | CH₂ | 4-Cl-pyrazol-1-yl | N | Cl | 2.54 |
| I-1-5 | H | H | i-Pr | Cl | CH₃ | CH₂ | 3,5-bis(CF₃)-1,2,4-triazol-1-yl | N | Cl | 3.88 |
| I-1-6 | H | H | i-Pr | Cl | CH₃ | CH₂ | 3-CF₃-pyrazol-1-yl | N | Cl | 3.27 |
| I-1-7 | H | H | i-Pr | Cl | CH₃ | CH₂ | 4-F-pyrazol-1-yl | N | Cl | 2.70 |
| I-1-8 | H | H | i-Pr | Cl | CH₃ | CH₂ | 4-CN-pyrazol-1-yl | N | Cl | 2.57 |
| I-1-9 | H | H | i-Pr | Cl | CH₃ | CH₂ | pyrazol-1-yl | N | Cl | 2.45 |
| I-1-10 | H | H | i-Pr | Cl | CH₃ | CH₂ | 3,5-bis(CF₃)-pyrazol-1-yl | CH | Cl | 4.70 |
| I-1-11 | H | H | CH₃ | Cl | CH₃ | CH₂ | 3,5-bis(CF₃)-pyrazol-1-yl | CH | Cl | 4.12 |
| I-1-12 | H | H | i-Pr | Cl | CH₃ | CH₂ | 3-C₂F₅-4-C₂F₅-pyrazol-1-yl | N | Cl | 4.89 |

TABLE 1-continued

| No. | R¹ | R² | R³ | R⁴ | R⁵ | A | Q | X | R⁷ | logP |
|---|---|---|---|---|---|---|---|---|---|---|
| I-1-13 | H | H | i-Pr | Br | CH₃ | CH₂ | pyrazole with F₅C₂, C₂F₅ | N | Cl | 4.98 |
| I-1-14 | H | H | i-Pr | Cl | CH₃ | CH₂ | pyrazole with F₅C₂, I | N | Cl | 4.29 |
| I-1-15 | H | H | i-Pr | Cl | CH₃ | CH₂ | pyrazole with CF₃, Cl | N | Cl | 3.85 |
| I-1-16 | H | H | CH₃ | Cl | CH₃ | CH₂ | pyrazole with F₅C₂, I | N | Cl | 3.79 |
| I-1-17 | H | H | CH₃ | Cl | CH₃ | CH₂ | pyrazole with CF₃, Cl | N | Cl | 3.35 |
| I-1-18 | H | H | i-Pr | Cl | CH₃ | CH₂ | pyrazole with F₅C₂ | N | Cl | 3.75 |
| I-1-19 | H | H | CH₃ | Cl | CH₃ | CH₂ | pyrazole with F₅C₂ | N | Cl | 3.29 |
| I-1-20 | H | H | i-Pr | Br | CH₃ | CH₂ | pyrazole with CF₃, CF₃ | N | Cl | 4.16 |
| I-1-21 | H | H | i-Pr | Cl | CH₃ | CH₂ | 1,2,4-triazole | N | Cl | 2.02 |

TABLE 1-continued

| No. | $R^1$ | $R^2$ | $R^3$ | $R^4$ | $R^5$ | A | Q | X | $R^7$ | logP |
|---|---|---|---|---|---|---|---|---|---|---|
| I-1-22 | H | H | i-Pr | Br | $CH_3$ | $CH_2$ | triazole with $CF_3$, $CF_3$ | N | Cl | 3.91 |
| I-1-23 | H | H | i-Pr | Cl | $CH_3$ | $CH_2$ | triazole with $CF_3$, $C_2F_5$ | N | Cl | 4.25 |
| I-1-24 | H | H | $CH_3$ | Br | $CH_3$ | $CH_2$ | pyrazole with $C_2F_5$, $C_2F_5$ | N | Cl | 4.49 |
| I-1-25 | H | H | $CH_3$ | Br | $CH_3$ | $CH_2$ | pyrazole with $F_5C_2$, $C_2F_5$ | N | Cl | 4.39 |
| I-1-26 | H | H | $CH_3$ | Cl | $CH_3$ | $CH_2$ | triazole with $C_2F_5$, $C_2F_5$ | N | Cl | 4.17 |
| I-1-27 | H | H | $CH_3$ | Cl | $CH_3$ | $CH_2$ | pyrazole with $C_2F_5$, $C_2F_5$ | N | Cl | 4.45 |
| I-1-28 | H | H | i-Pr | Cl | $CH_3$ | $CH_2$ | pyrazole with $C_2F_5$, $CF_3$, F | N | Cl | 4.63 |
| I-1-29 | H | H | i-Pr | Cl | $CH_3$ | $CH_2$ | triazole with $C_2F_5$, $C_2F_5$ | N | Cl | 4.64 |
| I-1-30 | H | H | $CH_3$ | Cl | $CH_3$ | $CH_2$ | pyrazole with $F_5C_2$, Cl | N | Cl | 3.77 |

TABLE 1-continued
| No. | R¹ | R² | R³ | R⁴ | R⁵ | A | Q | X | R⁷ | logP |
|---|---|---|---|---|---|---|---|---|---|---|
| I-1-31 | H | H | i-Pr | Cl | CH₃ | CH₂ | 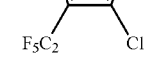 | N | Cl | 4.21 |
| I-1-32 | H | H | CH₂CN | Cl | CH₃ | CH₂ | 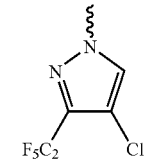 | N | Cl | 3.70 |
| I-1-33 | H | H | CH₂CN | Br | CH₃ | CH₂ | 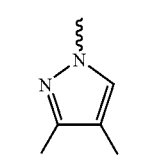 | N | Cl | 4.28 |
| I-1-34 | H | H | CH₃ | Cl | CH₃ | CH₂ | 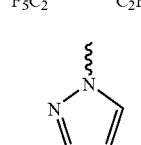 | N | Cl | 3.80 |
| I-1-35 | H | H | CH₃ | Cl | CH₃ | CH₂ | 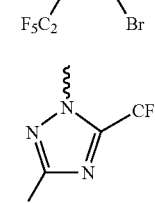 | N | Cl | 3.43 |
| I-1-36 | H | H | CH₃ | Br | CH₃ | CH₂ | 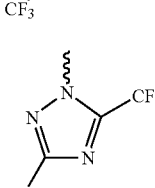 | N | Cl | 3.52 |
| I-1-37 | H | H | i-Pr | Br | CH₃ | CH₂ | 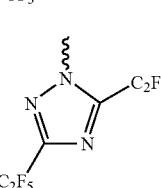 | N | Cl | 4.73 |
| I-1-38 | H | H | CH₃ | Cl | CH₃ | CH₂ | 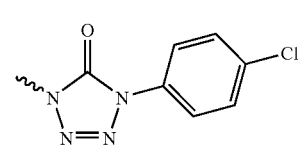 | N | Cl | 3.28 |
| I-1-39 | H | H | CH₃ | Br | CH₃ | CH₂ | 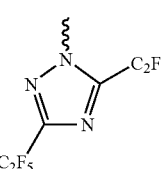 | N | Cl | 4.31 |

TABLE 1-continued

| No. | R¹ | R² | R³ | R⁴ | R⁵ | A | Q | X | R⁷ | logP |
|---|---|---|---|---|---|---|---|---|---|---|
| I-1-40 | H | H | i-Pr | Cl | CH₃ | CH₂ | 1H-1,2,4-triazol-1-yl with 3,5-bis(CF₃) | CCl | Cl | 4.58 |
| I-1-41 | H | H | CH₃ | Cl | CH₃ | CH₂ | 1H-1,2,4-triazol-1-yl with 3,5-bis(CF₃) | CCl | Cl | 4.13 |
| I-1-42 | H | H | CH₃ | Cl | CH₃ | CH₂ | 1H-pyrazol-1-yl with 4-CF₃ | N | Cl | 2.76 |
| I-1-43 | H | H | i-Pr | Cl | CH₃ | CH₂ | 1H-pyrazol-1-yl with 4-CF₃ | N | Cl | 3.20 |
| I-1-44 | H | H | CH₃ | Cl | CH₃ | CH₂ | 1H-pyrazol-1-yl with 3-CF₃ | N | Cl | 2.92 |
| I-1-45 | H | H | CH₃ | Cl | CH₃ | CH₂ | 1H-pyrazol-1-yl with 4-I | N | Cl | 2.67 |
| I-1-46 | H | H | c-Pr | Cl | CH₃ | CH₂ | 1H-pyrazol-1-yl with 3-C₂F₅, 4-C₂F₅ | N | Cl | 4.58 |
| I-1-47 | H | H | CH₂CN | Cl | CH₃ | CH₂ | 1H-pyrazol-1-yl with 3-C₂F₅, 4-C₂F₅ | N | Cl | 4.31 |
| I-1-48 | H | H | H | Cl | CH₃ | CH₂ | 1H-pyrazol-1-yl with 3-C₂F₅, 4-C₂F₅ | N | Cl | 4.15 |

TABLE 1-continued

| No. | R¹ | R² | R³ | R⁴ | R⁵ | A | Q | X | R⁷ | logP |
|---|---|---|---|---|---|---|---|---|---|---|
| I-1-49 | H | H | CH₂CN | Cl | CH₃ | CH₂ | 3,5-bis(CF₃)-1,2,4-triazol-1-yl | N | Cl | 3.97 |
| I-1-50 | H | H | H | Cl | CH₃ | CH₂ | 3,5-bis(CF₃)-1,2,4-triazol-1-yl | N | Cl | 3.88 |
| I-1-51 | H | H | i-Pr | Cl | CH₃ | CH₂ | 4-(2-chloro-6-methylphenyl)-5-oxo-tetrazol-1-yl | N | Cl | 3.52 |
| I-1-52 | H | H | c-Pr | Br | CH₃ | CH₂ | 3-C₂F₅-4-C₂F₅-pyrazol-1-yl | N | Cl | 4.59 |
| I-1-53 | H | H | H | Br | CH₃ | CH₂ | 3-C₂F₅-4-C₂F₅-pyrazol-1-yl | N | Cl | 4.17 |
| I-1-54 | H | H | c-Pr | Cl | CH₃ | CH₂ | 3,5-bis(CF₃)-1,2,4-triazol-1-yl | N | Cl | 3.61 |
| I-1-55 | H | H | CH₂CN | Cl | CH₃ | CH₂ | 3,5-bis(CF₃)-1,2,4-triazol-1-yl | N | Cl | 3.40 |
| I-1-56 | H | H | CH₂CN | Br | CH₃ | CH₂ | 3,5-bis(CF₃)-1,2,4-triazol-1-yl | N | Cl | 3.44 |

TABLE 1-continued

| No. | R¹ | R² | R³ | R⁴ | R⁵ | A | Q | X | R⁷ | logP |
|---|---|---|---|---|---|---|---|---|---|---|
| I-1-57 | H | H | c-Pr | Br | CH₃ | CH₂ | 1H-1,2,4-triazole-3,5-bis(CF₃) | N | Cl | 3.67 |
| I-1-58 | H | H | CH₃ | Br | CH₃ | CH₂ | 3,5-bis(CF₃)-pyrazol-1-yl | N | Cl | 3.76 |
| I-1-59 | H | H | CH₂CN | Br | CH₃ | CH₂ | 3,5-bis(CF₃)-pyrazol-1-yl | N | Cl | 3.65 |
| I-1-60 | H | H | c-Pr | Br | CH₃ | CH₂ | 3,5-bis(CF₃)-pyrazol-1-yl | N | Cl | 3.91 |
| I-1-61 | H | H | H | Br | CH₃ | CH₂ | 3,5-bis(CF₃)-pyrazol-1-yl | N | Cl | 3.53 |
| I-1-62 | H | H | CH₃ | Cl | CH₃ | CH₂ | 3-CF₃-4-I-pyrazol-1-yl | N | Cl | 3.41 |
| I-1-63 | H | H | i-Pr | Cl | CH₃ | CH₂ | 3-CF₃-4-I-pyrazol-1-yl | N | Cl | 3.85 |
| I-1-64 | H | H | CH₃ | Cl | CH₃ | CH₂ | 4-C₂F₅-pyrazol-1-yl | N | Cl | 3.21 |
| I-1-65 | H | H | i-Pr | Cl | CH₃ | CH₂ | 4-C₂F₅-pyrazol-1-yl | N | Cl | 3.67 |

TABLE 1-continued

| No. | R¹ | R² | R³ | R⁴ | R⁵ | A | Q | X | R⁷ | logP |
|---|---|---|---|---|---|---|---|---|---|---|
| I-1-66 | H | H | $CH_3$ | Cl | $CH_3$ | $CH_2$ | 4-Br-3-($CF_3$)-pyrazol-1-yl | N | Cl | 3.38 |
| I-1-67 | H | H | i-Pr | Cl | $CH_3$ | $CH_2$ | 4-Br-3-($CF_3$)-pyrazol-1-yl | N | Cl | 3.78 |
| I-1-68 | H | H | $CH_3$ | Br | $CH_3$ | $CH_2$ | 4-Br-3-($CF_3$)-pyrazol-1-yl | N | Cl | 3.46 |
| I-1-69 | H | H | i-Pr | Br | $CH_3$ | $CH_2$ | 4-Br-3-($CF_3$)-pyrazol-1-yl | N | Cl | 3.92 |
| I-1-70 | H | H | $CH_3$ | Br | $CH_3$ | $CH_2$ | 4-Cl-3-($C_2F_5$)-pyrazol-1-yl | N | Cl | 3.94 |
| I-1-71 | H | H | i-Pr | Br | $CH_3$ | $CH_2$ | 4-Cl-3-($C_2F_5$)-pyrazol-1-yl | N | Cl | 4.40 |
| I-1-72 | H | H | c-Pr | Br | $CH_3$ | $CH_2$ | 4-Cl-3-($C_2F_5$)-pyrazol-1-yl | N | Cl | 4.14 |
| I-1-73 | H | H | $CH_2CN$ | Br | $CH_3$ | $CH_2$ | 4-Cl-3-($C_2F_5$)-pyrazol-1-yl | N | Cl | 3.87 |

TABLE 1-continued
| No. | R¹ | R² | R³ | R⁴ | R⁵ | A | Q | X | R⁷ | logP |
|---|---|---|---|---|---|---|---|---|---|---|
| I-1-74 | H | H | H | Br | CH₃ | CH₂ | 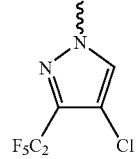 | N | Cl | 3.68 |
| I-1-75 | H | H | (S)—CH(CH₃)CH₂SCH₃ | Cl | CH₃ | CH₂ | 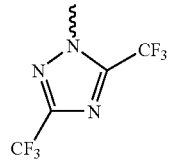 | N | Cl | 4.04 |
| I-1-76 | H | H | C(CH₃)₂CH₂SCH₃ | Cl | CH₃ | CH₂ | 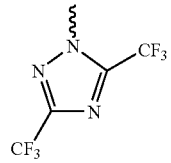 | N | Cl | 449 |
| I-1-77 | H | H | (S)—CH(CH₃)CH₂O(C=O)NHC₂H₅ | Cl | CH₃ | CH₂ | 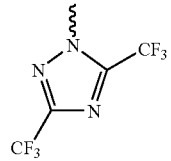 | N | Cl | 3.58 |
| I-1-78 | H | H | (S)—CH(CH₃)CH₂O(C=O)NHCH₃ | Cl | CH₃ | CH₂ | 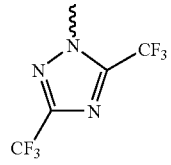 | N | Cl | 3.36 |
| I-1-79 | H | H | CH₂CN | Cl | CH₃ | CH₂ | 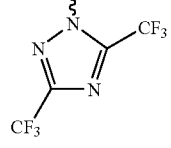 | N | Cl | 3.62 |
| I-1-80 | H | H | CH₃ | Br | CH₃ | CH₂ | 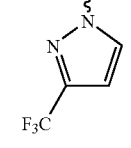 | N | Cl | 2.99 |
| I-1-81 | H | H | i-Pr | Br | CH₃ | CH₂ | 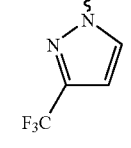 | N | Cl | 3.46 |
| I-1-82 | H | H | c-Pr | Br | CH₃ | CH₂ | 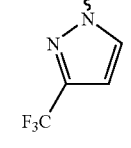 | N | Cl | 3.18 |

TABLE 1-continued

| No. | R¹ | R² | R³ | R⁴ | R⁵ | A | Q | X | R⁷ | logP |
|---|---|---|---|---|---|---|---|---|---|---|
| I-1-83 | H | H | H | Br | CH₃ | CH₂ | 3-(trifluoromethyl)-1H-pyrazol-1-yl | N | Cl | 2.75 |
| I-1-84 | H | H | (S)—CH(CH₃)CH₂SCH₃ | H | CH₃ | CH₂ | 3,5-bis(trifluoromethyl)-1H-1,2,4-triazol-1-yl | N | Cl | 3.62 |
| I-1-85 | H | H | CH₂CN | Br | CH₃ | CH₂ | 3-(trifluoromethyl)-1H-pyrazol-1-yl | N | Cl | 2.98 |
| I-1-86 | H | H | CH₃ | Cl | CH₃ | CH₂ | 3-(pentafluoroethyl)-5-(trifluoromethyl)-1H-1,2,4-triazol-1-yl | N | Cl | 3.78 |
| I-1-87 | H | H | (S)—CH(CH₃)CH₂SO₂CH₃ | H | CH₃ | CH₂ | 3,5-bis(trifluoromethyl)-1H-1,2,4-triazol-1-yl | N | Cl | 2.92 |
| I-1-88 | H | H | CH₃ | Cl | CH₃ | CH₂ | 4-[4-(trifluoromethyl)phenyl]-5-oxo-tetrazol-1-yl | N | Cl | 3.61 |
| I-1-89 | H | H | i-Pr | Cl | CH₃ | CH₂ | 4-[4-(trifluoromethyl)phenyl]-5-oxo-tetrazol-1-yl | N | Cl | 3.96 |
| I-1-90 | H | H | CH₃ | Cl | CH₃ | CH₂ | 4-[3,5-bis(trifluoromethyl)phenyl]-5-oxo-tetrazol-1-yl | N | Cl | 4.08 |
| I-1-91 | H | H | i-Pr | Cl | CH₃ | CH₂ | 4-[3,5-bis(trifluoromethyl)phenyl]-5-oxo-tetrazol-1-yl | N | Cl | 4.51 |

TABLE 1-continued

| No. | R¹ | R² | R³ | R⁴ | R⁵ | A | Q | X | R⁷ | logP |
|---|---|---|---|---|---|---|---|---|---|---|
| I-1-92 | H | H | (S)—CH(CH₃)CH₂SOCH₃ | H | CH₃ | CH₂ | 1,2,4-triazol-1-yl, 3,5-bis(CF₃) | N | Cl | 2.65 |
| I-1-93 | H | H | c-Pr | Br | CH₃ | CH₂ | pyrazol-1-yl, 3-CF₃, 4-Br | N | Cl | 3.69 |
| I-1-94 | H | H | H | Cl | CH₃ | CH₂ | 5-oxo-4-[3,5-bis(CF₃)phenyl]tetrazol-1-yl | N | Cl | 3.85 |
| I-1-95 | H | H | CH₂CN | Cl | CH₃ | CH₂ | 5-oxo-4-[3,5-bis(CF₃)phenyl]tetrazol-1-yl | N | Cl | 4.01 |
| I-1-96 | H | H | CH₃ | Cl | CH₃ | CH₂ | 5-oxo-4-(3,5-dichlorophenyl)tetrazol-1-yl | N | Cl | 3.90 |
| I-1-97 | H | H | CH₂CN | Br | CH₃ | CH₂ | pyrazol-1-yl, 3-CF₃, 4-Br | N | Cl | 3.45 |
| I-1-98 | H | H | C(CH₃)₂CH₂SCH₃ | Br | CH₃ | CH₂ | pyrazol-1-yl, 3-CF₃, 4-Br | N | Cl | 4.47 |
| I-1-99 | H | H | (S)—CH(CH₃)CH₂SCH₃ | Br | CH₃ | CH₂ | pyrazol-1-yl, 3-CF₃, 4-Br | N | Cl | 4.10 |

TABLE 1-continued

| No. | R¹ | R² | R³ | R⁴ | R⁵ | A | Q | X | R⁷ | logP |
|---|---|---|---|---|---|---|---|---|---|---|
| I-1-100 | H | H | H | Br | CH₃ | CH₂ | 4-Br-3-(CF₃)-pyrazol-1-yl | N | Cl | 3.24 |
| I-1-101 | H | H | (S)—CH(CH₃)CH₂SO₂CH₃ | Br | CH₃ | CH₂ | 4-Br-3-(CF₃)-pyrazol-1-yl | N | Cl | 3.32 |
| I-1-102 | H | H | CH₃ | Cl | CH₃ | CH₂ | 3-Cl-pyrazol-1-yl | N | Cl | 2.51 |
| I-1-103 | H | H | i-Pr | Cl | CH₃ | CH₂ | 3-Cl-pyrazol-1-yl | N | Cl | 2.96 |
| I-1-104 | H | H | CH₃ | Cl | CH₃ | CH₂ | 5-(4-CF₃-phenyl)-tetrazol-2-yl | N | Cl | 3.79 |
| I-1-105 | H | H | i-Pr | Cl | CH₃ | CH₂ | 5-(4-CF₃-phenyl)-tetrazol-2-yl | N | Cl | 4.14 |
| I-1-106 | H | H | H | Cl | CH₃ | CH₂ | 5-(4-CF₃-phenyl)-tetrazol-2-yl | N | Cl | 3.46 |
| I-1-107 | H | H | CH₂CN | Cl | CH₃ | CH₂ | 5-(4-CF₃-phenyl)-tetrazol-2-yl | N | Cl | 3.65 |
| I-1-108 | H | H | CH₃ | Cl | CH₃ | CH₂ | 4-(3-Cl-4-CF₃-phenyl)-5-oxo-tetrazol-1-yl | N | Cl | 3.90 |
| I-1-109 | H | H | CH₃ | Cl | CH₃ | CH₂ | 4-(2-Cl-4-CF₃-phenyl)-5-oxo-tetrazol-1-yl | N | Cl | 3.51 |

TABLE 1-continued

| No. | R¹ | R² | R³ | R⁴ | R⁵ | A | Q | X | R⁷ | logP |
|---|---|---|---|---|---|---|---|---|---|---|
| I-1-110 | H | H | CH₃ | Cl | CH₃ | CH₂ | 3,4-diiodopyrazol-1-yl | N | Cl | 3.13 |
| I-1-111 | H | H | i-Pr | Cl | CH₃ | CH₂ | 3,4-diiodopyrazol-1-yl | N | Cl | 3.58 |
| I-1-112 | H | H | CH₃ | Cl | CH₃ | CH₂ | 5-(3,5-bis(trifluoromethyl)phenyl)tetrazol-2-yl | N | Cl | 4.28 |
| I-1-113 | H | H | (S)—CH(CH₃)CH₂SOCH₃ | Br | CH₃ | CH₂ | 4-bromo-3-(trifluoromethyl)pyrazol-1-yl | N | Cl | 2.97 |
| I-1-114 | H | H | H | Cl | CH₃ | CH₂ | 5-(3,5-bis(trifluoromethyl)phenyl)tetrazol-2-yl | N | Cl | 4.03 |
| I-1-115 | H | H | i-Pr | Cl | CH₃ | CH₂ | 4-methyl-5-oxo-4,5-dihydrotetrazol-1-yl | N | Cl | 2.31 |
| I-1-116 | H | H | CH₃ | Cl | CH₃ | CH₂ | 4-methyl-5-oxo-3-(trifluoromethyl)-4,5-dihydro-1,2,4-triazol-1-yl | N | Cl | 2.44 |
| I-1-117 | H | H | i-Pr | Cl | CH₃ | CH₂ | 4-methyl-5-oxo-3-(trifluoromethyl)-4,5-dihydro-1,2,4-triazol-1-yl | N | Cl | 2.85 |
| I-1-118 | H | H | CH₃ | Cl | CH₃ | CH₂ | 5-oxo-4-phenyl-3-(trifluoromethyl)-4,5-dihydro-1,2,4-triazol-1-yl | N | Cl | 3.10 |

TABLE 1-continued

| No. | R¹ | R² | R³ | R⁴ | R⁵ | A | Q | X | R⁷ | logP |
|---|---|---|---|---|---|---|---|---|---|---|
| I-1-119 | H | H | i-Pr | Cl | CH₃ | CH₂ | 4-phenyl-5-(CF₃)-3-oxo-1,2,4-triazol-2-yl | N | Cl | 3.54 |
| I-1-120 | H | H | (S)—CH(CH₃)CH₂SO(=NH)CH₃ | Cl | CH₃ | CH₂ | 3,5-bis(CF₃)-1,2,4-triazol-1-yl | N | Cl | 2.75 |
| I-1-121 | H | H | C(CH₃)₂CH₂SO₂CH₃ | Br | CH₃ | CH₂ | 4-Br-3-(CF₃)-pyrazol-1-yl | N | Cl | 3.57 |
| I-1-122 | H | H | CH₃ | Cl | CH₃ | CH₂ | 4-(2,2,2-trifluoroethyl)-5-oxo-tetrazol-1-yl | N | Cl | 2.51 |
| I-1-123 | H | H | i-Pr | Cl | CH₃ | CH₂ | 4-(2,2,2-trifluoroethyl)-5-oxo-tetrazol-1-yl | N | Cl | 2.92 |
| I-1-124 | H | H | (S)—CH(CH₃)CH₂SCH₃ | | | | | N | Cl | 3.13 |
| I-1-125 | H | H | CH₃ | Cl | CH₃ | CH₂ | 3-Br-pyrazol-1-yl | N | Cl | 2.56 |
| I-1-126 | H | H | i-Pr | Cl | CH₃ | CH₂ | 4-cyclopropyl-5-(CF₃)-3-oxo-1,2,4-triazol-2-yl | N | Cl | 3.18 |
| I-1-127 | H | H | CH₃ | Cl | CH₃ | CH₂ | 4-cyclopropyl-5-(CF₃)-3-oxo-1,2,4-triazol-2-yl | N | Cl | 2.74 |
| I-1-128 | H | H | C(CH₃)₂CH₂SOCH₃ | Cl | CH₃ | CH₂ | 4-Br-3-(CF₃)-pyrazol-1-yl | N | Cl | 3.25 |

TABLE 1-continued

| No. | R¹ | R² | R³ | R⁴ | R⁵ | A | Q | X | R⁷ | logP |
|---|---|---|---|---|---|---|---|---|---|---|
| I-1-129 | H | H | (S)—CH(CH₃)CH₂SO₂CH₃ | Cl | CH₃ | CH₃ | 1H-1,2,4-triazol-1-yl, 3,5-bis(CF₃) | N | Cl | 3.27 |
| I-1-130 | H | H | (S)—CH(CH₃)CH₂SCH₃ | Cl | CH₃ | CH₂ | 1H-pyrazol-1-yl, 4-Br, 3-CF₃ | N | Cl | 4.11 |
| I-1-131 | H | H | C(CH₃)₂CH₂SCH₃ | Cl | CH₃ | CH₂ | 1H-pyrazol-1-yl, 4-Br, 3-CF₃ | N | Cl | 4.48 |
| I-1-132 | H | H | CH₃ | Cl | CH₃ | CH₂ | 1H-imidazol-1-yl, 5-CF₃ | N | Cl | 2.39 |
| I-1-133 | H | H | i-Pr | Cl | CH₃ | CH₂ | 1H-imidazol-1-yl, 5-CF₃ | N | Cl | 2.77 |
| I-1-134 | H | H | C(CH₃)₂CH₂SCH₃ | Br | CH₃ | CH₂ | 1H-1,2,4-triazol-1-yl, 3,5-bis(CF₃) | N | Cl | 4.63 |
| I-1-135 | H | H | (S)—CH(CH₃)CH₂SCH₃ | Br | CH₃ | CH₂ | 1H-1,2,4-triazol-1-yl, 3,5-bis(CF₃) | N | Cl | 4.24 |
| I-1-136 | H | H | C(CH₃)₂CH₂SOCH₃ | Cl | CH₃ | CH₂ | 1H-pyrazol-1-yl, 4-Br, 3-CF₃ | N | Cl | 3.23 |

TABLE 1-continued

| No. | R¹ | R² | R³ | R⁴ | R⁵ | A | Q | X | R⁷ | logP |
|---|---|---|---|---|---|---|---|---|---|---|
| I-1-137 | H | H | C(CH₃)₂CH₂SOCH₃ | Cl | CH₃ | CH₂ | 3,5-bis(CF₃)-1,2,4-triazol-1-yl | N | Cl | 3.22 |
| I-1-138 | H | H | (S)—CH(CH₃)CH₂SOCH₃ | Cl | CH₃ | CH₂ | 4-Br-3-CF₃-pyrazol-1-yl | N | Cl | 2.91 |
| I-1-139 | H | H | C(CH₃)₂CH₂SO₂CH₃ | Cl | CH₃ | CH₂ | 3,5-bis(CF₃)-1,2,4-triazol-1-yl | N | Cl | 3.50 |
| I-1-140 | H | H | (S)—CH(CH₃)CH₂SOCH₃ | Br | CH₃ | CH₂ | 3,5-bis(CF₃)-1,2,4-triazol-1-yl | N | Cl | 3.05 |
| I-1-141 | H | H | (S)—CH(CH₃)CH₂SO₂CH₃ | Cl | CH₃ | CH₂ | 4-Br-3-CF₃-pyrazol-1-yl | N | Cl | 3.26 |
| I-1-142 | H | H | C(CH₃)₂CH₂SO₂CH₃ | Br | CH₃ | CH₂ | 3,5-bis(CF₃)-1,2,4-triazol-1-yl | N | Cl | 3.67 |
| I-1-143 | H | H | C(CH₃)₂CH₂SOCH₃ | Br | CH₃ | CH₂ | 3,5-bis(CF₃)-1,2,4-triazol-1-yl | N | Cl | 3.20 |
| I-1-144 | H | H | C(CH₃)₂CH₂SOCH₃ | Br | CH₃ | CH₂ | 3,5-bis(CF₃)-1,2,4-triazol-1-yl | N | Cl | 3.38 |
| I-1-145 | H | H | C(CH₃)₂CH₂SO₂CH₃ | Cl | CH₃ | CH₂ | 4-Br-3-CF₃-pyrazol-1-yl | N | Cl | 3.56 |

TABLE 1-continued

| No. | R¹ | R² | R³ | R⁴ | R⁵ | A | Q | X | R⁷ | logP |
|---|---|---|---|---|---|---|---|---|---|---|
| I-1-146 | H | H | (S)—CH(CH₃)CH₂SO₂CH₃ | Br | CH₃ | CH₂ | 1,2,4-triazole-1-yl with 3,5-bis(CF₃) | N | Cl | 3.36 |
| I-1-147 | H | H | (S)—CH(CH₃)CH₂SOCH₃ | Cl | CH₃ | CH₂ | 1,2,4-triazole-1-yl with 3,5-bis(CF₃) | N | Cl | 2.95 |
| I-1-148 | H | H | CH₃ | Cl | CH₃ | CH₂ | tetrazolyl-(6-chloropyridin-3-yl) | N | Cl | 2.91 |
| I-1-149 | H | H | i-Pr | Cl | CH₃ | CH₂ | tetrazolyl-(6-chloropyridin-3-yl) | N | Cl | 3.41 |
| I-1-150 | H | H | CH₃ | Cl | CH₃ | CH₂ | tetrazolyl-(4-bromophenyl) | N | Cl | 3.70 |
| I-1-151 | H | H | i-Pr | Cl | CH₃ | CH₂ | tetrazolyl-(4-bromophenyl) | N | Cl | 4.20 |
| I-1-152 | H | H | (S)—CH(CH₃)CH₂SCH₃ | Cl | CH₃ | CH₂ | tetrazolyl-(4-bromophenyl) | N | Cl | 4.41 |
| I-1-153 | H | H | CH₃ | Cl | CH₃ | CH₂ | tetrazolyl-(4-chlorophenyl) | N | Cl | 3.07 |
| I-1-154 | H | H | i-Pr | Cl | CH₃ | CH₂ | tetrazolyl-(4-chlorophenyl) | N | Cl | 3.56 |
| I-1-155 | H | H | CH₃ | Cl | CH₃ | CH₂ | tetrazolyl-(2,6-dichloropyridin-4-yl) | N | Cl | 3.69 |

TABLE 1-continued
| No. | R¹ | R² | R³ | R⁴ | R⁵ | A | Q | X | R⁷ | logP |
|---|---|---|---|---|---|---|---|---|---|---|
| I-1-156 | H | H | i-Pr | Cl | CH₃ | CH₂ | 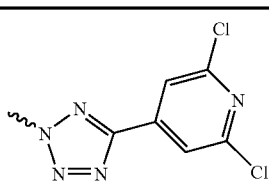 | N | Cl | 4.17 |
| I-1-157 | H | H | (S)—CH(CH₃)CH₂SCH₃ | Cl | CH₃ | CH₂ | 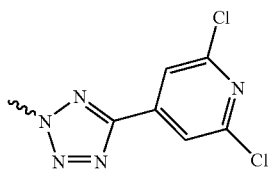 | N | Cl | 4.36 |
| I-1-158 | H | H | (S)—CH(CH₃)CH₂SCH₃ | Cl | CH₃ | CH₂ | 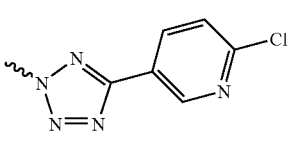 | N | Cl | 3.67 |
| I-1-159 | H | H | (S)—CH(CH₃)CH₂SCH₃ | Cl | CH₃ | CH₂ | 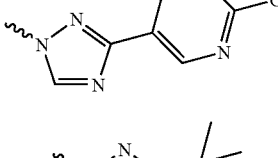 | N | Cl | 3.78 |
| I-1-160 | H | H | CH₃ | Cl | CH₃ | CH₂ | 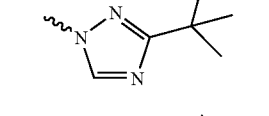 | N | Cl | 2.39 |
| I-1-161 | H | H | i-Pr | Cl | CH₃ | CH₂ | 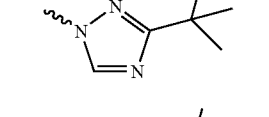 | N | Cl | 2.87 |
| I-1-162 | H | H | (S)—CH(CH₃)CH₂SCH₃ | Cl | CH₃ | CH₂ | 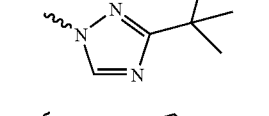 | N | Cl | 3.10 |
| I-1-163 | H | H | CH₃ | Cl | CH₃ | CH₂ | 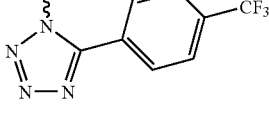 | N | Cl | 3.15 |
| I-1-164 | H | H | NH[S(=O)₂]N(CH₃)₂ | Cl | CH₃ | CH₂ | 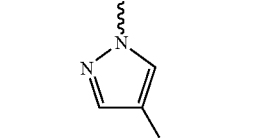 | N | Cl | 3.35 |
| I-1-165 | H | H | CH₃ | Cl | CH₃ | CH₂ | 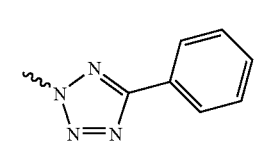 | N | Cl | 3.09 |
| I-1-166 | H | H | i-Pr | Cl | CH₃ | CH₂ | 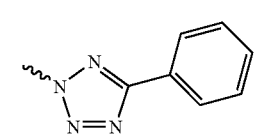 | N | Cl | 3.60 |

TABLE 1-continued

| No. | R¹ | R² | R³ | R⁴ | R⁵ | A | Q | X | R⁷ | logP |
|---|---|---|---|---|---|---|---|---|---|---|
| I-1-167 | H | =S(i-Pr)₂ | | Cl | CH₃ | CH₂ | 1,2,4-triazol-1-yl with 3-CF₃ and 5-CF₃ | N | Cl | 4.44 |
| I-1-168 | H | H | i-Pr | Cl | CH₃ | CH₂ | tetrazol-5(4H)-one, 4-(4-chlorophenyl) | N | Cl | 3.79 |
| I-1-169 | H | H | i-Pr | CN | CH₃ | CH₂ | pyrazol-1-yl, 3-C₂F₅, 4-C₂F₅ | N | Cl | 4.55 |
| I-1-170 | H | H | CH₃ | CN | CH₃ | CH₂ | pyrazol-1-yl, 3-C₂F₅, 4-C₂F₅ | N | Cl | 4.08 |
| I-1-171 | H | H | CH₃ | CN | CH₃ | CH₂ | pyrazol-1-yl, 3-C₂F₅, 4-Cl | N | Cl | 3.44 |
| I-1-172 | H | H | i-Pr | CN | CH₃ | CH₂ | pyrazol-1-yl, 3-C₂F₅, 4-Cl | N | Cl | 3.87 |
| I-1-173 | H | H | c-Pr | CN | CH₃ | CH₂ | pyrazol-1-yl, 3-C₂F₅, 4-Cl | N | Cl | 3.59 |
| I-1-174 | H | H | H | CN | CH₃ | CH₂ | pyrazol-1-yl, 3-C₂F₅, 4-Cl | N | Cl | 3.20 |
| I-1-175 | H | H | CH₂CN | CN | CH₃ | CH₂ | pyrazol-1-yl, 3-C₂F₅, 4-Cl | N | Cl | 3.40 |

TABLE 1-continued

| No. | R¹ | R² | R³ | R⁴ | R⁵ | A | Q | X | R⁷ | logP |
|---|---|---|---|---|---|---|---|---|---|---|
| I-1-176 | H | H | CH₃ | CN | CH₃ | CH₂ | 3,5-bis(CF₃)-1,2,4-triazol-1-yl | N | Cl | 3.11 |
| I-1-177 | H | H | i-Pr | CN | CH₃ | CH₂ | 3,5-bis(CF₃)-1,2,4-triazol-1-yl | N | Cl | 3.53 |
| I-1-178 | H | H | c-Pr | CN | CH₃ | CH₂ | 3,5-bis(CF₃)-1,2,4-triazol-1-yl | N | Cl | 3.31 |
| I-1-179 | H | H | H | CN | CH₃ | CH₂ | 3,5-bis(CF₃)-1,2,4-triazol-1-yl | N | Cl | 2.91 |
| I-1-180 | H | H | CH₂CN | CN | CH₃ | CH₂ | 3,5-bis(CF₃)-1,2,4-triazol-1-yl | N | Cl | 3.11 |
| I-1-181 | H | H | CH₃ | CN | CH₃ | CH₂ | 3-(CF₃)-pyrazol-1-yl | N | Cl | 2.57 |
| I-1-182 | H | H | i-Pr | CN | CH₃ | CH₂ | 3-(CF₃)-pyrazol-1-yl | N | Cl | 2.96 |
| I-1-183 | H | H | c-Pr | CN | CH₃ | CH₂ | 3-(CF₃)-pyrazol-1-yl | N | Cl | 2.75 |
| I-1-184 | H | H | H | CN | CH₃ | CH₂ | 3-(CF₃)-pyrazol-1-yl | N | Cl | 2.42 |

TABLE 1-continued

| No. | R¹ | R² | R³ | R⁴ | R⁵ | A | Q | X | R⁷ | logP |
|---|---|---|---|---|---|---|---|---|---|---|
| I-1-185 | H | H | CH$_2$CN | CN | CH$_3$ | CH$_2$ | 3-CF$_3$-pyrazol-1-yl | N | Cl | 2.62 |
| I-1-186 | H | H | CH$_3$ | CN | CH$_3$ | CH$_2$ | 3,5-bis(CF$_3$)-pyrazol-1-yl | N | Cl | 3.35 |
| I-1-187 | H | H | i-Pr | CN | CH$_3$ | CH$_2$ | 3,5-bis(CF$_3$)-pyrazol-1-yl | N | Cl | 3.80 |
| I-1-188 | H | H | c-Pr | CN | CH$_3$ | CH$_2$ | 3,5-bis(CF$_3$)-pyrazol-1-yl | N | Cl | 3.56 |
| I-1-189 | H | H | H | CN | CH$_3$ | CH$_2$ | 3,5-bis(CF$_3$)-pyrazol-1-yl | N | Cl | 3.15 |
| I-1-190 | H | H | CH$_2$CN | CN | CH$_3$ | CH$_2$ | 3,5-bis(CF$_3$)-pyrazol-1-yl | N | Cl | 3.28 |
| I-1-191 | H | H | c-Pr | CN | CH$_3$ | CH$_2$ | 3-C$_2$F$_5$-4-C$_2$F$_5$-pyrazol-1-yl | N | Cl | 4.29 |
| I-1-192 | H | H | H | CN | CH$_3$ | CH$_2$ | 3-C$_2$F$_5$-4-C$_2$F$_5$-pyrazol-1-yl | N | Cl | 3.91 |

TABLE 1-continued

| No. | R¹ | R² | R³ | R⁴ | R⁵ | A | Q | X | R⁷ | logP |
|---|---|---|---|---|---|---|---|---|---|---|
| I-1-193 | H | H | CH₂CN | CN | CH₃ | CH₂ | pyrazole, 3-C₂F₅, 4-C₂F₅ | N | Cl | 4.04 |
| I-1-194 | H |  | cyclopentyl-NH₂ | CN | CH₃ | CH₂ | pyrazole, 3-C₂F₅, 4-Cl | N | Cl | 2.18 |
| I-1-195 | H | H | (S)—CH(CH₃)CH₂SCH₃ | F | CH₃ | CH₂ | pyrazole, 3-C₂F₅, 4-Cl | N | Cl | 4.13 |
| I-1-196 | H | H | furan-2-yl | F | CH₃ | CH₂ | pyrazole, 3-C₂F₅, 4-Cl | N | Cl | 3.90 |
| I-1-197 | H | H | bicyclo[4.1.0]heptyl | CN | CH₃ | CH₂ | pyrazole, 3-C₂F₅, 4-Cl | N | Cl | 4.50 |
| I-1-198 | H | H | cyclopropyl-CH₂OH | CN | CH₃ | CH₂ | pyrazole, 3-C₂F₅, 4-Cl | N | Cl | 3.11 |
| I-1-199 | H | H | bicyclo[4.1.0]heptyl | F | CH₃ | CH₂ | pyrazole, 3-C₂F₅, 4-Cl | N | Cl | 4.55 |
| I-1-200 | H |  | cyclopentyl-NH₂ | F | CH₃ | CH₂ | pyrazole, 3-C₂F₅, 4-Cl | N | Cl | 2.19 |
| I-1-201 | H | H | furan-2-yl | Cl | CH₃ | CH₂ | pyrazole, 3-C₂F₅, 4-Cl | N | Cl | 4.21 |

TABLE 1-continued
| No. | R¹ | R² | R³ | R⁴ | R⁵ | A | Q | X | R⁷ | logP |
|---|---|---|---|---|---|---|---|---|---|---|
| I-1-202 | H | H | 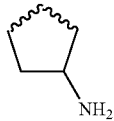 | Cl | $CH_3$ | $CH_2$ | 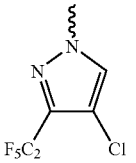 | N | Cl | 2.30 |
| I-1-203 | H | H | 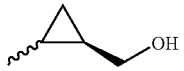 | F | $CH_3$ | $CH_2$ | 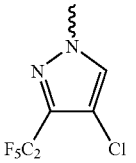 | N | Cl | 3.14 |
| I-1-204 | H | H | (S)—CH(CH₃)CH₂SO₂CH₃ | F | $CH_3$ | $CH_2$ | 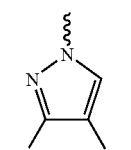 | N | Cl | 3.34 |
| I-1-205 | H | H |  | Cl | $CH_3$ | $CH_2$ | 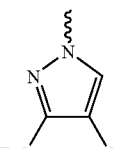 | N | Cl | 4.88 |
| I-1-206 | H | H | (S)—CH(CH₃)CH₂SCH₃ | Cl | $CH_3$ | $CH_2$ | 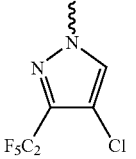 | N | Cl | 4.41 |
| I-1-207 | H | H | 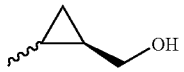 | Cl | $CH_3$ | $CH_2$ | 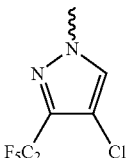 | N | Cl | 3.37 |
| I-1-208 | H | H | 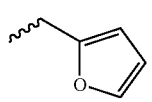 | CN | $CH_3$ | $CH_2$ | 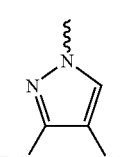 | N | Cl | 3.90 |
| I-1-209 | H | H | (S)—CH(CH₃)CH₂SCH₃ | CN | $CH_3$ | $CH_2$ | 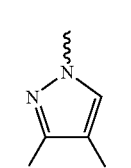 | N | Cl | 4.05 |

TABLE 1-continued
| No. | R¹ | R² | R³ | R⁴ | R⁵ | A | Q | X | R⁷ | logP |
|---|---|---|---|---|---|---|---|---|---|---|
| I-1-210 | H | H | (S)—CH(CH₃)CH₂SO₂CH₃ | CN | CH₃ | CH₂ | 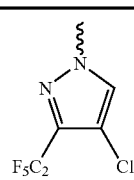 | N | Cl | 3.34 |
| I-1-211 | H | H | (S)—CH(CH₃)CH₂SOCH₃ | CN | CH₃ | CH₂ | 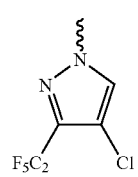 | N | Cl | 3.02 |
| I-1-212 | H | H | (S)—CH(CH₃)CH₂SOCH₃ | Cl | CH₃ | CH₂ | 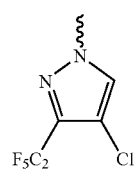 | N | Cl | 3.25 |
| I-1-213 | H | H | (S)—CH(CH₃)CH₂SO₂CH₃ | Cl | CH₃ | CH₂ | 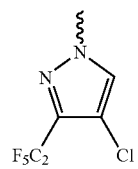 | N | Cl | 3.60 |
| I-1-214 | H | H | 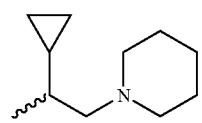 | Cl | CH₃ | CH₂ | 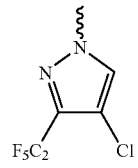 | N | Cl | 2.77 |
| I-1-215 | H | H | 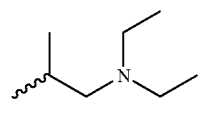 | Cl | CH₃ | CH₂ | 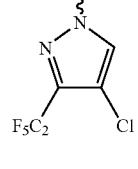 | N | Cl | 2.62 |
| I-1-216 | H | H | (S)—CH(CH₃)CH₂SOCH₃ | F | CH₃ | CH₂ | 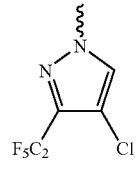 | N | Cl | 3.03 |
| I-1-217 | H | H | i-Pr | F | CH₃ | CH₂ | 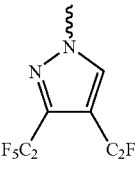 | N | Cl | 4.47 |
| I-1-218 | H | H | i-Pr | F | CH₃ | CH₂ | 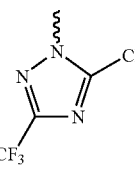 | N | Cl | 3.55 |

TABLE 1-continued

| No. | R¹ | R² | R³ | R⁴ | R⁵ | A | Q | X | R⁷ | logP |
|---|---|---|---|---|---|---|---|---|---|---|
| I-1-219 | H | H | $CH_3$ | F | $CH_3$ | $CH_2$ | 1,2,4-triazol-1-yl with $CF_3$ at 3 and 5 | N | Cl | 3.12 |
| I-1-220 | H | H | $CH_3$ | F | $CH_3$ | $CH_2$ | pyrazol-1-yl with $C_2F_5$ at 3 and 4 | N | Cl | 4.06 |
| I-1-221 | H | H | $CH_3$ | F | $CH_3$ | $CH_2$ | pyrazol-1-yl with $CF_3$ at 3 and 5 | N | Cl | 3.32 |
| I-1-222 | H | H | $CH_3$ | F | $CH_3$ | $CH_2$ | pyrazol-1-yl with $CF_3$ at 3 | N | Cl | 2.58 |
| I-1-223 | H | H | $CH_3$ | F | $CH_3$ | $CH_2$ | pyrazol-1-yl with $C_2F_5$ at 3 and Cl at 4 | N | Cl | 3.47 |
| I-1-224 | H | H | i-Pr | F | $CH_3$ | $CH_2$ | pyrazol-1-yl with $C_2F_5$ at 3 and Cl at 4 | N | Cl | 3.89 |
| I-1-225 | H | H | i-Pr | F | $CH_3$ | $CH_2$ | pyrazol-1-yl with $CF_3$ at 3 and 5 | N | Cl | 3.77 |
| I-1-226 | H | H | i-Pr | F | $CH_3$ | $CH_2$ | pyrazol-1-yl with $CF_3$ at 3 | N | Cl | 3.00 |

TABLE 1-continued

| No. | R¹ | R² | R³ | R⁴ | R⁵ | A | Q | X | R⁷ | logP |
|---|---|---|---|---|---|---|---|---|---|---|
| I-1-227 | H | H | CH₃ | I | CH₃ | CH₂ | 3,5-bis(CF₃)-pyrazol-1-yl | N | Cl | 3.87 |
| I-1-228 | H | H | C₂H₅ | I | CH₃ | CH₂ | 3,5-bis(CF₃)-pyrazol-1-yl | N | Cl | 4.06 |
| I-1-229 | H | H | n-Pr | I | CH₃ | CH₂ | 3,5-bis(CF₃)-pyrazol-1-yl | N | Cl | 4.33 |
| I-1-230 | H | H | i-Pr | I | CH₃ | CH₂ | 3,5-bis(CF₃)-pyrazol-1-yl | N | Cl | 4.29 |
| I-1-231 | H | H | c-Pr | I | CH₃ | CH₂ | 3,5-bis(CF₃)-pyrazol-1-yl | N | Cl | 4.01 |
| I-1-232 | H | H | CH₂CF₃ | I | CH₃ | CH₂ | 3,5-bis(CF₃)-pyrazol-1-yl | N | Cl | 5.28 |
| I-1-233 | H | H | CH(CH₃)(c-Pr) | I | CH₃ | CH₂ | 3,5-bis(CF₃)-pyrazol-1-yl | N | Cl | 4.55 |
| I-1-234 | H | H | H | I | CH₃ | CH₂ | 3,5-bis(CF₃)-pyrazol-1-yl | N | Cl | 3.56 |
| I-1-235 | H | H | CH₂(c-Pr) | I | CH₃ | CH₂ | 3,5-bis(CF₃)-pyrazol-1-yl | N | Cl | 4.34 |

TABLE 1-continued

| No. | R¹ | R² | R³ | R⁴ | R⁵ | A | Q | X | R⁷ | logP |
|---|---|---|---|---|---|---|---|---|---|---|
| I-1-236 | H | H | dicyclopropylmethyl | I | CH₃ | CH₂ | 3,5-bis(CF₃)-pyrazol-1-yl | N | Cl | 4.80 |
| I-1-237 | H | H | CH₃ | I | CH₃ | CH₂ | 3,5-bis(CF₃)-1,2,4-triazol-1-yl | N | Cl | 3.60 |
| I-1-238 | H | H | i-Pr | I | CH₃ | CH₂ | 3,5-bis(CF₃)-1,2,4-triazol-1-yl | N | Cl | 4.06 |
| I-1-239 | H | H | CH₃ | I | CH₃ | CH₂ | 3-C₂F₅-4-C₂F₅-pyrazol-1-yl | N | Cl | 4.51 |
| I-1-240 | H | H | i-Pr | I | CH₃ | CH₂ | 3-C₂F₅-4-C₂F₅-pyrazol-1-yl | N | Cl | 4.96 |
| I-1-241 | H | H | CH₂CN | I | CH₃ | CH₂ | 3,5-bis(CF₃)-pyrazol-1-yl | N | Cl | 3.73 |
| I-1-242 | H | H | i-Pr | I | CH₃ | CH₂ | 3-C₂F₅-4-Cl-pyrazol-1-yl | N | Cl | 4.40 |
| I-1-243 | H | H | CH₃ | I | CH₃ | CH₂ | 3-C₂F₅-4-Cl-pyrazol-1-yl | N | Cl | 3.96 |

TABLE 1-continued

| No. | R¹ | R² | R³ | R⁴ | R⁵ | A | Q | X | R⁷ | logP |
|---|---|---|---|---|---|---|---|---|---|---|
| I-1-244 | H | H | C₂H₅ | I | CH₃ | CH₂ | 1H-1,2,4-triazole-3,5-bis(CF₃) | N | Cl | 3.83 |
| I-1-245 | H | H | CH₂CN | I | CH₃ | CH₂ | 1H-1,2,4-triazole-3,5-bis(CF₃) | N | Cl | 3.53 |
| I-1-246 | H | H | CH₂CN | I | CH₃ | CH₂ | 3-(C₂F₅)-4-Cl-pyrazol-1-yl | N | Cl | 3.85 |
| I-1-247 | H | H | CH₃ | I | CH₃ | CH₂ | 3-CF₃-pyrazol-1-yl | N | Cl | 3.05 |
| I-1-248 | H | H | i-Pr | I | CH₃ | CH₂ | 3-CF₃-pyrazol-1-yl | N | Cl | 3.51 |
| I-1-249 | H | H | c-Pr | I | CH₃ | CH₂ | 3-CF₃-pyrazol-1-yl | N | Cl | 3.27 |
| I-1-250 | H | H | C₂H₅ | I | CH₃ | CH₂ | 3-CF₃-pyrazol-1-yl | N | Cl | 3.28 |
| I-1-251 | H | H | CH₂CN | I | CH₃ | CH₂ | 3-CF₃-pyrazol-1-yl | N | Cl | 3.04 |
| I-1-252 | H | H | c-Pr | I | CH₃ | CH₂ | 1H-1,2,4-triazole-3,5-bis(CF₃) | N | Cl | 3.81 |

TABLE 1-continued

| No. | R¹ | R² | R³ | R⁴ | R⁵ | A | Q | X | R⁷ | logP |
|---|---|---|---|---|---|---|---|---|---|---|
| I-1-253 | H | H | cyclopropylmethyl | I | CH₃ | CH₂ | 3,5-bis(CF₃)-1H-1,2,4-triazol-1-yl | N | Cl | 4.13 |
| I-1-254 | H | H | cyclopropylmethyl | I | CH₃ | CH₂ | 4-Cl-3-(C₂F₅)-1H-pyrazol-1-yl | N | Cl | 4.47 |
| I-1-255 | H | H | cyclopropylmethyl | I | CH₃ | CH₂ | 3-(CF₃)-1H-pyrazol-1-yl | N | Cl | 3.60 |
| I-1-256 | H | CH₃ | CH₃ | I | CH₃ | CH₂ | 3,5-bis(CF₃)-1H-pyrazol-1-yl | N | Cl | 3.84 |
| I-1-257 | H | H | CH₃ | Cl | CH₃ | CH₂ | 3,5-bis(CHF₂)-4-NO₂-1H-pyrazol-1-yl | N | Cl | 2.92 |
| I-1-258 | H | H | i-Pr | Cl | CH₃ | CH₂ | 3,5-bis(CHF₂)-4-NO₂-1H-pyrazol-1-yl | N | Cl | 3.32 |
| I-1-259 | H | H | i-Pr | Cl | Cl | CH₂ | 3,5-bis(CHF₂)-4-NO₂-1H-pyrazol-1-yl | N | Cl | 3.27 |
| I-1-260 | H | H | c-Pr | Cl | CH₃ | CH₂ | 3,5-bis(CHF₂)-4-NO₂-1H-pyrazol-1-yl | N | Cl | 3.12 |

TABLE 1-continued
| No. | R¹ | R² | R³ | R⁴ | R⁵ | A | Q | X | R⁷ | logP |
|---|---|---|---|---|---|---|---|---|---|---|
| I-1-261 | H | H | c-Pr | Cl | Cl | CH₂ | 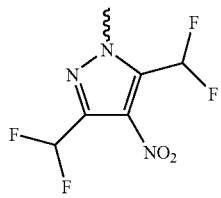 | N | Cl | 3.08 |
| I-1-262 | H | H | i-Pr | Cl | CH₃ | CH₂ | 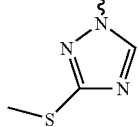 | N | Cl | 2.31 |
| I-1-263 | H | H | c-Pr | Cl | CH₃ | CH₂ | 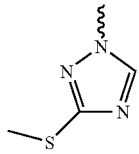 | N | Cl | 2.13 |
| I-1-264 | H | H |  | Cl | CH₃ | CH₂ | 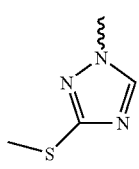 | N | Cl | 2.39 |
| I-1-265 | H | H | CH₃ | Cl | CH₃ | CH₂ | 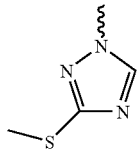 | N | Cl | 1.94 |
| I-1-266 | H | H | CH₃ | Cl | Cl | CH₂ | 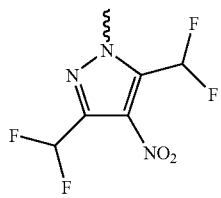 | N | Cl | 2.99 |
| I-1-267 | H | H | i-Pr | I | CH₃ | CH₂ | 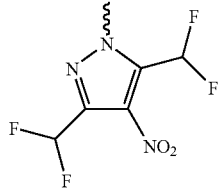 | N | Cl | 3.67 |
| I-1-268 | H | H | c-Pr | I | CH₃ | CH₂ | 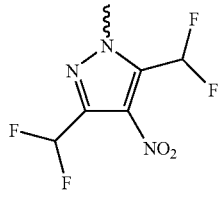 | N | Cl | 3.44 |

TABLE 1-continued

| No. | R¹ | R² | R³ | R⁴ | R⁵ | A | Q | X | R⁷ | logP |
|---|---|---|---|---|---|---|---|---|---|---|
| I-1-269 | H | H | i-Pr | Cl | CH₃ | CH₂ | 1,5-dimethyl-4-bromo-pyrazol-1-yl | N | Cl | 3.4 |
| I-1-270 | H | H | CH₃ | Cl | CH₃ | CH₂ | 1,5-dimethyl-4-bromo-pyrazol-1-yl | N | Cl | 2.95 |
| I-1-271 | H | H | c-Pr | Cl | CH₃ | CH₂ | 1,5-dimethyl-4-bromo-pyrazol-1-yl | N | Cl | 3.17 |
| I-1-272 | H | H | H | I | CH₃ | CH₂ | 3,5-bis(CF₃)-1,2,4-triazol-1-yl | N | Cl | 3.38 |
| I-1-273 | H | H | H | I | CH₃ | CH₂ | 3-CF₃-pyrazol-1-yl | N | Cl | 2.84 |
| I-1-274 | H | H | C₂H₅ | I | CH₃ | CH₂ | 3-C₂F₅-4-C₂F₅-pyrazol-1-yl | N | Cl | 4.74 |
| I-1-275 | H | H | c-Pr | I | CH₃ | CH₂ | 3-C₂F₅-4-C₂F₅-pyrazol-1-yl | N | Cl | 4.71 |
| I-1-276 | H | H | c-Pr | I | CH₃ | CH₂ | 3-C₂F₅-4-Cl-pyrazol-1-yl | N | Cl | 4.15 |
| I-1-277 | H | H | C₂H₅ | I | CH₃ | CH₂ | 3-C₂F₅-4-Cl-pyrazol-1-yl | N | Cl | 4.17 |

TABLE 1-continued

| No. | R¹ | R² | R³ | R⁴ | R⁵ | A | Q | X | R⁷ | logP |
|---|---|---|---|---|---|---|---|---|---|---|
| I-1-278 | H | H | CH₃ | I | CH₃ | CH₂ | 3,5-bis(difluoromethyl)-4-nitro-pyrazol-1-yl | N | Cl | 3.25 |
| I-1-279 | H | H | cyclopentyl | I | CH₃ | CH₂ | 3,5-bis(trifluoromethyl)-1,2,4-triazol-1-yl | N | Cl | 4.47 |
| I-1-280 | H | H | cyclododecyl | I | CH₃ | CH₂ | 3,5-bis(trifluoromethyl)-1,2,4-triazol-1-yl | N | Cl | 6.56 |
| I-1-281 | H | H | cyclohexyl | I | CH₃ | CH₂ | 3,5-bis(trifluoromethyl)-1,2,4-triazol-1-yl | N | Cl | 4.54 |
| I-1-282 | H | H | cyclobutyl | I | CH₃ | CH₂ | 3,5-bis(trifluoromethyl)-1,2,4-triazol-1-yl | N | Cl | 4.18 |
| I-1-283 | H | H | C₂H₅ | I | CH₃ | CH₂ | 3,5-bis(trifluoromethyl)-1,2,4-triazol-1-yl | N | Cl | 3.89 |
| I-1-284 | H | H | 1-cyclopropylethyl | I | CH₃ | CH₂ | 3,5-bis(trifluoromethyl)-1,2,4-triazol-1-yl | N | Cl | 4.16 |
| I-1-285 | H | H | neopentyl | I | CH₃ | CH₂ | 3,5-bis(trifluoromethyl)-1,2,4-triazol-1-yl | N | Cl | 4.23 |

TABLE 1-continued

| No. | R¹ | R² | R³ | R⁴ | R⁵ | A | Q | X | R⁷ | logP |
|---|---|---|---|---|---|---|---|---|---|---|
| I-1-286 | H | H | 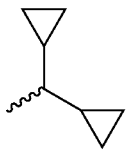 | I | CH₃ | CH₂ | 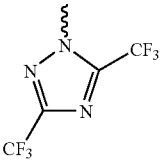 3,5-bis(CF₃)-1,2,4-triazol-1-yl | N | Cl | 4.52 |
| I-1-287 | H | H | 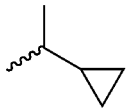 | I | CH₃ | CH₂ | 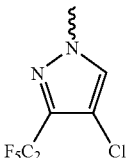 4-Cl-3-C₂F₅-pyrazol-1-yl | N | Cl | 4.69 |
| I-1-288 | H | H | 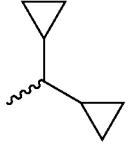 | I | CH₃ | CH₂ | 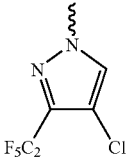 4-Cl-3-C₂F₅-pyrazol-1-yl | N | Cl | 4.79 |
| I-1-289 | H | H | 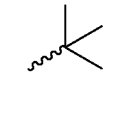 t-Bu | I | CH₃ | CH₂ | 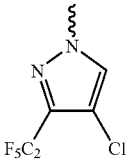 4-Cl-3-C₂F₅-pyrazol-1-yl | N | Cl | 4.63 |
| I-1-290 | H | H | CH₃ | Cl | Cl | CH₂ | 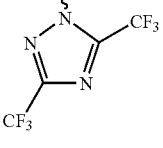 3,5-bis(CF₃)-1,2,4-triazol-1-yl | N | Cl | 3.40 |
| I-1-291 | H | H | i-Pr | Cl | Cl | CH₂ | 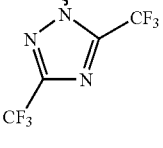 3,5-bis(CF₃)-1,2,4-triazol-1-yl | N | Cl | 3.76 |
| I-1-292 | H | H | CH₂CN | Cl | Cl | CH₂ | 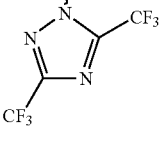 3,5-bis(CF₃)-1,2,4-triazol-1-yl | N | Cl | 2.83 |
| I-1-293 | H | H | 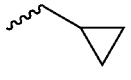 | Cl | Cl | CH₂ | 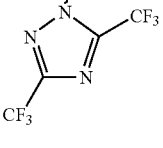 3,5-bis(CF₃)-1,2,4-triazol-1-yl | N | Cl | 3.22 |
| I-1-294 | H | H | i-Pr | Cl | Cl | CH₂ | 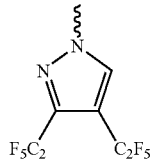 3,4-bis(C₂F₅)-pyrazol-1-yl | N | Cl | 4.00 |

TABLE 1-continued

| No. | R¹ | R² | R³ | R⁴ | R⁵ | A | Q | X | R⁷ | logP |
|---|---|---|---|---|---|---|---|---|---|---|
| I-1-295 | H | H | c-Pr | Cl | Cl | CH₂ | 1H-1,2,4-triazole with CF₃ at 3 and 5 positions | N | Cl | 2.95 |
| I-1-296 | H | H | H | Cl | Cl | CH₂ | pyrazole with C₂F₅ at 3 and 4 | N | Cl | 3.43 |
| I-1-297 | H | H | CH₃ | Cl | Cl | CH₂ | pyrazole with C₂F₅ at 3 and 4 | N | Cl | 3.59 |
| I-1-298 | H | H | H | Cl | Cl | CH₂ | 1H-1,2,4-triazole with CF₃ at 3 and 5 | N | Cl | 2.61 |
| I-1-299 | H | H | CH₂CN | Cl | Cl | CH₂ | pyrazole with C₂F₅ at 3 and 4 | N | Cl | 3.53 |
| I-1-300 | H | H | c-Pr | Cl | Cl | CH₂ | pyrazole with CF₃ at 3 and 5 | N | Cl | 3.19 |
| I-1-301 | H | H | i-Pr | Cl | Cl | CH₂ | furan | N | Cl | 2.60 |
| I-1-302 | H | H | H | Cl | Cl | CH₂ | pyrazole with CF₃ at 3 and 5 | N | Cl | 2.80 |
| I-1-303 | H | H | CH₂CN | Cl | Cl | CH₂ | pyrazole with CF₃ at 3 and 5 | N | Cl | 2.98 |

TABLE 1-continued

| No. | R¹ | R² | R³ | R⁴ | R⁵ | A | Q | X | R⁷ | logP |
|---|---|---|---|---|---|---|---|---|---|---|
| I-1-304 | H | H | CH₃ | Cl | Cl | CH₂ | 3,5-bis(CF₃)-pyrazol-1-yl | N | Cl | 3.01 |
| I-1-305 | H | H | i-Pr | Cl | Cl | CH₂ | 3,5-bis(CF₃)-pyrazol-1-yl | N | Cl | 3.40 |
| I-1-306 | H | H | CH₃ | Cl | Cl | CH₂ | furan-3-yl | N | Cl | 2.18 |
| I-1-307 | H | H | H | Cl | Cl | CH₂ | 3-(C₂F₅)-4-Cl-pyrazol-1-yl | N | Cl | 2.95 |
| I-1-308 | H | H | CH₃ | Cl | Cl | CH₂ | 3-(C₂F₅)-4-Cl-pyrazol-1-yl | N | Cl | 3.18 |
| I-1-309 | H | H | i-Pr | Cl | Cl | CH₂ | 3-(C₂F₅)-4-Cl-pyrazol-1-yl | N | Cl | 3.53 |
| I-1-310 | H | H | CH₂CN | Cl | Cl | CH₂ | 3-(C₂F₅)-4-Cl-pyrazol-1-yl | N | Cl | 3.13 |
| I-1-311 | H | H | H | Cl | Cl | CH₂ | 3-(CF₃)-pyrazol-1-yl | N | Cl | 2.21 |
| I-1-312 | H | H | CH₃ | Cl | Cl | CH₂ | 3-(CF₃)-pyrazol-1-yl | N | Cl | 2.37 |

TABLE 1-continued
| No. | R¹ | R² | R³ | R⁴ | R⁵ | A | Q | X | R⁷ | logP |
|---|---|---|---|---|---|---|---|---|---|---|
| I-1-313 | H | H | CH₂CN | Cl | Cl | CH₂ | 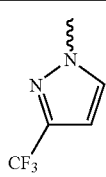 | N | Cl | 2.43 |
| I-1-314 | H | H | i-Pr | Cl | Cl | CH₂ | 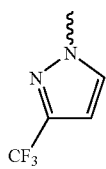 | N | Cl | 2.77 |
| I-1-315 | H | H | c-Pr | Cl | Cl | CH₂ | 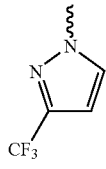 | N | Cl | 2.54 |
| I-1-316 | H | H | CH₃ | Cl | Cl | CH₂ | 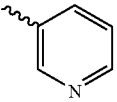 | N | Cl | 1.03 |
| I-1-317 | H | H | i-Pr | Cl | Cl | CH₂ | 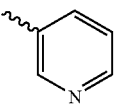 | N | Cl | 1.31 |
| I-1-318 | H | H | i-Pr | Cl | Cl | CH₂ |  | N | Cl | 1.62 |
| I-1-319 | H | H | H | Cl | Cl | CH₂ | 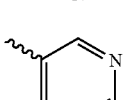 | N | Cl | 2.02 |
| I-1-320 | H | H | CH₂CN | Cl | Cl | CH₂ | 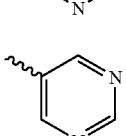 | N | Cl | 1.49 |
| I-1-321 | H | H | CH₃ | Cl | Cl | CH₂ | 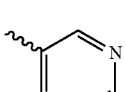 | N | Cl | 1.41 |
| I-1-322 | H | H | CH₃ | Cl | Cl | CH₂ | 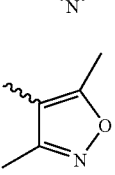 | N | Cl | 1.94 |
| I-1-323 | H | H | i-Pr | Cl | CH₃ | CH₂ | 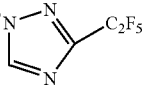 | N | Cl | 3.01 |

TABLE 1-continued

| No. | R¹ | R² | R³ | R⁴ | R⁵ | A | Q | X | R⁷ | logP |
|---|---|---|---|---|---|---|---|---|---|---|
| I-1-324 | H | H | (S)—CH(CH₃)CH₂SCH₃ | Cl | Cl | CH₂ | 1-pyrazolyl, 3-C₂F₅, 4-C₂F₅ | N | Cl | * |
| I-1-325 | H | H | (S)—CH(CH₃)CH₂SOCH₃ | Cl | Cl | CH₂ | 1-pyrazolyl, 3-C₂F₅, 4-C₂F₅ | N | Cl | 3.54 |
| I-1-326 | H | H | CH₃ | Cl | Cl | CH₂ | 1,2,4-triazolyl, 3-C₂F₅ | N | Cl | 2.55 |
| I-1-327 | H | H | i-Pr | Cl | Cl | CH₂ | 1,2,4-triazolyl, 3-C₂F₅ | N | Cl | 2.97 |
| I-1-328 | H | H | (S)—CH(CH₃)CH₂SO₂CH₃ | Cl | Cl | CH₂ | 1-pyrazolyl, 3-C₂F₅, 4-C₂F₅ | N | Cl | 3.63 |
| I-1-329 | H | H | CH₃ | Cl | CH₃ | CH₂ | 1,2,4-triazolyl, 3-C₂F₅ | N | Cl | 2.57 |
| I-1-330 | H | H | H | Cl | CH₃ | CH₂ | 1,2,4-triazolyl, 3-C₂F₅ | N | Cl | 2.39 |
| I-1-331 | H | H | c-Pr | Cl | CH₃ | CH₂ | 1,2,4-triazolyl, 3-C₂F₅ | N | Cl | 2.78 |
| I-1-332 | H | H | CH₂CN | Cl | CH₃ | CH₂ | 1,2,4-triazolyl, 3-C₂F₅ | N | Cl | 2.59 |
| I-1-333 | H | H | CH₃ | CN | CH₃ | CH₂ | 1,2,4-triazolyl, 3-C₂F₅ | N | Cl | 2.25 |
| I-1-334 | H | H | i-Pr | Cl | CH₃ | CH₂ | 1,2,4-triazolyl, 3-C₂F₅ | N | Cl | 2.66 |
| I-1-335 | H | H | c-Pr | Cl | Cl | CH₂ | 1,2,4-triazolyl, 3-C₂F₅ | N | Cl | 2.69 |

TABLE 1-continued
| No. | R¹ | R² | R³ | R⁴ | R⁵ | A | Q | X | R⁷ | logP |
|---|---|---|---|---|---|---|---|---|---|---|
| I-1-336 | H | H | H | Cl | Cl | CH₂ | 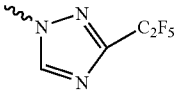 | N | Cl | 2.32 |
| I-1-337 | H | H | CH₂CN | Cl | Cl | CH₂ | 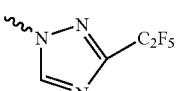 | N | Cl | 2.56 |
| I-1-338 | H | H | c-Pr | CN | CH₃ | CH₂ | 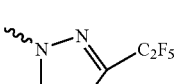 | N | Cl | 2.45 |
| I-1-339 | H | H | H | CN | CH₃ | CH₂ | 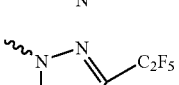 | N | Cl | 2.11 |
| I-1-340 | H | H | i-Pr | Cl | Cl | CH₂ | 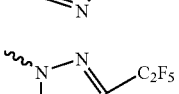 | N | Cl | 2.55 |
| I-1-341 | H | H | i-Pr | Cl | CH₃ | CH₂ | 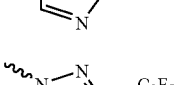 | N | Cl | 2.63 |
| I-1-342 | H | H | CH₃ | Cl | Cl | CH₂ | 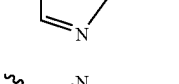 | N | Cl | 2.15 |
| I-1-343 | H | H | H | Cl | CH₃ | CH₂ | 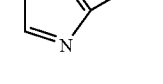 | N | Cl | 2.02 |
| I-1-344 | H | H | c-Pr | Cl | Cl | CH₂ | 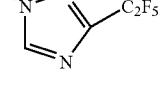 | N | Cl | 2.37 |
| I-1-345 | H | H | c-Pr | Cl | CH₃ | CH₂ | 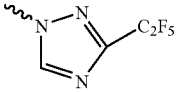 | N | Cl | 2.42 |
| I-1-346 | H | H | H | Cl | Cl | CH₂ | 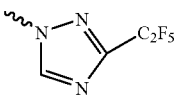 | N | Cl | 2.01 |
| I-1-347 | H | H | CH₃ | Cl | CH₃ | CH₂ | 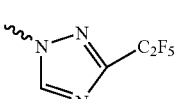 | N | Cl | 2.19 |
| I-1-348 | H | H | CH₂CN | Cl | CH₃ | CH₂ | 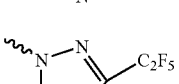 | N | Cl | 2.21 |
| I-1-349 | H | H | CH₂CN | Cl | Cl | CH₂ | 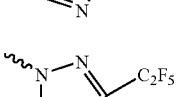 | N | Cl | 2.19 |

TABLE 1-continued
| No. | R¹ | R² | R³ | R⁴ | R⁵ | A | Q | X | R⁷ | logP |
|---|---|---|---|---|---|---|---|---|---|---|
| I-1-350 | H | H | H | CN | CH₃ | CH₂ | 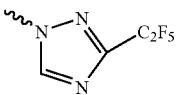 | N | Cl | 1.75 |
| I-1-351 | H | H | CH₂CN | CN | CH₃ | CH₂ | 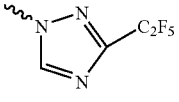 | N | Cl | 1.96 |
| I-1-352 | H | H | CH₃ | CN | CH₃ | CH₂ | 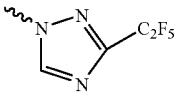 | N | Cl | 1.91 |
| I-1-353 | H | H | c-Pr | CN | CH₃ | CH₂ | 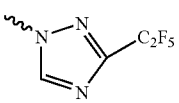 | N | Cl | 2.08 |
| I-1-354 | H | H | i-Pr | CN | CH₃ | CH₂ | 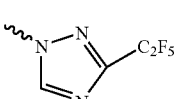 | N | Cl | 2.23 |
| I-1-355 | H | H | CH₃ | Cl | CH₃ | C=NOCH₃ | 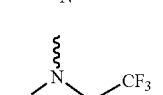 | N | Cl | 4.07 |
In analogy to the examples given above and also to the general description, the following compounds of the formula (I-2) are obtained.
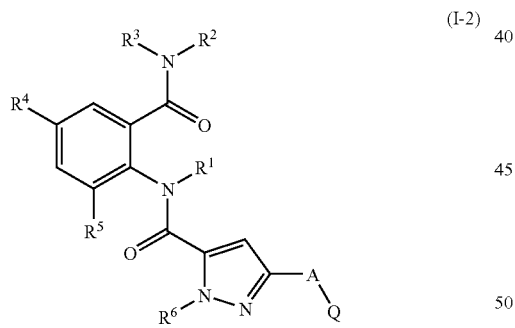
(I-2)
TABLE 2
| No. | R¹ | R² | R³ | R⁴ | R⁵ | R⁶ | A | Q | logP |
|---|---|---|---|---|---|---|---|---|---|
| I-2-1 | H | H | i-Pr | Cl | CH₃ | CH₃ | CH₂ | 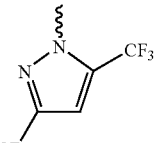 | 4.08 |

TABLE 2-continued
| No. | R¹ | R² | R³ | R⁴ | R⁵ | R⁶ | A | Q | logP |
|---|---|---|---|---|---|---|---|---|---|
| I-2-2 | H | H | i-Pr | Cl | Cl | i-Pr | CH₂ | 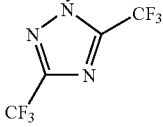 | 3.85 |
| I-2-3 | H | H | CH₃ | Cl | Cl | i-Pr | CH₂ | 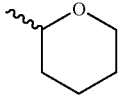 | 3.31 |
| I-2-4 | H | H | CH₃ | Cl | Cl | 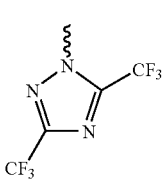 | CH₂ | 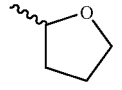 | * |
| I-2-5 | H | H | CH₃ | Cl | Cl | 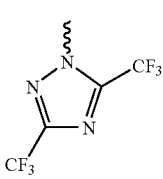 | CH₂ |  | 2.83 |
| I-2-6 | H | H | CH₃ | Cl | Cl | 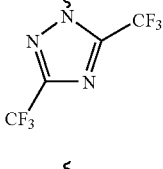 | CH₂ | 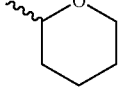 | 2.99 |
| I-2-7 | H | H | i-Pr | Cl | Cl | 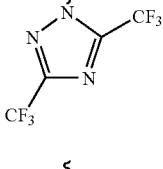 | CH₂ | 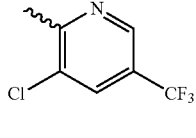 | * |
| I-2-8 | H | H | i-Pr | Cl | Cl | 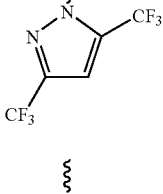 | CH₂ | 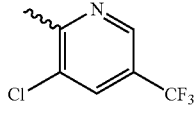 | 4.68 |
| I-2-9 | H | H | i-Pr | I | CH₃ | 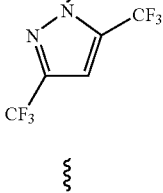 | CH₂ | 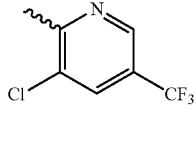 | 4.98 |
| I-2-10 | H | H | c-Pr | I | CH₃ | 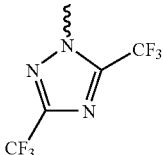 | CH₂ | 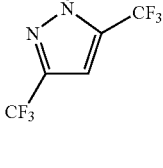 | 4.73 |

TABLE 2-continued
| No. | R¹ | R² | R³ | R⁴ | R⁵ | R⁶ | A | Q | logP |
|---|---|---|---|---|---|---|---|---|---|
| I-2-11 | H | H | i-Pr | Cl | CH₃ | 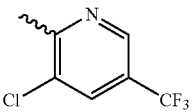 | CH₂ | 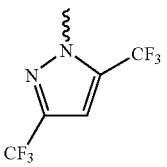 | 4.78 |
| I-2-12 | H | H | c-Pr | Cl | CH₃ | 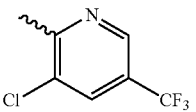 | CH₂ | 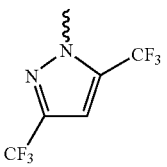 | 4.52 |
| I-2-13 | H | H | c-Pr | Cl | Cl | 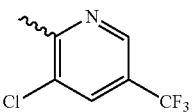 | CH₂ | 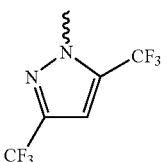 | 4.46 |
| I-2-14 | H | H | 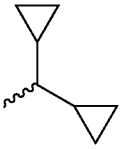 | Cl | CH₃ | 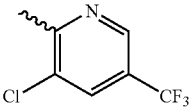 | CH₂ | 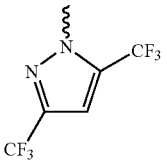 | 5.27 |
| I-2-15 | H | H | 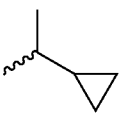 | Cl | CH₃ | 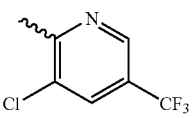 | CH₂ | 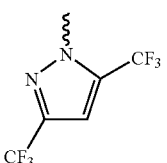 | 4.04 |
| I-2-16 | H | H | t-Bu | Cl | CH₃ | 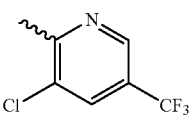 | CH₂ | 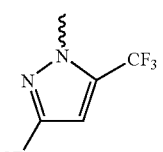 | 5.12 |
| I-2-17 | H | H | H | Cl | CH₃ | 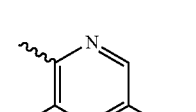 | CH₂ | 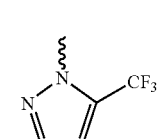 | 4.09 |

TABLE 2-continued
| No. | R¹ | R² | R³ | R⁴ | R⁵ | R⁶ | A | Q | logP |
|---|---|---|---|---|---|---|---|---|---|
| I-2-18 | H | H | CH$_2$CN | Cl | CH$_3$ | 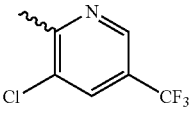 | CH$_2$ | 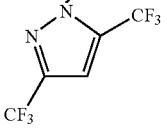 | 4.23 |
| I-2-19 | H | H | c-Pr | F | CH$_3$ | 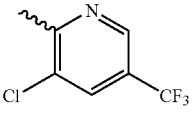 | CH$_2$ | 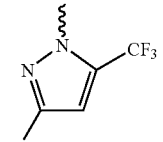 | 4.11 |
| I-2-20 | H | H | i-Pr | F | CH$_3$ | 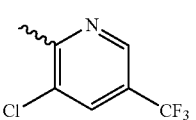 | CH$_2$ | 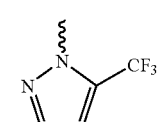 | 4.47 |
| I-2-21 | H | H | i-Pr | Br | CH$_3$ | 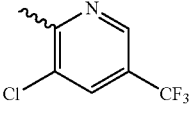 | CH$_2$ | 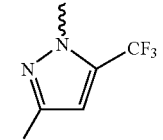 | 4.75 |
| I-2-22 | H | H | CH$_3$ | Cl | CH$_3$ | 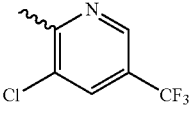 | CH$_2$ | 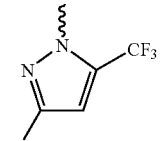 | 3.53 |
| I-2-23 | H | H | CH$_3$ | Cl | Cl | 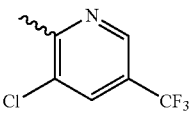 | CH$_2$ | 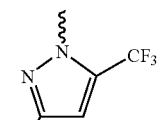 | 3.54 |
| I-2-24 | H | H | c-Pr | Br | CH$_3$ | 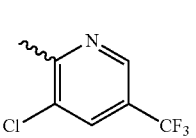 | CH$_2$ | 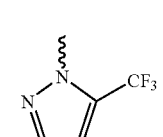 | 4.63 |

In analogy to the examples given above and also to the general description, the following compounds of the formula (I-3) are obtained.

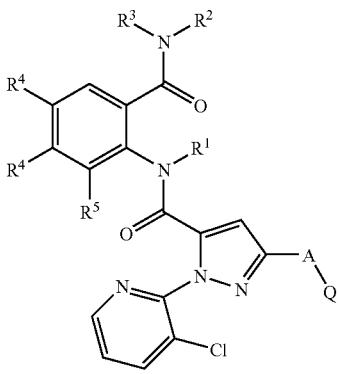

(I-3)

TABLE 3

| No. | R¹ | R² | R³ | R⁴—R⁴ | R⁵ | A | Q | logP |
|---|---|---|---|---|---|---|---|---|
| I-3-1 | H | H | i-Pr | —CH=CH—CH=CH— | Cl | CH₂ | pyrazole-3,5-bis(CF₃) | 4.08 |

¹H NMR data of selected compounds:

I-1-21 (400 MHz, DMSO): 1.11 (d, 6H), 2.14 (s, 3H), 3.91 (m, 1H), 5.55 (s, 2H), 7.12 (s, 1H), 7.28 (s, 1H), 7.39 (s, 1H), 7.55 (dd, 1H), 7.76 (d, 1H), 7.99 (s, 1H), 8.08 (d, 1H), 8.43 (d, 1H), 8.61 (s, 1H), 10.12 (s, 1H).

I-1-22 (400 MHz, DMSO): 1.18 (d, 6H), 2.14 (s, 3H), 3.90 (m, 1H), 5.87 (s, 2H), 7.24 (s, 1H), 7.42 (s, 1H), 7.53 (s, 1H), 7.55 (dd, 1H), 7.80 (d, 1H), 8.08 (d, 1H), 8.44 (d, 1H), 10.07 (s, 1H).

I-1-26 (400 MHz, DMSO): 2.14 (s, 3H), 2.67 (d, 3H), 5.93 (s, 2H), 7.21 (s, 1H), 7.33 (s, 1H), 7.40 (s, 1H), 7.55 (dd, 1H), 8.00 (d, 1H), 8.08 (d, 1H), 8.45 (d, 1H), 10.12 (s, 1H).

I-1-48 (400 MHz, DMSO): 2.13 (s, 3H), 5.69 (s, 2H), 7.18 (s, 1H), 7.41 (s, 2H), 7.55 (dd, 1H), 8.10 (d, 1H), 8.45 (d, 1H), 8.80 (s, 1H), 10.19 (s, 1H).

I-1-65 (400 MHz, DMSO): 1.06 (d, 6H), 2.17 (s, 3H), 3.95 (m, 1H), 5.58 (s, 2H), 7.15 (s, 1H), 7.31 (s, 1H), 7.42 (s, 1H), 7.58 (dd, 1H), 7.78 (d, 1H), 7.92 (s, 1H), 8.09 (d, 1H), 8.46 (d, 1H), 8.47 (s, 1H), 10.04 (s, 1H).

I-1-75 (400 MHz, DMSO): 1.09 (d, 6H), 2.00 (s, 3H), 2.15 (s, 3H), 2.44 (dd, 1H), 2.53 (dd, 1H), 3.99 (m, 1H), 5.86 (s, 2H), 7.23 (s, 1H), 7.33 (s, 1H), 7.42 (s, 1H), 7.55 (dd, 1H), 7.92 (d, 1H), 8.09 (d, 1H), 8.44 (d, 1H), 10.04 (s, 1H).

I-1-88 (400 MHz, DMSO): 2.14 (s, 3H), 2.67 (d, 3H), 5.38 (s, 2H), 7.28 (s, 1H), 7.33 (s, 1H), 7.40 (s, 1H), 7.55 (dd, 1H), 7.96 (d, 2H), 8.00 (d, 1H), 8.08 (d, 1H), 8.17 (d, 2H), 8.46 (d, 1H), 10.10 (s, 1H).

I-1-104 (400 MHz, DMSO): 2.13 (s, 3H), 2.64 (d, 3H), 6.18 (s, 2H), 7.28 (s, 1H), 7.32 (s, 1H), 7.40 (s, 1H), 7.55 (dd, 1H), 7.92 (d, 2H), 8.00 (d, 1H), 8.09 (d, 1H), 8.30 (d, 2H), 8.45 (d, 1H), 10.10 (s, 1H).

I-1-117 (400 MHz, DMSO): 1.02 (d, 6H), 2.15 (s, 3H), 3.34 (s, 3H), 3.92 (m, 1H), 5.10 (s, 2H), 7.17 (s, 1H), 7.29 (s, 1H), 7.39 (s, 1H), 7.55 (dd, 1H), 7.78 (d, 1H), 8.09 (d, 1H), 8.44 (d, 1H), 10.01 (s, 1H).

I-1-126 (400 MHz, DMSO): 0.99-1.10 (m, 4H), 1.03 (d, 6H), 2.15 (s, 3H), 3.00-3.08 (m, 1H), 3.92 (m, 1H), 5.05 (s, 2H), 7.16 (s, 1H), 7.29 (s, 1H), 7.40 (s, 1H), 7.55 (dd, 1H), 7.78 (d, 1H), 8.09 (d, 1H), 8.44 (d, 1H), 10.01 (s, 1H).

I-1-139 (400 MHz, DMSO): 1.38 (s, 6H), 2.14 (s, 3H), 2.89 (s, 3H), 3.68 (s, 2H), 5.87 (s, 2H), 7.21 (s, 1H), 7.31 (s, 1H), 7.40 (s, 1H), 7.55 (dd, 1H), 7.79 (s, 1H), 8.09 (d, 1H), 8.44 (d, 1H), 9.93 (s, 1H).

I-1-148 (400 MHz, DMSO): 2.14 (s, 3H), 2.66 (d, 3H), 6.18 (s, 2H), 7.29 (s, 1H), 7.32 (s, 1H), 7.40 (s, 1H), 7.55 (dd, 1H), 7.70 (d, 1H), 8.09 (d, 1H), 8.11 (d, 1H), 8.45 (s, 1H), 8.46 (d, 1H), 9.07 (s, 1H), 10.10 (s, 1H).

I-1-161 (400 MHz, DMSO): 1.04 (d, 6H), 1.31 (s, 9H), 2.14 (s, 3H), 3.90 (m, 1H), 5.46 (s, 2H), 7.11 (s, 1H), 7.29 (s, 1H), 7.39 (s, 1H), 7.55 (dd, 1H), 7.78 (d, 1H), 8.09 (d, 1H), 8.40 (s, 1H), 8.44 (d, 1H), 10.10 (s, 1H).

I-1-172 (400 MHz, DMSO): 1.04 (d, 6H), 2.15 (s, 3H), 3.90 (m, 1H), 5.58 (s, 2H), 7.16 (s, 1H), 7.55 (dd, 1H), 7.70 (s, 1H), 7.78 (s, 1H), 7.93 (d, 1H), 8.09 (d, 1H), 8.38 (s, 1H), 8.45 (d, 1H), 10.32 (s, 1H).

I-1-175 (400 MHz, DMSO): 2.21 (s, 3H), 4.16 (d, 1H), 5.57 (s, 2H), 7.16 (s, 1H), 7.55 (dd, 1H), 7.70 (s, 1H), 7.78 (s, 1H), 7.86 (d, 1H), 8.09 (d, 1H), 8.37 (s, 1H), 8.46 (d, 1H), 10.32 (s, 1H).

I-1-176 (400 MHz, DMSO): 2.19 (s, 3H), 2.68 (d, 1H), 5.88 (s, 2H), 7.25 (s, 1H), 7.55 (dd, 1H), 7.80 (s, 1H), 7.97 (s, 1H), 8.09 (d, 1H), 8.15 (d, 1H), 8.44 (d, 1H), 10.40 (s, 1H).

I-1-180 (400 MHz, DMSO): 2.21 (s, 3H), 4.16 (d, 1H), 5.87 (s, 2H), 7.27 (s, 1H), 7.55 (dd, 1H), 7.77 (s, 1H), 7.86 (s, 1H), 8.09 (d, 1H), 8.46 (d, 1H), 8.96 (d, 1H), 10.34 (s, 1H).

I-1-182 (400 MHz, DMSO): 1.04 (d, 6H), 2.19 (s, 3H), 3.92 (m, 1H), 5.57 (s, 2H), 6.74 (s, 1H), 7.15 (s, 1H), 7.55 (dd, 1H), 7.70 (s, 1H), 7.78 (s, 1H), 7.91 (d, 1H), 8.06 (s, 1H), 8.09 (d, 1H), 8.45 (d, 1H), 10.30 (s, 1H).

I-1-190 (400 MHz, DMSO): 2.21 (s, 3H), 4.15 (d, 1H), 5.69 (s, 2H), 7.18 (s, 1H), 7.53 (s, 1H), 7.55 (dd, 1H), 7.76 (s, 1H), 7.85 (s, 1H), 8.07 (d, 1H), 8.45 (d, 1H), 8.95 (s, 1H), 10.30 (s, 1H).

I-1-195 (400 MHz, DMSO): 1.11 (d, 6H), 2.00 (s, 3H), 2.15 (s, 3H), 2.44 (dd, 1H), 2.53 (dd, 1H), 4.02 (m, 1H), 5.57 (s, 2H), 7.08 (d, 1H), 7.15 (s, 1H), 7.20 (d, 1H), 7.55 (dd, 1H), 7.84 (d, 1H), 8.09 (d, 1H), 8.37 (s, 1H), 8.45 (d, 1H), 10.30 (s, 1H).

I-1-196 (400 MHz, DMSO): 2.15 (s, 3H), 4.34 (d, 1H), 5.57 (s, 2H), 6.19 (d, 1H), 6.29 (d, 1H), 7.10 (s, 1H), 7.13 (d, 1H), 7.22 (d, 1H), 7.43 (s, 1H), 7.55 (dd, 1H), 8.08 (d, 1H), 8.38 (s, 1H), 8.46 (d, 1H), 8.55 (t, 1H), 10.30 (s, 1H).

I-1-201 (400 MHz, DMSO): 2.14 (s, 3H), 4.33 (d, 1H), 5.57 (s, 2H), 6.19 (d, 1H), 6.29 (d, 1H), 7.10 (s, 1H), 7.33 (s, 1H), 7.44 (2 d, 2H), 7.55 (dd, 1H), 8.08 (d, 1H), 8.37 (s, 1H), 8.45 (d, 1H), 8.55 (t, 1H), 10.34 (s, 1H).

I-1-208 (400 MHz, DMSO): 2.14 (s, 3H), 4.33 (d, 1H), 5.57 (s, 2H), 6.19 (d, 1H), 6.29 (d, 1H), 7.13 (s, 1H), 7.45 (s, 1H), 7.55 (dd, 1H), 7.75 (s, 1H), 7.80 (s, 1H), 8.08 (d, 1H), 8.38 (s, 1H), 8.69 (br s, 1H), 8.55 (t, 1H), 10.34 (s, 1H).

I-1-241 (400 MHz, DMSO): 1.02 (d, 3H), 2.11 (s, 3H), 3.91 (m, 1H), 5.57 (s, 2H), 7.12 (s, 1H), 7.55 (dd, 1H), 7.57 (s, 1H), 7.69 (s, 1H), 7.76 (d, 1H), 8.08 (d, 1H), 8.37 (s, 1H), 8.45 (d, 1H), 10.02 (s, 1H).

I-1-243 (400 MHz, DMSO): 2.10 (s, 3H), 2.67 (d, 3H), 3.07 (q, 2H), 5.57 (s, 2H), 7.13 (s, 1H), 7.55 (dd, 1H), 7.60 (s, 1H), 7.70 (s, 1H), 7.98 (d, 1H), 8.10 (d, 1H), 8.38 (s, 1H), 8.45 (d, 1H), 10.09 (s, 1H).

I-1-244 (400 MHz, DMSO): 0.99 (t, 3H), 2.11 (s, 3H), 3.07 (q, 2H), 5.87 (s, 2H), 7.21 (s, 1H), 7.55 (dd, 1H), 7.59 (s, 1H), 7.70 (s, 1H), 7.98 (s, 1H), 8.09 (d, 1H), 8.45 (d, 1H), 10.05 (s, 1H).

I-1-248 (400 MHz, DMSO): 1.01 (d, 6H), 2.10 (s, 3H), 3.89 (m, 1H), 5.56 (s, 2H), 6.73 (s, 1H), 7.11 (s, 1H), 7.55 (dd, 1H), 7.56 (s, 1H), 7.76 (s, 1H), 7.75 (d, 1H), 8.04 (s, 1H), 8.09 (d, 1H), 8.45 (d, 1H), 10.01 (s, 1H).

I-1-274 (400 MHz, DMSO): 0.99 (t, 3H), 2.10 (s, 3H), 3.07 (q, 2H), 5.68 (s, 2H), 7.15 (s, 1H), 7.55 (dd, 1H), 7.60 (s, 1H), 7.97 (s, 1H), 8.08 (d, 1H), 8.45 (d, 1H), 10.09 (s, 1H).

I-1-275 (400 MHz, DMSO): 0.40-0.47 (m, 2H), 0.55-0.60 (m, 2H), 2.10 (s, 3H), 2.65-2.71 (m, 1H), 5.69 (s, 2H), 7.17 (s, 1H), 7.55 (dd, 1H), 7.56 (s, 1H), 7.69 (s, 1H), 8.00 (d, 1H), 8.08 (d, 1H), 8.45 (s, 1H), 8.79 (d, 1H), 10.05 (s, 1H).

I-1-276 (400 MHz, DMSO): 0.41-0.45 (m, 2H), 0.56-0.61 (m, 2H), 2.10 (s, 3H), 2.65-2.71 (m, 1H), 5.57 (s, 2H), 7.14 (s, 1H), 7.55 (dd, 1H), 7.55 (s, 1H), 7.69 (s, 1H), 8.01 (d, 1H), 8.08 (d, 1H), 8.38 (s, 1H), 8.46 (d, 1H), 10.02 (s, 1H).

I-1-279 (400 MHz, DMSO): 1.34-1.60 (m, 6H), 1.71-1.78 (m, 2H), 2.10 (s, 3H), 4.01-4.08 (m, 1H), 5.87 (s, 2H), 7.21 (s, 1H), 7.55 (dd, 1H), 7.57 (s, 1H), 7.70 (s, 1H), 7.85 (d, 1H), 8.07 (d, 1H), 8.43 (s, 1H), 10.02 (s, 1H).

I-1-280 (400 MHz, DMSO): 1.13-1.51 (m, 20H), 1.71-1.78 (m, 2H), 2.07 (s, 3H), 3.93-3.96 (m, 1H), 5.83 (s, 2H), 7.13 (s, 1H), 7.55 (dd, 1H), 7.61 (s, 1H), 7.68 (d, 1H), 8.02 (s, 1H), 8.07 (d, 1H), 8.43 (s, 1H), 10.02 (s, 1H).

I-1-282 (400 MHz, DMSO): 1.36 (s, 2H), 1.56-1.65 (m, 2H), 1.84-1.94 (m, 2H), 2.07 (s, 3H), 4.18-4.24 (m, 1H), 5.87 (s, 2H), 7.18 (s, 1H), 7.55 (dd, 1H), 7.59 (s, 1H), 7.70 (d, 1H), 8.07 (s, 1H), 8.19 (d, 1H), 8.43 (s, 1H), 10.02 (s, 1H).

I-1-290 (400 MHz, CDCl$_3$): 2.90 (d, 3H), 5.74 (s, 2H), 6.10 (d, 1H), 7.23 (s, 1H), 7.23 (s, 1H), 7.28 (s, 1H), 7.40 (dd, 1H), 7.87 (d, 1H), 8.46 (d, 1H), 9.74 (s, 1H).

I-1-296 (400 MHz, CDCl$_3$): 5.54 (s, 2H), 5.62 (s, 1H), 6.11 (s, 1H), 7.12 (s, 1H), 7.39 (s, 1H), 7.40 (dd, 1H), 7.48 (s, 1H), 7.90 (d, 1H), 7.94 (s, 1H), 8.48 (d, 1H), 9.45 (s, 1H).

I-1-310 (400 MHz, CDCl$_3$): 4.18 (d, 2H), 5.48 (s, 2H), 6.74 (t, 1H), 7.08 (s, 1H), 7.32 (s, 1H), 7.43 (dd, 1H), 7.48 (s, 1H), 7.92 (d, 1H), 7.94 (s, 1H), 8.50 (d, 1H), 8.93 (s, 1H).

I-1-314 (400 MHz, CDCl$_3$): 1.10 (d, 6H), 4.08 (m, 1H), 5.50 (s, 2H), 5.92 (d, 1H), 6.57 (s, 1H), 7.15 (s, 1H), 7.28 (s, 1H), 7.39 (s, 1H), 7.40 (dd, 1H), 7.57 (s, 1H), 7.87 (d, 1H), 8.48 (d, 1H), 9.65 (s, 1H).

I-1-324 (400 MHz, CDCl$_3$): 1.24 (d, 3H), 2.10 (s, 3H), 2.60 (m, 2H), 4.22 (m, 1H), 5.51 (d, 1H), 5.58 (d, 1H), 6.13 (d, 1H), 7.17 (s, 1H), 7.35 (s, 1H), 7.39 (s, 1H), 7.40 (dd, 1H), 7.87 (d, 1H), 7.90 (s, 1H), 8.48 (d, 1H), 9.60 (s, 1H).

I-1-331 (400 MHz, CDCl$_3$): 0.55 (m, 2H), 0.85 (m, 2H), 2.16 (s, 3H), 2.77 (m, 1H), 5.57 (s, 2H), 6.18 (d, 1H), 7.12 (s, 1H), 7.18 (s, 1H), 7.24 (s, 1H), 7.41 (dd, 1H), 7.88 (d, 1H), 8.35 (s, 1H), 8.48 (d, 1H), 10.15 (s, 1H).

I-1-334 (400 MHz, CDCl$_3$): 1.24 (d, 6H), 2.23 (s, 3H), 4.18 (m, 1H), 5.58 (s, 2H), 5.99 (d, 1H), 7.12 (s, 1H), 7.28 (s, 1H), 7.40 (dd, 1H), 7.58 (d, 1H), 7.88 (d, 1H), 8.36 (s, 1H), 8.48 (d, 1H), 10.62 (s, 1H).

I-1-340 (400 MHz, CDCl$_3$): 1.24 (d, 6H), 4.08 (m, 1H), 5.58 (s, 2H), 5.92 (d, 1H), 7.21 (s, 1H), 7.30 (s, 1H), 7.32 (s, 1H), 7.40 (dd, 1H), 7.77 (d, 1H), 8.36 (s, 1H), 8.48 (d, 1H), 10.06 (s, 1H).

I-1-345 (400 MHz, CDCl$_3$): 0.55 (m, 2H), 0.85 (m, 2H), 2.77 (m, 1H), 5.58 (s, 2H), 6.20 (d, 1H), 7.14 (s, 1H), 7.20 (s, 1H), 7.22 (s, 1H), 7.40 (dd, 1H), 7.88 (d, 1H), 8.32 (s, 1H), 8.45 (d, 1H), 10.12 (s, 1H).

I-1-354 (400 MHz, CDCl$_3$): 1.21 (d, 6H), 4.15 (m, 1H), 5.58 (s, 2H), 7.16 (s, 1H), 7.18 (s, 1H), 7.40 (dd, 1H), 7.58 (s, 1H), 7.75 (s, 1H), 7.84 (d, 1H), 8.38 (s, 1H), 8.48 (d, 1H), 10.95 (s, 1H).

I-2-4 (400 MHz, CDCl$_3$): 1.74 (m, 3H), 2.16 (m, 2H), 2.40 (m, 1H), 2.86 (d, 3H), 3.70 (m, 1H), 3.88 (m, 1H), 5.75 (s, 2H), 5.80 (m, 1H), 6.45 (s, 1H), 6.80 (s, 1H), 7.16 (s, 1H), 7.42 (s, 1H), 7.56 (s, 1H), 9.08 (s, 1H).

I-2-7 (400 MHz, CDCl$_3$): 1.24 (m, 6H), 1.74 (m, 3H), 2.20 (m, 2H), 2.40 (m, 1H), 3.70 (m, 1H), 3.88 (m, 1H), 4.10 (m, 1H), 5.80 (m, 3H), 6.25 (s, 1H), 6.80 (s, 1H), 7.40 (s, 1H), 7.52 (s, 1H), 8.85 (s, 1H).

The $^1$H NMR data given above are determined using a Bruker Avance 400 equipped with a BEST system (60 μl volume cell) or with a Bruker Avance 400 using tetramethylsilane as reference (0.0 ppm) and the solvents CDCl$_3$ at 298 kelvins or d6-DMSO at 304 kelvins. Signal splitting is characterized by s=singlet, d=doublet, t=triplet, q=quartet, m=multiples, dd=doublet of doublet.

The log P values stated in the foregoing tables and preparation examples are determined in accordance with EEC Directive 79/831 Annex V.A8 by means of HPLC (High Performance Liquid Chromatography) on a reverse-phase column (C 18). Temperature: 43° C.

The determination by LC-MS in the acidic range takes place at a pH of 2.7 using 0.1% aqueous formic acid and acetonitrile (containing 0.1% formic acid) as eluents; linear gradient from 10% acetonitrile to 95% acetonitrile.

Calibration is with unbranched alkan-2-ones (having 3 to 16 carbon atoms) of known log P value (log P values determined from the retention times by linear interpolation between two successive alkanones).

The lambda-max values are determined from the UV spectra from 200 nm to 400 nm in the maxima of the chromatographic signals.

Preparation of Starting Materials of the Formula (V)

Example 2

2-[5-(3,5-Bistrifluoromethylpyrazol-1-ylmethyl)-2-(3-chloropyridin-2-yl)-2H-pyrazol-3-yl]-6-chloro-8-methylbenzo[d][1,3]oxazin-4-one Under argon 0.12 ml (1.60 mmol) of methanesulphonyl chloride in 3 ml of acetonitrile are cooled to 0° C. and subsequently a solution of 540 mg (1.228 mmol) of 5-(3,5-bistrifluoromethylpyrazol-1-ylmethyl)-2-(3-chloropyridin-2-yl)-2H-pyrazole-3-carboxylic acid in 0.17 ml (2.09 mmol) of pyridine and 6 ml of acetonitrile is added dropwise. The mixture is stirred at this temperature for 15 minutes and then a solution of 228 mg (1.228 mmol) of 2-amino-5-chloro-3,N-dimethylbenzamide in 0.35 ml (4.30 mmol) of pyridine and 6 ml of acetonitrile is added. After a further 15 minutes at 0° C. the mixture is admixed with 0.12 ml (1.60 mmol) of methanesulphonyl chloride and warmed slowly to room temperature overnight. The solvent is removed in vacuo, 15 ml of water are added and the crystals formed are filtered off with suction.

Yield: 500 mg (log P: 5.11)

Preparation of Starting Materials of the Formula (IV)

Example 3

5-(3,5-Bistrifluoromethylpyrazol-1-ylmethyl)-2-(3-chloropyridin-2-yl)-2H-pyrazole-3-carboxylic acid A solution of 610 mg (1.34 mmol) of methyl 5-(3,5-bistri-fluoromethylpyrazol-1-ylmethyl)-2-(3-chloropyridin-2-yl)-2H-pyrazole-3-carboxylate in 9 ml of ethanol is admixed dropwise with a solution of 699 mg (1.78 mmol) of sodium hydroxide in 7 ml of water. The mixture is stirred at room temperature for 2 hours and concentrated to about 5 ml on a rotary evaporator. This residue is admixed with 5 ml of tert-butyl methyl ether and the organic phase is subsequently washed with water. The combined aqueous phases are adjusted to a pH of about 3 with concentrated hydrochloric acid, with ice cooling, and are extracted with three times 50 ml of ethyl acetate. The combined organic phases are dried over magnesium sulphate and then the solvent is removed on a rotary evaporator.

Yield: 560 mg (log P: 2.86)

Preparation of Starting Materials of the Formula (IV)

Example 4

Methyl 5-(3,5-bistrifluoromethylpyrazol-1-ylmethyl)-2-(3-chloropyridin-2-yl)-2H-pyrazole-3-carboxylate A solution of 700 mg (2.03 mmol) of methyl 2-(3-chloropyridin-2-yl)-5-methane-sulphonyloxymethyl-2H-pyrazole-3-carboxylate in 15 ml of acetonitrile is admixed in succession with 336 mg (2.43 mmol) of potassium carbonate and 413 mg (2.03 mmol) of 3,5-bis(trifluoromethyl)pyrazole and the mixture is subsequently stirred at 60° C. for 1 h. After the mixture has cooled to room temperature, the solvent is concentrated on a rotary evaporator, water is added and extraction is carried out with three times 50 ml of ethyl acetate. The combined organic phases are dried over magnesium sulphate and then the solvent is removed on a rotary evaporator.

Yield: 970 mg (log P: 3.71)

Preparation of Starting Materials of the Formula (VII)

Example 5

Methyl 2-(3-chloropyridin-2-yl)-5-methanesulpho-nyloxymethyl-2H-pyrazole-3-carboxylate Under argon 2.10 g (7.85 mmol) of methyl 2-(3-chloropyridin-2-yl)-5-hydroxymethyl-2H-pyrazole-3-carboxylate are introduced in 13 ml of dichloromethane and this initial charge is cooled to 0° C. and admixed dropwise in succession with 1.64 ml (11.8 mmol) of triethylamine and 0.67 ml (8.63 mmol) of methanesulphonyl chloride. It is stirred at this temperature for 30 minutes, diluted with 50 ml of dichloromethane and washed successively with 50 ml each of saturated aqueous sodium hydrogen sulphate solution, 10 percent strength aqueous hydrochloric acid and saturated aqueous sodium chloride solution. The organic phase is dried over magnesium sulphate and then the solvent is removed on a rotary evaporator.

Yield: 2.65 g (log P: 1.55)

Preparation of Starting Materials of the Formula (X)

Example 6

Methyl 2-(3-chloropyridin-2-yl)-5-hydroxymethyl-2H-pyrazole-3-carboxylate

Under argon 12.3 g (41.7 mmol) of dimethyl 1-(3-chloropyridin-2-yl)-1H-pyrazole-3,5-dicarboxylate are introduced in 430 ml of tetrahydrofuran and this initial charge is cooled to −72° C. and admixed dropwise with 100 ml (100 mmol of a 1 M solution in hexane) of diisobutylaluminium hydride. The mixture is allowed to warm to 0° C. overnight and 65 ml of water are cautiously added. The solvents are removed on a rotary evaporator and the residue is extracted to exhaustion with methanol on a Soxhlet apparatus. Following removal of the solvent, the residue is purified on silica gel (cyclohexane/ethyl acetate=2:1→1:1).

Yield: 9.26 g (log P: 1.26)

Preparation of Starting Materials of the Formula (XI)

Example 7

Dimethyl 1-(3-chloropyridin-2-yl)-1H-pyrazole-3,5-dicarboxylate

One spatula tip of toluenesulphonic acid is added to a solution of 15.6 g (64.8 mmol) of dimethyl 2-pyrrolidino-4-oxo-2-pentenedicarboxylate and 20.4 g (64.8 mmol) of the toluenesulphonic acid salt of 3-chloro-2-pyridin-2-ylhydrazine in 84 ml of methanol and the mixture is heated at 50° C. for 5 h. It is then admixed with 12.3 g (64.8 mmol) of toluenesulphonic acid monohydrate and stirred initially at 50° C. for 1 h and under reflux for 1 h. After the mixture has cooled to 0° C., the precipitated crystals are filtered off with suction and filtration is carried out over silica gel (cyclohexane/ethyl acetate=1:1).

Yield: 8.56 g (log P: 1.97)

Examples in relation to the biological activity of the compounds of the invention

Example 1

| *Heliothis virescens* test | |
|---|---|
| Solvents: | 1% N-methylpyrrolidone (NMP) |
|  | 1% diacetone alcohol |
| Dye: | Brilliant sulphoflavine to stain the water |

An appropriate preparation of active compound is prepared by mixing the active compound with the stated amounts of solvent and diluting the concentrate with stained water to the desired concentration.

The *Heliothis virescens* eggs are treated with a preparation of active compound at the desired concentration.

After the desired time the effect in % is determined. 100% means that all of the eggs/larvae have been killed; 0% means that no eggs/larvae have been killed.

High activity in this test is shown, for example, by the following compounds of the preparation examples: see table

| Heliothis virescens test | | |
|---|---|---|
| Active compound | Active compound concentration in ppm | Kill level after 6-7$^d$ in % |
| I-1-13 | 300 | 100 |
| I-1-14 | 300 | 100 |
| I-1-15 | 300 | 100 |

Example 2

| Myzus persicae test | |
|---|---|
| Solvents: | 1% N-methylpyrrolidone (NMP) |
| | 1% diacetone alcohol |
| Dye: | Brilliant sulphoflavine to stain the water |

An appropriate preparation of active compound is prepared by mixing the active compound with the stated amounts of solvent and diluting the concentrate with stained water to the desired concentration.

The *Myzus persicae* is provided with a preparation of active compound at the desired concentration for consumption.

After the desired time the effect in % is determined. 100% means that all of the aphids have been killed; 0% means that no aphids have been killed.

High activity in this test is shown, for example, by the following compounds of the preparation examples: see table

| Myzus persicae test | | |
|---|---|---|
| Active compound | Active compound concentration in ppm | Kill level after 6-7$^d$ in % |
| I-1-13 | 30 | 100 |
| I-1-14 | 30 | 100 |
| I-1-15 | 30 | 100 |

Example 3

| Aedes aegypti test | |
|---|---|
| Solvents: | 1% N-methylpyrrolidone (NMP) |
| | 1% diacetone alcohol |
| Dye: | Brilliant sulphoflavine to stain the water |

An appropriate preparation of active compound is prepared by mixing the active compound with the stated amounts of solvent and diluting the concentrate with stained water to the desired concentration.

The *Aedes aegypti* larvae are treated with a preparation of active compound at the desired concentration.

After the desired time the effect in % is determined. 100% means that all of the *Aedes aegypti* have been killed; 0% means that no *Aedes aegypti* have been killed.

High activity in this test is shown, for example, by the following compounds of the preparation examples: see table

| Aedes Aegypti test | | |
|---|---|---|
| Active compound | Active compound concentration in ppm | Kill level after 2-4$^d$ in % |
| I-1-13 | 30 | 100 |
| I-1-14 | 30 | 100 |
| I-1-15 | 30 | 100 |

Example 4

| Diabrotica undecimpunctata test | |
|---|---|
| Solvents: | 1% N-methylpyrrolidone (NMP) |
| | 1% diacetone alcohol |
| Dye: | Brilliant sulphoflavine to stain the water |

An appropriate preparation of active compound is prepared by mixing the active compound with the stated amounts of solvent and diluting the concentrate with stained water to the desired concentration.

The *Diabrotica undecimpunctata* eggs are treated with a preparation of active compound at the desired concentration.

After the desired time the effect in % is determined. 100% means that all of the eggs/larvae have been killed; 0% means that no eggs/larvae have been killed.

High activity in this test is shown, for example, by the following compounds of the preparation examples: see table

| Diabrotica undecimpunctata test | | |
|---|---|---|
| Active compound | Active compound concentration in ppm | Kill level after 2-5$^d$ in % |
| I-1-13 | 300 | 100 |
| I-1-14 | 300 | 100 |
| I-1-15 | 300 | 100 |

Example 5

| Phaedon test (spray treatment) | |
|---|---|
| Solvents: | 78.0 parts by weight acetone |
| | 1.5 parts by weight dimethylformamide |
| Emulsifier: | 0.5 part by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration.

Leaf discs of Chinese cabbage (*Brassica pekinensis*) are sprayed with a preparation of active compound at the desired concentration and, after drying, are populated with larvae of the mustard beetle (*Phaedon cochleariae*).

After the desired time the effect in % is determined. 100% means that all of the beetle larvae have been killed; 0% means that no beetle larvae have been killed.

In this test an effect of ≧80% is shown, for example, by the following compounds of the preparation examples at an application rate of 100 g/ba:

Ex. No. I-1-2, I-1-3, I-1-4, I-1-5, I-1-6, I-1-10, I-1-11, I-1-12, I-1-13, I-1-14, I-1-15, I-1-16, I-1-17, I-1-18, I-1-19, I-1-22, I-1-23, I-1-24, I-1-25, I-1-28, I-1-29, I-1-30, I-1-31, I-1-32, I-1-33, I-1-34, I-1-35, I-1-36, I-1-37, I-1-38, I-1-39, I-1-40, I-1-217, I-1-218, I-1-219, I-1-220, I-1-222, I-1-223, I-1-224, I-1-225, I-1-226, I-1-38, I-1-42, I-1-43, I-1-44, I-1-45, I-1-46, I-1-47, I-1-48, I-1-49, I-1-50, I-1-51, I-1-52, I-1-53, I-1-54, I-1-55, I-1-56, I-1-57, I-1-58, I-1-59, I-1-60, I-1-61, I-1-62, I-1-63, I-1-64, I-1-65, I-1-66, I-1-68, I-1-69, I-1-70, I-1-71, I-1-72, I-1-73, I-1-74, I-1-75, I-1-76, I-1-77, I-1-78, I-1-79, I-1-80, I-1-81, I-1-82, I-1-83, I-1-84, I-1-85, I-1-86, I-1-87, I-1-92, I-1-93, I-1-97, I-1-99, I-1-100, I-1-101, I-1-113, I-1-120, I-1-121, I-1-125, I-1-128, I-1-129, I-1-130, I-1-131, I-1-134, I-1-135, I-1-137, I-1-138, I-1-139, I-1-140, I-1-141, I-1-142, I-1-144, I-1-145, I-1-146, I-1-147, I-1-148, I-1-149, I-1-150, I-1-151, I-1-152, I-1-155, I-1-156, I-1-157, I-1-158, I-1-163, I-1-165, I-1-166, I-1-167, I-1-168, I-1-169, I-1-170, I-1-171, I-1-172, I-1-173, I-1-174, I-1-175, I-1-176, I-1-177, I-1-178, I-1-179, I-1-180, I-1-181, I-1-182, I-1-183, I-1-184, I-1-185, I-1-186, I-1-187, I-1-188, I-1-189, I-1-190, I-1-191, I-1-192, I-1-193, I-1-195, I-1-196, I-1-199, I-1-201, I-1-203, I-1-204, I-1-206, I-1-207, I-1-208, I-1-209, I-1-210, I-1-211, I-1-212, I-1-213, I-1-214, I-1-215, I-1-216, I-1-227, I-1-228, I-1-230, I-1-231, I-1-233, I-1-234, I-1-235, I-1-236, I-1-237, I-1-238, I-1-239, I-1-240, I-1-241, I-1-242, I-1-243, I-1-244, I-1-245, I-1-246, I-1-247, I-1-248, I-1-251, I-1-252, I-1-253, I-1-255, I-1-258, I-1-259, I-1-260, I-1-267, I-1-272, I-1-273, I-1-274, I-1-275, I-1-276, I-1-277, I-1-279, I-1-282, I-1-283, I-1-284, I-1-285, I-1-286, I-1-287, I-1-288, I-1-289, I-1-290, I-1-291, I-1-292, I-1-293, I-1-294, I-1-295, I-1-296, I-1-297, I-1-298, I-1-299, I-1-300, I-1-302, I-1-303, I-1-304, I-1-305, I-1-307, I-1-308, I-1-309, I-1-310, I-1-312, I-1-313, I-1-324, I-1-326, I-1-327, I-1-328, I-1-329, I-1-330, I-1-331, I-1-332, I-1-333, I-1-334, I-1-335, I-1-336, I-1-337, I-1-338, I-1-339, I-1-340, I-1-342, I-1-343, I-1-346, I-1-347, I-1-348, I-1-349, I-1-350, I-1-352, I-1-353, I-1-354, I-1-355, I-2-2

High activity in this test is shown, for example, by the following compounds of the preparation examples: see table

| Spodoptera frugiperda test | | |
|---|---|---|
| Active compound | Active compound concentration in g/ha | Kill level after $7^d$ in % |
| I-1-1 | 100 | 100 |
| I-1-2 | 100 | 100 |
| I-1-3 | 100 | 100 |
| I-1-4 | 100 | 100 |
| I-1-5 | 100 | 100 |
| I-1-6 | 100 | 100 |
| I-1-7 | 100 | 100 |
| I-1-8 | 100 | 100 |
| I-1-10 | 100 | 100 |
| I-1-11 | 100 | 100 |
| I-1-12 | 100 | 100 |
| I-1-13 | 100 | 100 |
| I-1-14 | 100 | 100 |
| I-1-15 | 100 | 100 |
| I-1-16 | 100 | 100 |
| I-1-17 | 100 | 100 |
| I-1-18 | 100 | 100 |
| I-1-19 | 100 | 100 |
| I-1-20 | 100 | 100 |
| I-1-21 | 100 | 100 |
| I-1-22 | 100 | 100 |
| I-1-23 | 100 | 100 |
| I-1-24 | 100 | 100 |
| I-1-25 | 100 | 100 |
| I-1-26 | 100 | 100 |
| I-1-27 | 20 | 83 |
| I-1-28 | 100 | 100 |
| I-1-29 | 100 | 100 |
| I-1-30 | 100 | 100 |
| I-1-31 | 100 | 100 |
| I-1-32 | 100 | 100 |
| I-1-33 | 100 | 100 |
| I-1-34 | 100 | 100 |
| I-1-35 | 100 | 100 |
| I-1-36 | 100 | 100 |
| I-1-37 | 100 | 100 |
| I-1-38 | 100 | 100 |
| I-1-39 | 100 | 100 |
| I-1-40 | 100 | 100 |

Example 6

| Spodoptera frugiperda test | |
|---|---|
| Solvent: | 7 parts by weight dimethylformamide |
| Emulsifier: | 2 parts by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration.

Cabbage leaves (*Brassica oleracea*) are treated by immersion into a preparation of active compound at the desired concentration and, are populated with caterpillars of the armyworm (*Spodoptera frugiperda*) while the leaves are still wet.

After the desired time the effect in % is determined. 100% means that all of the caterpillars have been killed; 0% means that no caterpillars have been killed.

Example 7

| Spodoptera exigua test | |
|---|---|
| Solvent: | 7 parts by weight dimethylformamide |
| Emulsifier: | 2 parts by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration. If it is necessary to add ammonium salts, penetrants, or ammonium salts and penetrants, they are added by pipette at a concentration of 1000 ppm after dilution, the addition taking place in each case to the completed solution of the products. Examples I-1-3, I-1-5, I-1-6, I-1-8 and I-1-22 are tested without addition of ammonium salts or penetrants.

Cabbage plants (*Brassica oleracea*) are treated by being sprayed with the preparation of active compound at the desired concentration and are populated with caterpillars of the beet armyworm (*Spodoptera exigua*) while the leaves are still wet.

After the desired time the kill in % is determined. 100% means that all of the caterpillars have been killed; 0% means that no caterpillars have been killed.

In this test an effect of ≧80% is shown, for example, by the following compounds of the preparation examples at an application rate of 4 ppm:

Ex. No. I-1-3, I-1-5, I-1-6, I-1-8, I-1-22, I-1-31, I-1-35, I-1-47, I-1-48, I-1-52, I-1-53, I-1-55, I-1-57, I-1-170, I-1-291, I-1-295, I-1-296, I-1-297, I-1-299, I-1-54

Example 8

| *Plutella xylostella* test | |
|---|---|
| Solvent: | 7 parts by weight dimethylformamide |
| Emulsifier: | 2 parts by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration. If it is necessary to add ammonium salts, penetrants, or ammonium salts and penetrants, they are added by pipette at a concentration of 1000 ppm after dilution, the addition taking place in each case to the completed solution of the products. Examples I-1-3, I-1-5, I-1-6, I-1-8 and I-1-22 are tested without addition of ammonium salts or penetrants.

Cabbage leaves (*Brassica oleracea*) are treated by being sprayed with the preparation of active compound at the desired concentration and are populated with caterpillars of the cabbage moth (*Plutella xylostella*) while the leaves are still wet.

After the desired time the kill in % is determined. 100% means that all of the caterpillars have been killed; 0% means that no caterpillars have been killed.

In this test an effect of ≧80% is shown, for example, by the following compounds of the preparation examples at an application rate of 20 ppm:

Ex. No. I-1-3, I-1-5, I-1-6, I-1-8, I-1-22, I-1-65, I-1-239, I-1-240, I-1-245, I-1-217, I-1-220, I-1-223, I-1-224, I-1-31, I-1-55, I-1-56, I-1-57, I-1-63, I-1-66, I-1-68, I-1-69, I-1-76, I-1-92, I-1-97, I-1-98, I-1-101, I-1-113, I-1-121, I-1-147, I-1-170, I-1-192, I-1-195, I-1-204, I-1-206, I-1-209, I-1-210, I-1-212, I-1-215, I-1-238, I-1-244, I-1-247, I-1-248, I-1-249, I-1-250, I-1-251, I-1-274, I-1-275, I-1-276, I-1-291, I-1-295, I-1-296, I-1-297, I-1-299, I-1-25, I-1-35, I-1-36, I-1-38, I-1-43, I-1-46, I-1-47, I-1-48, I-1-52, I-1-53, I-1-54, I-1-104, I-1-106, I-1-107, I-1-108, I-1-143, I-1-88, I-1-139

Example 9

| *Spodoptera frugiperda* test | |
|---|---|
| Solvent: | 7 parts by weight dimethylformamide |
| Emulsifier: | 2 parts by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration.

Cabbage leaves (*Brassica oleracea*) are treated by immersion into a preparation of active compound at the desired concentration and are populated with caterpillars of the armyworm (*Spodoptera frugiperda*) while the leaves are still wet.

After the desired time the effect in % is determined. 100% means that all of the caterpillars have been killed; 0% means that no caterpillars have been killed.

High activity in this test is shown, for example, by the following compounds of the preparation examples: see table

| *Spodoptera frugiperda* - Test | | |
|---|---|---|
| Active compound | Active compound concentration in g/ha | Kill level after $7^d$ in % |
| I-1-3 | 0.8 | 100 |
| I-1-5 | 0.8 | 100 |
| I-1-6 | 0.8 | 100 |
| I-1-8 | 0.8 | 100 |
| I-1-9 | 100 | 100 |
| I-1-22 | 4 | 100 |

Example 10

| *Heliothis armigera* test | |
|---|---|
| Solvent: | 7 parts by weight dimethylformamide |
| Emulsifier: | 2 parts by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration. If it is necessary to add ammonium salts, penetrants, or ammonium salts and penetrants, they are added by pipette at a concentration of 1000 ppm after dilution, the addition taking place in each case to the completed solution of the products. Examples I-1-3, I-1-5, I-1-6, I-1-8 and I-1-22 are tested without addition of ammonium salts or penetrants.

Cotton plants (*Gossypium hirsutum*) are treated by being sprayed with the preparation of active compound at the desired concentration and are populated with caterpillars of the cotton budworm (*Heliothis armigera*) while the leaves are still wet.

After the desired time the kill in % is determined. 100% means that all of the caterpillars have been killed; 0% means that no caterpillars have been killed.

In this test an effect of ≧80% is shown, for example, by the following compounds of the preparation examples at an application rate of 20 ppm:

Ex. No. I-1-3, I-1-5, I-1-6, I-1-8, I-1-22, I-1-63, I-1-65, I-1-66, I-1-68, I-1-69, I-1-192, I-1-240, I-1-245, I-1-217, I-1-220, I-1-223, I-1-224, I-1-31, I-1-35, I-1-36, I-1-38, I-1-43, I-1-46, I-1-47, I-1-48, I-1-52, I-1-53, I-1-54, I-1-55, I-1-56, I-1-57, I-1-76, I-1-88, I-1-131, I-1-139, I-1-92, I-1-97, I-1-98, I-1-100, I-1-101, I-1-113, I-1-121, I-1-147, I-1-170, I-1-195, I-1-204, I-1-206, I-1-212, I-1-215, I-1-238, I-1-244, I-1-

247, I-1-248, I-1-249, I-1-250, I-1-251, I-1-274, I-1-275, I-1-276, I-1-291, I-1-295, I-1-296, I-1-297, I-1-299, I-1-104, I-1-106, I-1-107, I-1-108, I-1-143

Example 11

| *Spodoptera exigua* test; resistant strain | |
|---|---|
| Solvent: | 7 parts by weight dimethylformamide |
| Emulsifier: | 2 parts by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration. If it is necessary to add ammonium salts, penetrants, or ammonium salts and penetrants, they are added by pipette at a concentration of 1000 ppm after dilution, the addition taking place in each case to the completed solution of the products. Examples I-1-5, I-1-6, and I-1-22 are tested without addition of ammonium salts or penetrants.

Cabbage plants (*Brassica oleracea*) are treated by being sprayed with the preparation of active compound at the desired concentration and are populated with caterpillars of the beet armyworm (*Spodoptera exigua*, resistant strain), while the leaves are still wet.

After the desired time the kill in % is determined. 100% means that all of the caterpillars have been killed; 0% means that no caterpillars have been killed.

In this test an effect of ≧80% is shown, for example, by the following compounds of the preparation examples at an application rate of 4 ppm:

Ex. No. I-1-5, I-1-6, I-1-22, I-1-31, I-1-35, I-1-38, I-1-46, I-1-47, I-1-48, I-1-52, I-1-53, I-1-54, I-1-56, I-1-57, I-1-170, I-1-295, I-1-296, I-1-297, I-1-299

Example 12

| *Liriomyza trifolii* | |
|---|---|
| Solvents: | 78 parts by weight acetone |
| | 1.5 parts by weight dimethylformamide |
| Emulsifier: | 0.5 part by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration.

Bean leaf discs (*Phaseolus vulgaris*) infested by larvae of the leafminer fly (*Liriomyza trifolii*) are sprayed with a preparation of active compound at the desired concentration.

After the desired time the effect in % is determined. 100% means that all of the leafminer flies have been killed; 0% means that no leafminer flies have been killed.

High activity in this test is shown, for example, by the following compounds of the preparation examples: see table

| *Liriomyza trifolii* Test | | |
|---|---|---|
| Active compound | Active compound concentration in ppm | Kill level after $7^d$ in % |
| I-1-3 | 500 | 98 |
| I-1-4 | 500 | 95 |
| I-1-22 | 500 | 98 |

Example 13

| *Lucilia cuprina* test | |
|---|---|
| Solvent: | Dimethyl sulphoxide |

An appropriate preparation of active compound is prepared by mixing 1 part by weight of active compound with the stated amounts of solvent and emulsifier and diluting the concentrate with water to the desired concentration.

Vessels containing horsemeat treated with the preparation of active compound at the desired concentration are populated with *Lucilia cuprina* larvae.

After the desired time the kill in % is determined. 100% means that all of the larvae have been killed; 0% means that no larvae have been killed.

In this test an effect of ≧80% is shown, for example, by the following compounds of the preparation examples at an application rate of 100 ppm:

Ex. No. I-1-1, I-1-2, I-1-3, I-1-4, I-1-5, I-1-6, I-1-7, I-1-8, I-1-9, I-1-12, I-1-14, I-1-15, I-1-16, I-1-17, I-1-18, I-1-19, I-1-21, I-1-22, I-1-29, I-1-30, I-1-31, I-1-217, I-1-220, I-1-223, I-1-224, I-1-42, I-1-43, I-1-46, I-1-47, I-1-48, I-1-52, I-1-53, I-1-54, I-1-55, I-1-56, I-1-57, I-1-64, I-1-65, I-1-66, I-1-67, I-1-68, I-1-74, I-1-88, I-1-92, I-1-97, I-1-104, I-1-107, I-1-108, I-1-109, I-1-111, I-1-114, I-1-122, I-1-123, I-1-192, I-1-238, I-1-239, I-1-240, I-1-244, I-1-247, I-1-274, I-1-275, I-1-291, I-1-295, I-1-296, I-1-297, I-1-299, I-1-323

Example 14

| *Boophilus microplus* test (Injection) | |
|---|---|
| Solvent: | Dimethyl sulphoxide |

An appropriate preparation of active compound is prepared by mixing 1 part by weight of active compound with the stated amounts of solvent and emulsifier and diluting the concentrate with solvent to the desired concentration.

The solution of active compound is injected into the abdomen (*Boophilus microplus*) and the animals are transferred to dishes and kept in a climatized room.

After the desired time the effect in % is determined. 100% means that none of the ticks has laid fertile eggs.

In this test an effect of ≧80% is shown, for example, by the following compounds of the preparation examples at an application rate of 20 μg/animal:

Ex. No. I-1-1, I-1-2, I-1-3, I-1-4, I-1-5, I-1-6, I-1-7, I-1-8, I-1-9, I-1-12, I-1-14, I-1-15, I-1-16, I-1-17, I-1-18, I-1-19, I-1-21, I-1-29, I-1-30, I-1-31, I-1-217, I-1-222, I-1-223, I-1-224, I-1-42, I-1-43, I-1-46, I-1-47, I-1-48, I-1-52, I-1-53, I-1-54, I-1-55, I-1-56, I-1-57, I-1-64, I-1-65, I-1-66, I-1-67, I-1-68, I-1-74, I-1-88, I-1-92, I-1-97, I-1-104, I-1-107, I-1-108, I-1-109, I-1-111, I-1-114, I-1-122, I-1-123, I-1-192, I-1-238, I-1-239, I-1-240, I-1-244, I-1-247, I-1-274, I-1-275, I-1-291, I-1-295, I-1-296, I-1-297, I-1-299, I-1-323

Example 15

| *Musca domestica* test | |
|---|---|
| Solvent: | Dimethyl sulphoxide |

An appropriate preparation of active compound is prepared by mixing 1 part by weight of active compound with the stated amounts of solvent and emulsifier and diluting the concentrate with water to the desired concentration.

Vessels containing a sponge treated with the preparation of active compound at the desired concentration are populated with *Musca domestica* adults.

After the desired time the kill in % is determined. 100% means that all of the flies have been killed; 0% means that no flies have been killed. In the case of Examples I-1-16, I-1-19 and I-1-30 the effect in question is a knock-down effect.

In this test an effect of ≧80% is shown, for example, by the following compounds of the preparation examples at an application rate of 100 ppm:

Ex. No. I-1-16 I-1-19, I-1-30, I-1-217, I-1-42, I-1-43, I-1-46, I-1-47, I-1-48, I-1-52, I-1-53, I-1-55, I-1-64, I-1-66, I-1-107, I-1-114, I-1-192, I-1-274, I-1-275, I-1-296, I-1-297, I-1-299

Example 16

| *Spodoptera frugiperda* test (spray treatment) | |
|---|---|
| Solvents: | 78.0 parts by weight acetone |
| | 1.5 parts by weight dimethylformamide |
| Emulsifier: | 0.5 part by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration.

Leaf discs of maize (*Zea mays*) are sprayed with a preparation of active compound at the desired concentration and, after drying, are populated with larvae of the armyworm (*Spodoptera frugiperda*).

After the desired time the effect in % is determined. 100% means that all of the caterpillars have been killed; 0% means that no caterpillars have been killed.

In this test an effect of ≧80% is shown, for example, by the following compounds of the preparation examples at an application rate of 100 g/ha:

Ex. No. I-1-217, I-1-218, I-1-219, I-1-220, I-1-221, I-1-222, I-1-223, I-1-224, I-1-38, I-1-42, I-1-43, I-1-44, I-1-45, I-1-46, I-1-47, I-1-48, I-1-49, I-1-50, I-1-51, I-1-52, I-1-53, I-1-54, I-1-55, I-1-56, I-1-57, I-1-58, I-1-59, I-1-60, I-1-61, I-1-62, I-1-63, I-1-64, I-1-65, I-1-66, I-1-68, I-1-69, I-1-70, I-1-71, I-1-72, I-1-73, I-1-74, I-1-75, I-1-76, I-1-77, I-1-78, I-1-79, I-1-80, I-1-81, I-1-82, I-1-83, I-1-84, I-1-85, I-1-86, I-1-87, I-1-92, I-1-93, I-1-97, I-1-99, I-1-100, I-1-101, I-1-102, I-1-103, I-1-113, I-1-116, I-1-117, I-1-118, I-1-119, I-1-120, I-1-121, I-1-125, I-1-126, I-1-127, I-1-128, I-1-129, I-1-130, I-1-131, I-1-134, I-1-135, I-1-136, I-1-137, I-1-138, I-1-139, I-1-140, I-1-141, I-1-142, I-1-144, I-1-145, I-1-146, I-1-147, I-1-148, I-1-149, I-1-150, I-1-151, I-1-152, I-1-153, I-1-154, I-1-155, I-1-156, I-1-157, I-1-158, I-1-160, I-1-161, I-1-163, I-1-165, I-1-166, I-1-167, I-1-168, I-3-1, I-1-169, I-1-170, I-1-171, I-1-172, I-1-173, I-1-174, I-1-175, I-1-176, I-1-177, I-1-178, I-1-179, I-1-180, I-1-181, I-1-182, I-1-183, I-1-184, I-1-185, I-1-186, I-1-187, I-1-188, I-1-189, I-1-190, I-1-191, I-1-192, I-1-193, I-1-195, I-1-196, I-1-199, I-1-200, I-1-201, I-1-202, I-1-203, I-1-204, I-1-205, I-1-206, I-1-207, I-1-208, I-1-209, I-1-210, I-1-211, I-1-212, I-1-213, I-1-214, I-1-215, I-1-216, I-1-225, I-1-226, I-1-227, I-1-228, I-1-231, I-1-233, I-1-234, I-1-235, I-1-237, I-1-238, I-1-239, I-1-240, I-1-241, I-1-242, I-1-243, I-1-244, I-1-245, I-1-246, I-1-247, I-1-248, I-1-249, I-1-250, I-1-251, I-1-252, I-1-253, I-1-255, I-1-257, I-1-258, I-1-259, I-1-260, I-1-261, I-1-262, I-1-263, I-1-264, I-1-266, I-1-267, I-1-268, I-1-269, I-1-270, I-1-271, I-1-272, I-1-273, I-1-274, I-1-275, I-1-276, I-1-277, I-1-279, I-1-282, I-1-283, I-1-284, I-1-285, I-1-286, I-1-287, I-1-289, I-2-8, I-2-12, I-2-17, I-2-19, I-1-290, I-1-291, I-1-292, I-1-293, I-1-294, I-1-295, I-1-296, I-1-297, I-1-298, I-1-299, I-1-300, I-1-301, I-1-302, I-1-303, I-1-304, I-1-305, I-1-307, I-1-308, I-1-309, I-1-310, I-1-311, I-1-312, I-1-313, I-1-314, I-1-315, I-1-318, I-1-324, I-1-326, I-1-327, I-1-328, I-1-329, I-1-330, I-1-331, I-1-332, I-1-333, I-1-334, I-1-335, I-1-336, I-1-337, I-1-338, I-1-339, I-1-341, I-1-343, I-1-344, I-1-346, I-1-347, I-1-348, I-1-349, I-1-350, I-1-351, I-1-352, I-1-353, I-1-354, I-1-355, I-2-2, I-2-3

Example 17

| *Myzus* test (spray treatment) | |
|---|---|
| Solvents: | 78.0 parts by weight acetone |
| | 1.5 parts by weight dimethylformamide |
| Emulsifier: | 0.5 part by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration.

Leaf discs of Chinese cabbage (*Brassica pekinensis*) infested by all stages of the green peach aphid (*Myzus persicae*) are sprayed with a preparation of active compound at the desired concentration.

After the desired time the effect in % is determined. 100% means that all of the aphids have been killed; 0% means that no aphids have been killed.

In this test an effect of ≧80% is shown, for example, by the following compounds of the preparation examples at an application rate of 100 g/ha:

Ex. No. I-1-64, I-1-68, I-1-74, I-1-75, I-1-76, I-1-77, I-1-78, I-1-80, I-1-81, I-1-83, I-1-84, I-1-92, I-1-97, I-1-99, I-1-100, I-1-101, I-1-113, I-1-116, I-1-117, I-1-118, I-1-120, I-1-121, I-1-126, I-1-127, I-1-128, I-1-130, I-1-131, I-1-134, I-1-135, I-1-36, I-1-137, I-1-138, I-1-139, I-1-142, I-1-144, I-1-145, I-1-146, I-1-150, I-1-152, I-1-163, I-1-174, I-1-176, I-1-177, I-1-178, I-1-179, I-1-180, I-1-184, I-1-185, I-1-186, I-1-198, I-1-203, I-1-207, I-1-209, I-1-211, I-1-212, I-1-216, I-1-272, I-2-10, I-1-308, I-1-326, I-1-327, I-1-329, I-1-330, I-1-331, I-1-332, I-1-333, I-1-336, I-1-338, I-1-339, I-1-354

Example 18

| *Aphis gossypii* test | |
|---|---|
| Solvent: | 7 parts by weight dimethylformamide |
| Emulsifier: | 2 parts by weight alkylaryl polyglycol ether |

An appropriate preparation of active compound is prepared by mixing 1 part by weight of active compound with the stated amounts of solvent and emulsifier and diluting the concentrate with emulsifier-containing water to the desired concentration. If it is necessary to add ammonium salts, penetrants, or ammonium salts and penetrants, they are added by pipette at a concentration of 1000 ppm after dilution, the addition taking place in each case to the completed solution of the products.

Cotton leaves (*Gossypium hirsutm*) heavily infested by the cotton aphid (*Aphis gossypii*) are sprayed with the preparation of active compound at the desired concentration.

After the desired time the kill in % is determined. 100% means that all of the aphids have been killed; 0% means that no aphids have been killed.

In this test an effect of ≧80% is shown, for example, by the following compounds of the preparation examples at an application rate of 100 ppm:

Ex. No. I-1-68, I-1-75, I-1-76, I-1-88, I-1-98, I-1-99, I-1-104, I-1-108, I-1-113, I-1-131, I-1-139, I-1-143, I-1-176, I-1-251

The invention claimed is:
1. A Compound of formula (I)

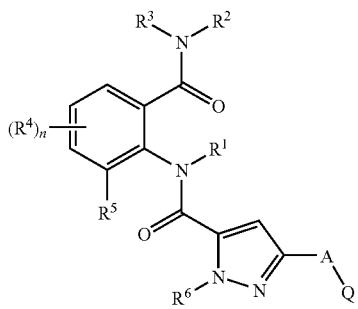

in which
$R^1$ represents hydrogen, amino or hydroxyl or represents $C_1$-$C_6$-alkyl, $C_2$-$C_6$-alkenyl, $C_2$-$C_6$-alkynyl or $C_3$-$C_6$-cycloalkyl each of which is unsubstituted or substituted one or more times by identical or different substituents selectable independently of one another from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino or ($C_1$-$C_4$-alkyl)$C_3$-$C_6$-cycloalkylamino, $R^2$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di($C_1$-$C_4$-alkyl)amino, $C_3$-$C_6$-cycloalkylamino, $C_2$-$C_6$-alkoxycarbonyl or $C_2$-$C_6$-alkylcarbonyl, $R^3$ represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_{12}$-Cycloalkyl, $C_3$-$C_{12}$-Cycloalkyl-$C_1$-$C_6$-Alkyl and $C_4$-$C_{12}$-Bicycloalkyl each of which is optionally substituted one or more times by identical or different substituents selectable independently of one another from halogen, cyano, nitro, hydroxyl, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkyl-sulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkyl carbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl, or a 5- or 6-membered heteroaromatic ring, $R^2$ and $R^3$ can be joined to one another via two to six carbon atoms and foam a ring which where appropriate additionally contains a further nitrogen, sulphur or oxygen atom and where appropriate may be substituted one to four times by $C_1$-$C_2$-alkyl, halogen, cyano, amino or $C_1$-$C_2$-alkoxy, or $R^2$ and $R^3$ further together represent =S($C_1$-$C_4$-alkyl)$_2$ or =S(O)($C_1$-$C_4$-alkyl)$_2$, $R^4$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two $R^4$s, via adjacent carbon atoms, form a ring which represents —(CH$_2$)$_3$—, —(CH$_2$)$_4$—, —(CH$_2$)$_5$—, —(CH=CH—)$_2$—, —OCH$_2$O—, —O—(CH$_2$)$_2$O—, —OCF$_2$O—, —(CF$_2$)$_2$O—, —O(CF$_2$)$_2$O—, (CH=CH—CH=N)— or —(CH=CH—N=CH)—, or two $R^4$s, via adjacent carbon atoms, form the following fused rings, which where appropriate are substituted one or more times by identical or different substituents selectable independently of one another from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino or $C_3$-$C_6$-cycloalkylamino,

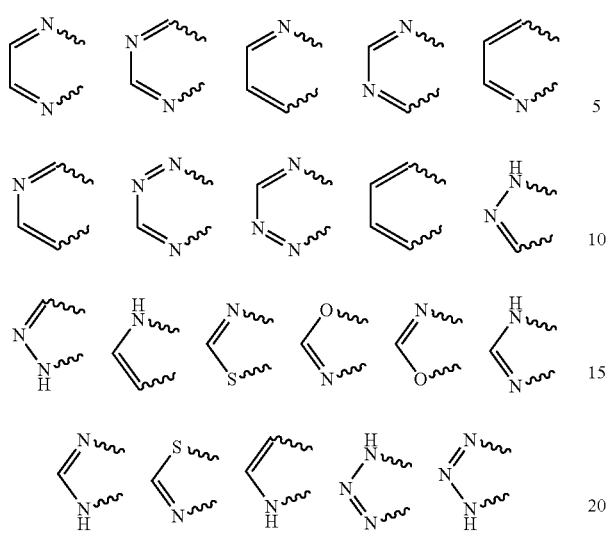

n represents 0 to 3,

R$^5$ represents C$_1$-C$_6$-alkyl, C$_3$-C$_6$-cycloalkyl, C$_1$-C$_6$-haloalkyl, C$_1$-C$_6$-halocycloalkyl, C$_2$-C$_6$-alkenyl, C$_2$-C$_6$-haloalkenyl, C$_2$-C$_6$-alkynyl, C$_2$-C$_6$-haloalkynyl, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-haloalkylsulphinyl, C$_1$-C$_4$-haloalkylsulphonyl, halogen, cyano, nitro or C$_3$-C$_6$-trialkylsilyl, R$^6$ represents hydrogen, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkoxy, C$_1$-C$_6$-haloalkyl, C$_2$-C$_6$-haloalkenyl or

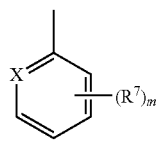

R$^7$ represents independently at each occurrence hydrogen, C$_1$-C$_6$-alkyl, C$_3$-C$_6$-cyclo-alkyl, C$_1$-C$_6$-haloalkyl, halogen, cyano, nitro, C$_1$-C$_4$-alkoxy, C$_1$-C$_4$-haloalkoxy, C$_1$-C$_4$-alkylthio or C$_1$-C$_4$-haloalkylthio, m represents 0 to 4, X represents N, CH, CF, CCl, CBr or CI, A represents —CH$_2$—, CH(CH)$_3$C(CH$_3$)$_2$, or CH$_2$CH$_2$, Q represents a 5- or 6-membered heteroaromatic ring or an aromatic 8-, 9- or 10-membered fused heterobicyclic ring system, the ring system being unsubstituted or substituted one or more times by identical or different substituents selectable independently of one another from hydrogen, C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, CO$_2$H, CO$_2$NH$_2$, NO$_2$, OH, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-haloalkylsulphinyl, C$_1$-C$_4$-halo-alkylsulphonyl, C$_1$-C$_4$-alkylamino, di(C$_1$-C$_4$-alkyl)amino, C$_3$-C$_6$-cycloalkylamino, (C$_1$-C$_6$-alkyl)carbonyl, (C$_1$-C$_6$-alkoxy)carbonyl, (C$_1$-C$_6$-alkyl)aminocarbonyl, di(C$_1$-C$_4$-alkyl)aminocarbonyl, tri-alkyl)silyl and (C$_1$-C$_4$-alkyl)(C$_1$-C$_4$-alkoxy)imino, or Q further represents a 5- or 6-membered heteroaromatic or heterocyclic ring or an aromatic 8-, 9- or 10-membered fused heterobicyclic ring system, the ring or the ring system being unsubstituted or substituted one or more times by identical or different substituents selectable independently of one another from hydrogen, C$_1$-C$_6$-alkyl, C$_2$-C$_6$-alkenyl, C$_2$-C$_6$-alkynyl, C$_3$-C$_6$-cycloalkyl, C$_2$-C$_6$-haloalkenyl, C$_2$-C$_6$-haloalkynyl, C$_3$-C$_6$-halocycloalkyl, halogen, CN, CO$_2$H, CO$_2$NH$_2$, NO$_2$, OH, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-haloalkyl-sulphinyl, C$_1$-C$_4$-haloalkylsulphonyl, di(C$_1$-C$_4$-alkyl)amino, C$_3$-C$_6$-cycloalkylamino, (C$_1$-C$_6$-alkyl)carbonyl, (C$_1$-C$_6$-alkoxy)carbonyl, (C$_1$-C$_6$-alkyl)aminocarbonyl, di(C$_1$-C$_4$-alkyl)aminocarbonyl, tri-alkyl)silyl and (C$_1$-C$_4$-alkyl)(C$_1$-C$_4$-alkoxy)imino, or the substituents being selectable independently of one another from phenyl or a 5- or 6-membered heteroaromatic ring, it being possible for phenyl or the ring to be unsubstituted or substituted one or more times by identical or different C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, NO$_2$, OH, C$_1$-C$_4$-alkoxy, C$_1$-C$_4$-haloalkoxy substituents, or salt thereof.

2. A Compound of formula (I) according to claim 1, in which

R$^1$ represents hydrogen, amino or hydroxyl or represents C$_1$-C$_6$-alkyl, C$_2$-C$_6$-alkenyl, C$_2$-C$_6$-alkynyl or C$_3$-C$_6$-cycloalkyl each of which is unsubstituted or substituted one or more times by identical or different substituents selectable independently of one another from halogen, cyano, nitro, hydroxyl, C$_1$-C$_4$-alkoxy, alkylthio, C$_1$-C$_4$-alkylsulphinyl, C$_1$-C$_4$-alkylsulphonyl, (C$_1$-C$_4$-alkoxy)carbonyl, C$_1$-C$_4$-alkylamino, di(C$_1$-C$_4$-alkyl)amino, C$_3$-C$_6$-cycloalkylamino or (C$_1$-C$_4$-alkyl)C$_3$-C$_6$-cycloalkylamino, R$^2$ represents hydrogen, C$_1$-C$_6$-alkyl, C$_2$-C$_6$-alkenyl, C$_2$-C$_6$-alkynyl, C$_3$-C$_6$-cycloalkyl, C$_1$-C$_4$-alkoxy, C$_1$-C$_4$-alkylamino, di(C$_1$-C$_4$-alkyl)amino, C$_3$-C$_6$-cycloalkylamino, C$_2$-C$_6$-alkoxycarbonyl or C$_2$-C$_6$-alkylcarbonyl, R$^3$ represents hydrogen or represents C$_1$-C$_6$-alkyl, C$_1$-C$_6$-alkoxy, C$_2$-C$_6$-alkenyl, C$_2$-C$_6$-alkynyl, C$_3$-C$_6$-cycloalkyl, each of which is optionally substituted one or more times by identical or different substituents selectable independently of one another from halogen, cyano, nitro, hydroxyl, C$_1$-C$_6$-alkyl, C$_3$-C$_6$-cycloalkyl, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-alkylsulphimino, C$_1$-C$_4$-alkylsulphimino-C$_1$-C$_4$-alkyl, C$_1$-C$_4$-alkylsulphimino-C$_2$-C$_5$-alkylcarbonyl, C$_1$-C$_4$-alkylsulphoximino, sulphoximino-C$_1$-C$_4$-alkyl, C$_1$-C$_4$-alkylsulphoximino-C$_2$-C$_5$-alkylcarbonyl, C$_2$-C$_6$-alkoxycarbonyl, C$_2$-C$_6$-alkylcarbonyl or C$_3$-C$_6$-trialkylsilyl, $R^4$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two $R^4$s, via adjacent carbon atoms, form a ring which represents —$(CH_2)_3$—, —$(CH_2)_4$—, —$(CH_2)_5$, —$(CH{=}CH{-})_2$—, —$OCH_2O$—, —$O(CH_2)_2O$—, —$OCF_2O$—, —$(CF_2)_2O$—, —$O(CF_2)_2O$—, —$(CH{=}CH{-}CH{=}N)$— or —$(CH{=}CH{-}N{=}CH)$—, n represents 0 to 3, $R^5$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl or

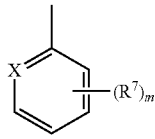

$R^7$ represents independently at each occurrence hydrogen, $C_1$-$C_6$-alkyl, $C_3$-$C_6$-cyclo-alkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m represents 0 to 4, X represents N, CH, CF, CCl, CBr or CI, A represents —$CH_2$, $CH(CH)_3C(CH_3)_2$, or $CH_2CH_2$, Q represents a 5- or 6-membered heteroatomatic ring or an aromatic 8-, 9- or 10-membered fused heterobicyclic ring system, the ring or the ring system being unsubstituted or substituted one or more times by identical or different substituents selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkyl-sulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri-alkyl)silyl and ($C_1$-$C_4$-alkyl)($C_1$-$C_4$-alkoxy)imino, or salt thereof.

3. A Compound of formula (I-1)

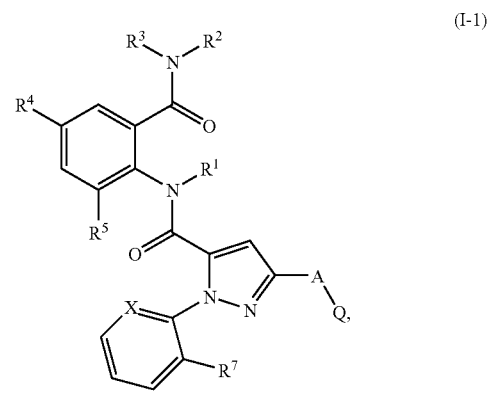

(I-1)

in which
$R^1$ represents hydrogen,
$R^2$ represents hydrogen,
$R^3$ represents $C_1$-$C_4$-alkyl,
$R^4$ represents hydrogen, methyl, trifluoromethyl, cyano, fluorine, chlorine, bromine, iodine or trifluoromethoxy,
$R^5$ represents methyl, fluorine, chlorine, bromine or iodine,
$R^7$ represents fluorine, chlorine or bromine,
X represents N, CCl or CH,
A represents $CH_2$ or $CH(CH_3)$,
Q represents an optionally mono- or polysubstituted aromatic heterocyclic ring of series Q-37, Q-38, Q-39, Q-40, Q-58 and Q-59, and also represents a 5-membered heterocyclic ring Q-60, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy or $C_1$-$C_4$-haloalkoxy substituents, or salt thereof.

4. A method for controlling phytopathogenic fungi comprising using a compound of claim 1.

5. Method of controlling phytopathogenic fungi, comprising causing a compound of formula (I) according to claim 1 to act on phytopathogenic fungi.

6. A Process for producing agrochemical compositions comprising mixing a compound of formula (I) according to claim 1 with extenders and/or surface-active substances.

7. A method for treating phytopathogenic fungi comprising using compound of formula (I) according to claim 1.

8. Seed treated with a compound of formula (I) according to claim 1.

9. A Process for producing agrochemical compositions comprising mixing a compound of formula (I) according to claim 2 with extenders and/or surface-active substances.

10. A method for treating phytopathogenic fungi comprising using a compound of formula (I) according to claim 2.

11. Seed treated with a compound of the formula (I) according to claim 2.

12. A method for controlling phytopathogenic fungi comprising using a compound of claim 2.

13. A process of preparing a compound of formula (I) according to claim 1 comprising (A) reacting an aniline of formula (II)

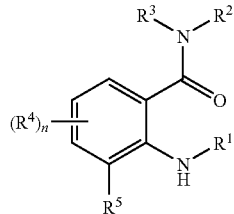
(II)

in which A, $R^1$, $R^2$, $R^3$, $R^4$, $R^5$ are defined by Formula I, with carbonyl chlorides of the formula (III)

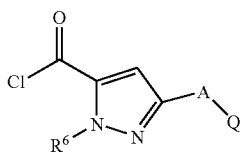
(III)

in which $R^6$, A and Q are defined by Formula I, in the presence of an acid-binding agent, (B) reacting anilines of the formula (II)

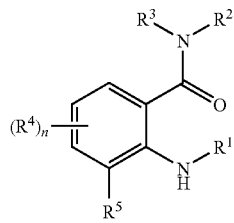
(II)

in which A, $R^1$, $R^2$, $R^3$, $R^4$, $R^5$ and n are defined by Formula I, with a carboxylic acid of formula (IV)

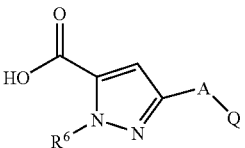
(IV)

in which $R^6$, A and Q are defined by Formula I, in the presence of a condensing agent, or by (C) synthesizing anthranilamides of the formula (I) in which $R^1$ represents hydrogen by reacting benzoxazinones of the formula (V)

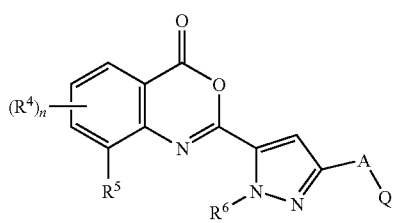
(V)

in which $R^4$, $R^5$, $R^6$, A, Q and n are defined by Formula I, with an amine of the formula (XV)

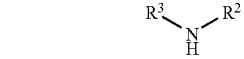
(XV)

in which $R^2$ and $R^3$ are defined by Formula I, in the presence of a diluent.

* * * * *